US006746839B1

(12) United States Patent
Duff et al.

(10) Patent No.: US 6,746,839 B1
(45) Date of Patent: *Jun. 8, 2004

(54) DIAGNOSTICS AND THERAPEUTICS FOR AN OBSTRUCTIVE AIRWAY DISEASE

(75) Inventors: Gordon W. Duff, Sheffield (GB); Francesco S. di Giovine, Ranmoor (GB); Peter J. Barnes, London (GB); Samson Lim, Concord (AU)

(73) Assignee: Interleukin Genetics, Inc., Waltham, MA (US)

( * ) Notice: Subject to any disclaimer, the term of this patent is extended or adjusted under 35 U.S.C. 154(b) by 35 days.

This patent is subject to a terminal disclaimer.

(21) Appl. No.: 09/584,950

(22) Filed: Jun. 1, 2000

Related U.S. Application Data

(63) Continuation-in-part of application No. 09/005,923, filed on Jan. 12, 1998, now Pat. No. 6,140,047.

(51) Int. Cl.$^7$ .......................... C12Q 1/68; C12P 19/34; C07H 21/04

(52) U.S. Cl. .................. 435/6; 435/91.2; 536/23.5; 536/24.31; 536/24.33

(58) Field of Search ................... 435/6, 91.2; 536/23.5, 536/24.31, 24.33

(56) References Cited

U.S. PATENT DOCUMENTS

| | | | |
|---|---|---|---|
| 4,582,788 A | 4/1986 | Erlich | 435/6 |
| 4,666,828 A | 5/1987 | Gusella | 435/6 |
| 4,801,531 A | 1/1989 | Frossard | 435/6 |
| 5,110,920 A | 5/1992 | Erlich | 536/27 |
| 5,268,267 A | 12/1993 | Smith | 435/6 |
| 5,596,072 A | * 1/1997 | Culpepper et al. | |
| 5,674,483 A | 10/1997 | Tu et al. | 424/85.2 |
| 5,686,246 A | 11/1997 | Kornman et al. | 435/6 |
| 6,090,816 A | * 7/2000 | Cavalla et al. | |
| 6,139,832 A | * 10/2000 | Li et al. | |
| 6,140,047 A | * 10/2000 | Duff et al. | |
| 6,210,877 B1 | * 4/2001 | Francis et al. | |

FOREIGN PATENT DOCUMENTS

| | | |
|---|---|---|
| WO | WO 95/01997 | 1/1995 |
| WO | WO 97/06180 | 2/1997 |
| WO | WO 98/54359 | 12/1998 |

OTHER PUBLICATIONS

Blakemore, et al.; J. Clin. Endocrinol. 80(1): 11–115 (1995).
Blakemore et al.; Hum. Genet. 97(3): 369–74 (1996).
Blakemore et al.; Arthritis Rheum. 37: 1380–85 (1994).
Clark et al., Nucleic Acid Research, 14(20: 7897 (1986).
Clay et al., Hum. Genet. 94: 407–410 (1994).
Cork, et al., J. Invest. Dermatol. 104 (5 Supp. ): 15s–16s (1995).
Di Giovine, et al., Cytokine 7: 606 (1995).

Di Giovine et al., "Single Base Polymorphism at –511 in the Human Interleukin–1βgene (IL 1β)", Human Molecular Genetics, 1 (6): pp. Abstract Only (1992).
Dinarello et al., "Anticytokine Strategies in the Treatment of the Systemic Inflammatory Response Syndrome", JAMA 269: 1829–1835 (1993).
Hiroyuki et al., "Classification of Asthma Based on Genetics", Japanese Journal of Thoracic Diseases 33 (Supp.) 97–99, Abstract only (1995).
Hizawa et al., "Genetics Analysis of Bronchial Asthma in Japanese Population—Fc epsilon RI beta Gene and beta 2 Adrenergic Receptor Gene", Japanese Journal of Clinical Medicine 54(2): 539–543, Abstract Only (1996).
Korman et al., J. Clin. Periodon. 24:72 (1997).
Mansfield et al., "Novel Genetic Association Between Ulcerative Colitis and the Anti–Inflammatory Cytokine Interleukin–1 Receptor Antagonist", Gastroenterology 106: 637–642 (1994).
Marsh et al., "Genetic Basis of IgE Responsiveness: Relevance to the Atopic Diseases", International Archives of Allergy & Immunology 107 9 (1–3): 25–28, Abstract Only (1995).
McDowell, T. et al.; "A Genetic Association Between Juvenile Rheumatoid Arthritis and a Novel Interleukin–1α Polymorphism", Arthritis & Rheumatism, 38: 221–228 (1995).
Molvig, et al., Scand. J. Immunol. 27: 705–716 (1988).
Nicklin et al., Genomics 19: 382–4 (1994).
Pociot et al., Eur. J. Clin. Invest. 22: 396–402 (1992).
Xu et al. , "Evidence For Two Unlinked Loci Regulating Total Serum IgE Levels", American Journal of Human Genetics 57(2): 425–430, Abstract Only (1995).
Zamel et al., "Asthma on Tristan da Cunha: Looking for the Genetic Link", American Journal of Respiratory & Critical Care Medicine 153(6 Pt1): 1902–1906 (1996).
International Search Report Completed on Jul. 26, 1999 and Mailed on Aug. 2, 1999.
Gabriele et al.; "Requirement for IL–13 Independently of IL–4 in Experimental Asthma", Science 282 (5397): 2261–2263 ( Dec. 18, 1998).
Graves et al.; "A Cluster of Seven Tightly Linked Polymorphisms in the IL–13 Gene is Associated with Total Serum IgE Levels in Three Population of White Children", Journal of Allergy and Clinical Immunology (online) vol. 105(3), (Mar. 2000).
Kraan et al.; "An IL–13 Promoter Polymorphism Associated with Increased Risk of Allergic Asthma", Genes and Immunity 1: 61–65, (1999).

(List continued on next page.)

*Primary Examiner*—Jeffrey Fredman
*Assistant Examiner*—Arun Kr. Chakrabarti
(74) *Attorney, Agent, or Firm*—Mintz Levin; Ivor R. Elrifi; Cynthia A. Kozakiewicz

(57) ABSTRACT

Methods and kits for detecting polymorphisms that are predictive of a subject's susceptibility to developing an obstructive airway disease, such as asthma, as well as for determining the relative severity of the disease are described. Assays for identify therapeutics are also described.

49 Claims, 15 Drawing Sheets

OTHER PUBLICATIONS

Figure 5:
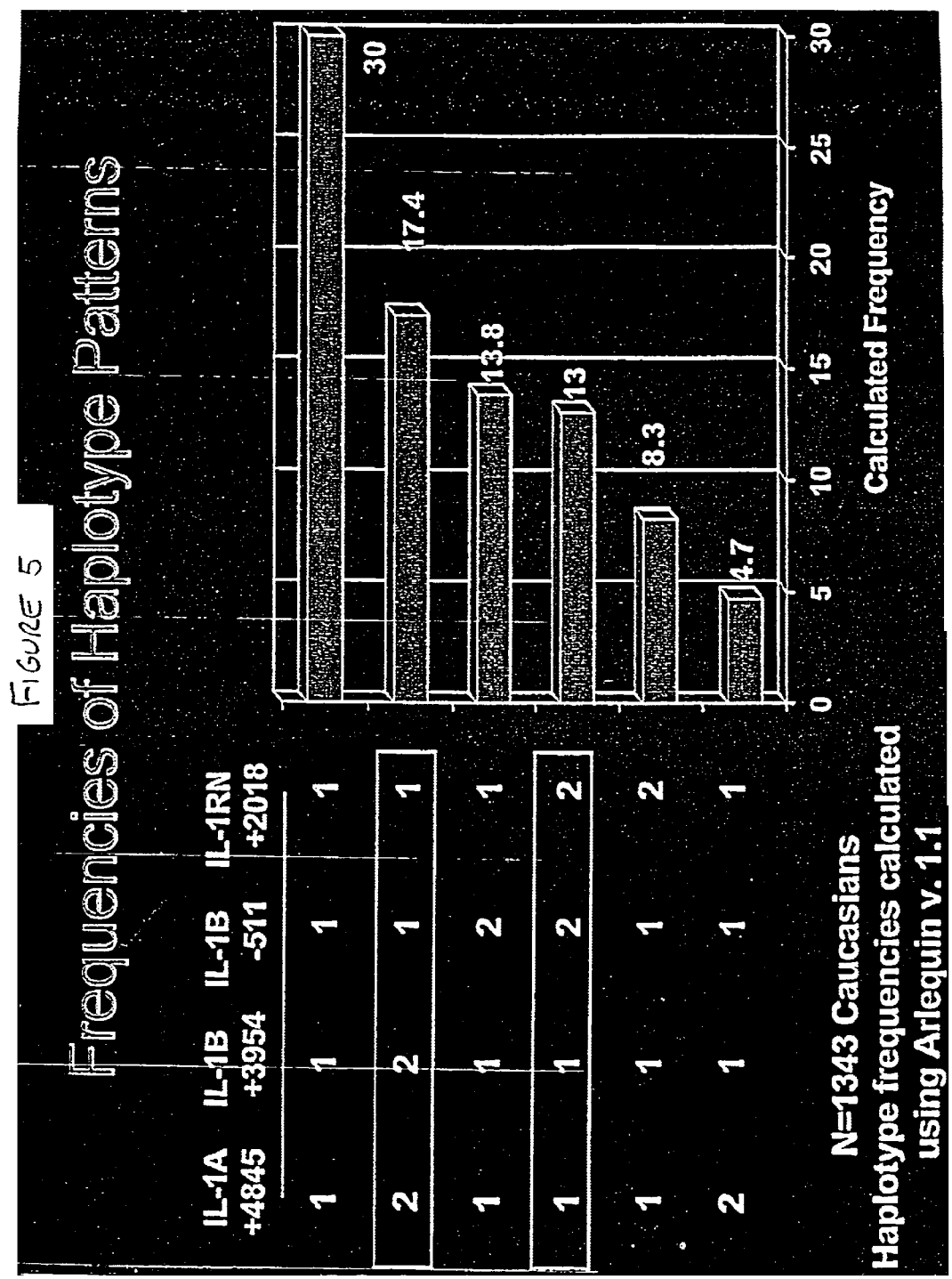

Marsh et al.; "Linkage Analysis of IL4 and Other Chromosome 5q31.1 Markers and Total Serum Immunoglobulin E Concentrations", Science 264: 1152–1156, (May 20, 1994).

Meyers et al.; "Evidence for a Locus Regulating Total Serum IgE Levels Mapping to Chromosome 5", Genomics 23 464–470, (1994).

Minty et al.; "Interleukin–13 is a New Human Lymphokine Regulating Inflammatory and Immune Response", Nature 362 : 248–250, (Mar. 18, 1993).

Pellegrino et al.; "Tumor Necrosis Factor–α and Interleukin–1 β", Minerva Pediatrica, 48 (7–8): 309–312, (1996).

Postma et al.; "Genetic Susceptibility to Asthma—Bronchial Hyperresponsiveness Coinherited with a Major Gene For Atopy", The New England Journal of Medicine 333(14): 894–900, ( Oct. 5, 1995).

Romagnani Sergio; "Short Analytical Review TH1 and TH2 in Human Diseases", Clinical Immunology and Immunopathology, 80(3): 225–235( Sep. 1996).

Rosenwasser J. Lanny; "IL–13 Genetics: Pale Rider or Horse of a Different Color?", Journal of Allergy and Clinical Immunology(online), vol. 105 (3), (Mar. 2000).

Stuart Mary, "The Asthma Challenge", Marketplace Strategies, Windhover Information Inc. ©1999, Start–Up Apr. 1999.

V. Gretchen; "Interleukin–13's Key Role in Asthma Shown", Science 282: 2168, ( Dec. 18, 1998 ).

Wills–Karp et al., "Interleukin–13 : Central Mediator of Allergic Asthma", Science 282: 2258–2260, (Dec. 18, 1998).

* cited by examiner

FIGURE 1A   DNA Sequence of the human IL-1A gene. (GenBank Accession No. X03833)

```
-1437  AAGCTTCTAC CCTAGTCTGG TGCTACACTT ACATTGCTTA CATCCAAGTG TGGTTATTTC
-1377  TGTGGCTCCT GTTATAACTA TTATAGCACC AGGTCTATGA CCAGGAGAAT TAGACTGGCA
-1317  TTAAATCAGA ATAAGAGATT TTGCACCTGC AATAGACCTT ATGACACCTA ACCAACCCCA
-1257  TTATTTACAA TTAAACAGGA ACAGAGGGAA TACTTTATCC AACTCACACA AGCTGTTTTC
-1197  CTCCCAGATC CATGCTTTTT TGCGTTTATT ATTTTTTAGA GATGGGGCT  TCACTATGTT
-1137  GCCCACACTG GACTAAAACT CTGGGCCTCA AGTGATTGTC CTGCCTCAGC CTCCTGAATA
-1077  GCTGGGACTA CAGGGGCATG CCATCACACC TAGTTCATTT CCTCTATTTA AAATATACAT
-1017  GGCTTAAACT CCAACTGGGA ACCCAAAACA TTCATTTGCT AAGAGTCTGG TGTTCTACCA
 -957  CCTGAACTAG GCTGGCCACA GGAATTATAA AAGCTGAGAA ATTCTTTAAT AATAGTAACC
 -897  AGGCAACATC ATTGAAGGCT CATATGTAAA AATCCATGCC TTCCTTTCTC CCAATCTCCA
 -837  TTCCCAAACT TAGCCACTGG TTCTGGCTGA GGCCTTACGC ATACCTCCG  GGGCTTGCAC
 -777  ACACCTTCTT CTACAGAAGA CACACCTTGG GCATATCCTA CAGAAGACCA GGCTTCTCTC
 -717  TGGTCCTTGG TAGAGGGCTA CTTTACTGTA ACAGGGCCAG GGTGGAGAGT TCTCTCCTGA
 -657  AGCTCCATCC CCTCTATAGG AAATGTGTTG ACAATATTCA GAAGAGTAAG AGGATCAAGA
 -597  CTTCTTTGTG CTCAAATACC ACTGTTCTCT TCTCTACCCT GCCCTAACCA GGAGCTTGTC
 -537  ACCCCAAACT CTGAGGTGAT TTATGCCTTA ATCAAGCAAA CTTCCCTCTT CAGAAAAGAT
 -477  GGCTCATTTT CCCTCAAAAG TTGCCAGGAG CTGCCAAGTA TTCTGCCAAT TCACCCTGGA
 -417  GCACAATCAA CAAATTCAGC CAGAACACAA CTACAGCTAC TATTAGAACT ATTATTATTA
 -357  ATAAATTCCT CTCCAAATCT AGCCCCTTGA CTTCGGATTT CACGATTTCT CCCTTCCTCC
 -297  TAGAAACTTG ATAAGTTTCC CGCGCTTCCC TTTTTCTAAG ACTACATGTT TGTCATCTTA
 -237  TAAAGCAAAG GGGTGAATAA ATGAACCAAA TCAATAACTT CTGGAATATC TGCAAACAAC
 -177  AATAATATCA GCTATGCCAT CTTTCACTAT TTTAGCCAGT ATCGAGTTGA ATGAACATAG
 -117  AAAAATACAA AACTGAATTC TTCCCTGTAA ATTCCCGTT  TTGACGACGC ACTTGTAGCC
  -57  ACGTAGCCAC GCCTACTTAA GACAATTACA AAAGGCGAAG AAGACTGACT CAGGCTTAAG
    4  CTGCCAGCCA GAGAGGGAGT CATTTCATTG GCGTTTGAGT CAGCAAAGGT ATTGTCCTCA
   64  CATCTCTGGC TATTAAAGTA TTTTCTGTTG TTGTTTTTCT CTTTGGCTGT TTTCTCTCAC
  124  ATTGCCTTCT CTAAAGCTAC AGTCTCTCCT TTCTTTTCTT GTCCCTCCCT GGTTTGGTAT
  184  GTGACCTAGA ATTACAGTCA GATTTCAGAA AATGATTCTC TCATTTGCT  GATAAGGACT
  244  GATTCGTTTT ACTGAGGGAC GGCAGAACTA GTTTCCTATG AGGGCATGGG TGAATACAAC
  304  TGAGGCTTCT CATGGGAGGG AATCTCTACT ATCCAAAATT ATTAGGAGAA AATTGAAAAT
  364  TTCCAACTCT GTCTCTCTCT TACCTCTGTG TAAGCAAAT  ACCTTATTCT TGTGGTGTTT
  424  TTGTAACCTC TTCAAACTTT CATTGATTGA ATGCCTGTTC TGGCAATACA TTAGGTTGGG
  484  CACATAAGGA ATACCAACAT AAATAAAACA TTCTAAAAGA AGTTTACGAT CTAATAAAGG
  544  AGACAGGTAC ATAGCAAACT AATTCAAAGG AGCTAGAAGA TGGAGAAAAT GCTGAATGTG
  604  GACTAAGTCA TTCAACAAAG TTTTCAGGAA GCACAAAGAG GAGGGGCTCC CCTCACAGAT
  664  ATCTGGATTA GAGGCTGGCT GAGCTGATGG TGGCTGGTGT TCTCTGTTGC AGAAGTCAAG
  724  ATGGCCAAAG TTCCAGACAT GTTTGAAGAC CTGAAGAACT GTTACAGGTA AGGAATAAGA
  784  TTTATCTCTT GTGATTTAAT GAGGGTTTCA AGGCTCACCA GAATCCAGCT AGGCATAACA
  844  GTGGCCAGCA TGGGGCAGG  CCGGCAGAGG TTGTAGAGAT GTGTACTAGT CCTGAAGTCA
  904  GAGCAGGTTC AGAGAAGACC CAGAAAAACT AAGCATTCAG CATGTTAAAC TGAGATTACA
  964  TTGGCAGGGA GACCGCCATT TTAGAAAAAT TATTTTTGAG GTCTGCTGAG CCCTACATGA
 1024  ATATCAGCAT CAACTTAGAC ACAGCCTCTG TTGAGATCAC ATGCCCTGAT ATAAGAATGG
 1084  GTTTTACTGG TCCATTCTCA GGAAAACTTG ATCTCATTCA GGAACAGGAA ATGGCTCCAC
 1144  AGCAAGCTGG GCATGTGAAC TCACATATGC AGGCAAATCT CACTCAGATG TAGAAGAAAG
 1204  GTAAATGAAC ACAAAGATAA AATTACGGAA CATATTAAAC TAACATGATG TTTCCATTAT
 1264  CTGTAGTAAA TACTAACACA AACTAGGCTG TCAAAATTTT GCCTGGATAT TTTACTAAGT
 1324  ATAAATTATG AAATCTGTTT TAGTGAATAC ATGAAAGTAA TGTGTAACAT ATAAT CTATT
 1384  TGGTTAAAAT AAAAAGGAAG TGCTTCAAAA CCTTTCTTTT CTCTAAAGGA GCTTAACATT
 1444  CTTCCCTGAA CTTCAATTAA AGCTCTTCAA TTTGTTAGCC AAGTCCAATT TTTACAGATA
 1504  AAGCACAGGT AAAGCTCAAA GCCTGTCTTG ATGACTACTA ATTCCAGATT AGTAAGATAT
```

```
1564  GAATTACTCT ACCTATGTGT ATGTGTAGAA GTCCTTAAAT TTCAAAGATG ACAGTAATGG
1624  CCATGTGTAT GTCTGTGACC CACAACTATC ATGGTCATTA AAGTACATTG GCCAGAGACC
1684  ACATGAAATA ACAACAATTA CATTCTCATC ATCTTATTTT GACAGTGAAA ATGAAGAAGA
1744  CAGTTCCTCC ATTGATCATC TGTCTCTGAA TCAGGTAAGC AAATGACTGT AATTCTCATG
1804  GGACTGCTAT TCTTACACAG TGGTTTCTTC ATCCAAAGAG AACAGCAATG ACTTGAATCT
1864  TAAATACTTT TGTTTTACCC TCACTAGAGA TCCAGAGACC TGTCTTTCAT TATAAGTGAG
1924  ACCAGCTGCC TCTCTAAACT AATAGTTGAT GTGCATTGGC TTCTCCCAGA ACAGAGCAGA
1984  ACTATCCCAA ATCCCTGAGA ACTGGAGTCT CCTGGGGCAG GCTTCATCAG GATGTTAGTT
2044  ATGCCATCCT GAGAAAGCCC CGCAGGCCGC TTCACCAGGT GTCTGTCTCC TAACGTGATG
2104  TGTTGTGGTT GTCTTCTCTG ACACCAGCAT CAGAGGTTAG AGAAAGTCTC CAAACATGAA
2164  GCTGAGAGAG AGGAAGCAAG CCAGCTGAAA GTGAGAAGTC TACAGCCACT CATCAATCTG
2224  TGTTATTGTG TTTGGAGACC ACAAATAGAC ACTATAAGTA CTGCCTAGTA TGTCTTCAGT
2284  ACTGGCTTTA AAAGCTGTCC CCAAAGGAGT ATTTCTAAAA TATTTTGAGC ATTGTTAAGC
2344  AGATTTTTAA CCTCCTGAGA GGGAACTAAT TGGAAAGCTA CCACTCACTA CAATCATTGT
2404  TAACCTATTT AGTTACAACA TCTCATTTTT GAGCATGCAA ATAAATGAAA AAGTCTTCCT
2464  AAAAAAATCA TCTTTTTATC CTGGAAGGAG GAAGGAAGGT GAGACAAAAG GGAGAGAGGG
2524  AGGGAAGCCT AATGAAACAC CAGTTACCTA AGACCAGAAT GGAGATCCTC CTCACTACCT
2584  CTGTTGAATA CAGCACCTAC TGAAAGAACT TTCATTCCCT GACCATGAAC AGCCTCTCAG
2644  CTTCTGTTTT CCTTCCTCAC AGAAATCCTT CTATCATGTA AGCTATGGCC CACTCCATGA
2704  AGGCTGCATG GATCAATCTG TGTCTCTGAG TATCTCTGAA ACCTCTAAAA CATCCAAGCT
2764  TACCTTCAAG GAGAGCATGG TGGTAGTAGC AACCAACGGG AAGGTTCTGA AGAAGAGACG
2824  GTTGAGTTTA AGCCAATCCA TCACTGATGA TGACCTGGAG GCCATCGCCA ATGACTCAGA
2884  GGAAGGTAAG GGGTCAAGCA CAATAATATC TTTCTTTTAC AGTTTTAAGC AAGTAGGGAC
2944  AGTAGAATTT AGGGGAAAAT TAAACGTGGA GTCAGAATAA CAAGAAGACA CCAAGCATT
3004  AGTCTGGTAA CTATACAGAG GAAAATTAAT TTTTATCCTT CTCCAGGAGG GAGAAATGAG
3064  CAGTGGCCTG AATCGAGAAT ACTTGCTCAC AGCCATTATT TCTTAGCCAT ATTGTAAAGG
3124  TCGTGTGACT TTTAGCCTTT CAGGAGAAAG CAGTAATAAG ACCACTTACG AGCTATGTTC
3184  CTCTCATACT AACTATGCCT CCTTGGTCAT GTTACATAAT CTTTTCGTGA TTCAGTTTCC
3244  TCTACTGTAA AATGGAGATA ATCAGAATCC CCCACTCATT GGATTGTTGT AAAGATTAAG
3304  AGTCTCAGGC TTTACAGACT GAGCTAGCTG GGCCCTCCTG ACTGTTATAA AGATTAAATG
3364  AGTCAACATC CCCTAACTTC TGGACTAGAA TAATGTCTGG TACAAAGTAA GCACCCAATA
3424  AATGTTAGCT ATTACTATCA TTATTATTAT TATTTTATTT TTTTTTTTG AGATGGAGTC
3484  TGGCTCTGTC ACCCAGGCTG GAGTGCAGTG GCACAATCTC GGCTCACTGC AAGCTCTGCC
3544  TCCTGGGTTC ATGCCATTCT CCTGCCTCAG CCTCCCGAGT AAGCTGGGAA TACAGGCACC
3604  CGCCACTGTT CCCGGCTAAT TTTTTGTATT TTTAGTAGAG ACGGAGTTTC ACCGTGGTCT
3664  CCATCTCCTC GTGATCCACC CACCTTGGCC TCCCAAAGTG CCGGGATTAC AGGCGTGAGC
3724  CACCGCGCCC GGCCTATTAT TATTATTATT ACTACTACTA CTACCTATAT GAATACTACC
3784  AGCAATACTA ATTTATTAAT GACTGGATTA TGTCTAAACC TCACAAGAAT CCTACCTTCT
3844  CATTTTACAT AAAAGGAAAC TAAGCTCATT GAGATAGGTA AACTGCCCAA TGGCATACAT
3904  CTGTAAGTGG GAGAGCCTCA AATCTAATTC AGTTCTACCT GAGTAAAAAA ATCATGGTTT
3964  CTCCTCCATC CCTTTACTGT ACAAGCCTCC ACATGAACTA TAAACCCAAT ATTCCTGTTT
4024  TTAAGATAAT ACCTAAGCAA TAACGCATGT TCACCTAGAA GGTTTTAAAA TGTAACAAAA
4084  TATAAGAAAA TAAAATCAC TCATATCGTC AGTGAGAGTT TACTACTGCC AGCACTATGG
4144  TATGTTTCCT TAAAATCTTT GCTATACACA TACCTACATG TGAACAAATA TGTCTAACAT
4204  CAAGACCACA CTATTTACAA CTTTATATCC AGCTTTTCTT ACTTAGCAAT GTATTGAGGA
4264  CATTTTAGAG TGCCCGTTTT TCACCATTAT AAGCAATGCA ACAATGAACA TCTGTATAAA
4324  TAAATATTCA TTTCTCTCAC CCTTTATTTC CTTAGAATAT ATTCCTAGAA GTAGAATTTC
4384  CCAGAGCCAT GAGGATTTGT GACGCTATTG ATATGTGCCA CTTTGCACTC TCTGTGACAT
4444  ATATAATTAT TTTAATGCA TTCATTTTTT TCTCAGAGTG CATTCGTTTG AAAACATAGA
4504  CGGGAAATAC TGGTAGTCTT CCTTGTCAGT TAGAAACACC CAAACAATGA AAATGAAAA
4564  AGTTGCACAA ATAGTCTCTA AAAACAATGA AACTATTGCC TGAGGAATTG AAGTTTAAAA
4624  AGAAGCACAT AAGCAACAAC AAGGATAATC CTAGAAAACC AGTTCTGCTG ACTGGGTGAT
4684  TTCACTTCTC TTTGCTTCCT CATCTGGATT GGAATATTCC TAATACCCCC TCCAGAACTA
```

FIGURE 1B

```
4744  TTTTCCCTGT TTGTACTAGA CTGTGTATAT CATCTGTGTT TGTACATAGA CATTAATCTG
4804  CACTTGTGAT CATGGTTTTA GAAATCATCA AGCCTAGGTC ATCACCTTTT AGCTTCCTGA
4864  GCAATGTGAA ATACAACTTT ATGAGGATCA TCAAATACGA ATTCATCCTG AATGACGCCC
4924  TCAATCAAAG TATAATTCGA GCCATGATC  AGTACCTCAC GGCTGCTGCA TTACATAATC
4984  TGGATGAAGC AGGTACATTA AAATGGCACC AGACATTTCT GTCATCCTCC CCTCCTTTCA
5044  TTTACTTATT TATTTATTTC AATCTTTCTG CTTGCAAAAA ACATACCTCT TCAGAGTTCT
5104  GGGTTGCACA ATTCTTCCAG AATAGCTTGA AGCACAGCAC CCCCATAAAA ATCCCAAGCC
5164  AGGGCAGAAG GTTCAACTAA ATCTGGAAGT TCCACAAGAG AGAAGTTTCC TATCTTTGAG
5224  AGTAAAGGGT TGTGCACAAA GCTAGCTGAT GTACTACCTC TTTGGTTCTT TCAGACATTC
5284  TTACCCTCAA TTTTAAAACT GAGGAAACTG TCAGACATAT TAAATGATTT ACTCAGATTT
5344  ACCCAGAAGC CAATGAAGAA CAATCACTCT CCTTTAAAAA GTCTGTTGAT CAAACTCACA
5404  AGTAACACCA AACCAGGAAG ATCTTTATTA TCTCTGATAA CATATTTGTG AGGCAAAACC
5464  TCCAATAAGC TACAAATATG GCTTAAAGGA TGAAGTTTAG TGTCCAAAAA CTTTTATCAC
5524  ACACATCCAA TTTTCATGGC GGACATGTTT TAGTTTCAAC AGTATACATA TTTTCAAAGG
5584  TCCAGAGAGG CAATTTTGCA ATAAACAAGC AAGACTTTTT CTGATTGGAT GCACTTCAGC
5644  TAACATGCTT TCAACTCTAC ATTTACAAAT TATTTTGTGT TCTATTTTTC TACTTAATAT
5704  TATTTCTGCA ATTTTCCCAA TATTGACATC GTGTATGTAT TTGCCATTTT TAATATCACT
5764  AGACAATTCA ATCAGGTTGC TACGTTGGTC CCTTGGGTTT ACTCTAAATA GCTTGATTGC
5824  AAATATCTTT GTATATATTA TTGTTTTTTC TCCTATCTTG TAATTTCTTT GAGCACATCC
5884  CAAAGAGGAA TGCCTAGATC AATGGGCACA ATAATTTGA  CAGCTCTTAT TAAACATTAT
5944  TCTGTAAGTA AAAACTGAAC TACTTTTCAG TATCACTAGC AACATATGAG TGTATCAGCT
6004  TCCTAAACCC CTCCATGTTA GGTCATTATG AACTTATGAT CTAACAAATT ACAGGGTCTT
6064  ATCCCACTAA TGAAATTATA AGAGATTCAA CACTTATTCA GCCCGAAGG  ATTCATTCAA
6124  CGTAGAAAAT TCTAAGAACA TTAACCAAGT ATTTACCTGC CTAGTGAGTG TGGAAGACAT
6184  TGTGAAGGAC ACAAAGATGT ATAGAATTCC ATTCCTGACT TCCAGGTATT TACACCATAG
6244  GTGGGGACCT AACTACACAC ACACACACAC ACACACACAC ACACACACAC ACCATGCACA
6304  CACAATCTAC ATCAACACTT GATTTATAC  AAATACAATG AATTTACTTT CTTTTTGGTT
6364  CTTCTCTTCA CCAGTGAAAT TTGACATGGG TGCTTATAAG TCATCAAAGG ATGATGCTAA
6424  AATTACCGTG ATTCTAAGAA TCTCAAAAAC TCAATTGTAT GTGACTGCCC AAGATGAAGA
6484  CCAACCAGTG CTGCTGAAGG TCAGTTGTCC TTTGTCTCCA ACTTACCTTC ATTTACATCT
6544  CATATGTTTG TAAATAAGCC CAATAGGCAG ACACCTCTAA CAAGGTGACA CTGTCCTCTT
6604  TCCTTCCTAC CACAGCCCCC ACCTACCCAC CCCACTCCCA TTGATTCCAG AGGCGTGCCT
6664  AGGCAGGATC TATGAGAAAA TATAACAGAG AGTAAGAGGA AAATTACCTT CTTTCTTTTT
6724  CCTTTCCCTG CCTGACCTTA TTCACCTCCC ATCCCAGAGC ATCCATTTAT TCCATTGATC
6784  TTTACTGACA TCTATTATCT GACCTACACA ATACTAGACA TTAGGACAAT GTGGCCTGCC
6844  TCCAAGAAAC TCAAATAAGC CAACTGAGAT CAGAGAGGAT TAATCACCTG CCAATGGGCA
6904  CAAAGCAACA AGCTGGGAGC CAAGTCCCAA AATGGGGCCT GCTGCTTCCA GTTCCCTCT
6964  CTCTGCATTG ATGTCAGCAT TATCCTTCGT CCCAGTCCTG TCTCCACTAC CACTTTCCCC
7024  CTCAAACACA CACACACACA ACAGCCTTAG ATGTTTCTC  CACTGATAAG TAGGTGACTC
7084  AATTTGTAAG TATATAATCC AAGACCTTCT ATTCCCAAGT AGAATTTATG TGCCTGCCTG
7144  TGCTTTTCTA CCTGGATCAA GTGATGTCTA CAGAGTAGGG CAGTAGCTTC ATTCATGAAC
7204  TCATTCAACA AGCATTATTC ACTGAGAGCC TTGTATTTTT CAGGCATAGT GCCAACAGCA
7264  GTGTGGACAG TGGTGCATCA AAGCCTCTAG TCTCATAGAA CTTAGTCTTC TGGAGGATAT
7324  GGAAAACAGA CAACCCAAAC AACCAACAAA AGAGCAAGAT GCTGCAAAAA AAAAAAAAAT
7384  GAATAGGGTG CTAAGATAGA GAAAGTGGG  AGAGTGCTAT TTAGACAAAG TGGTAAAAAC
7444  AAAGCCCCTT GTGAGATGAG AGCTGCCGAC AGAGGGGCG  GGTCATGGTT GTGGGTTTTT
7504  GGGTAGGACA TTCAGAGGAG GGGCGGGTC  GTGGTTGTGG GTTTTGGGT  AGGACATTCA
7564  GAGGAGGGGG CGGGTCGTGG TTGTGGGTTT TGGGTAGGA  CATTCAGAGG AGGGGCGGG
7624  TCGTGGTTGT GGGTTTTGG  GTAGGACATT CAGAGGAGGG GGCGGGTCGT GGTTGTGGGT
7684  TTTGGGACA  TTCAGAGGAG TCTGAATGCA CCCAGGCCTA CAACTTCAAG ATGGTAAAGG
7744  ACAGCTCCAA GGATCAGAAG AAGCATTCTT GGAACTGGGG CATTTTGAGA AGGAGGAAAA
7804  ATATGCAGAG ACTAGTGCTT GCAGAGCTTG CATTTGGATT TCATTTGAGG TACAATGAAA
7864  ACCCATTAAT GGGTTTCACA CAGTGCAATG GCCTGACCTC ACTTATATTT CCTAAAATAG
```

FIGURE 1C

```
 7924  AAAACAGATC AGAAGGAAGG CAATAGAGAA GCAGAAAGTC CAATGAGGAG GTTTCACAGC
 7984  AGTCATGGGG GTGGGGTAAG GAAAAGAAGT GGAAAGAAAC AGACAGAATT GGGTTATATT
 8044  TTGGAGATAG AACCAACAGA AGGAAGAGGA GAAACAACAT TTACTGAGAA GGGAAAAAGT
 8104  AGGAGAGGAA TAGGTTTGGG AAATAAATCC TGCTGACATT GGAAACCCCA AGGAAGCCTC
 8164  AAAAGTATAT TTACTTGCTT TAGATTTAAA AGAATAGGAA AGAAGCATCT CAACTTGGAA
 8224  TTTGAAATCT ATTTTTCCAT AAAAGTATTG TTAAATTCTA CTCATACTCA CAAGAAAAGT
 8284  ACATTCTAAA GAGTATATTG AAAGAGTTTA CTGATATACT TAGGAATTTT GTGTGTATGT
 8344  GTGTGTGTGT ATGTGTGTGT GTGTGTTTAA CCTTCAATTG TTGACTTAAA TACTGAGATA
 8404  AATGTCATCT AAATGCTAAA TTGATTTCCC AAAGGTATGA TTTGTTCACT TGGAGATCAA
 8464  AATGTTTAGG GGGCTTAGAA TCACTGTAGT GCTCAGATTT GATGCAAAAT GTCTTAGGCC
 8524  TATGTTGAAG GCAGGACAGA ACAATGTTT CCCTCCTACC TGCCTGGATA CAGTAAGATA
 8584  CTAGTGTCAC TGACAATCTT CATAACTAAT TTAGATCTCT CTCCAATCAA CTAAGGAAAT
 8644  CAACTCTTAT TAATAGACTG GGCCACACAT CTACTAGGCA TGTAATAAAT GCTTGCTGAA
 8704  TGAACAAATG AATGAAGAGC CTATAGCATC ATGTTACAGC CATAGTCCTA AAGTGGTGTT
 8764  TCTCATGAAG GCCAAATGCT AAGGGATTGA GCTTCAGTCC TTTTTCTAAC ATCTTGTTCT
 8824  CTAACAGAAT TCTCTTCTTT TCTTCATAGG AGATGCCTGA GATACCCAAA ACCATCACAG
 8884  GTAGTGAGAC CAACCTCCTC TTCTTCTGGG AAACTCACGG CACTAAGAAC TATTTCACAT
 8944  CAGTTGCCCA TCCAAACTTG TTTATTGCCA CAAAGCAAGA CTACTGGGTG TGCTTGGCAG
 9004  GGGGGCCACC CTCTATCACT GACTTTCAGA TACTGGAAAA CCAGGCGTAG GTCTGGAGTC
 9064  TCACTTGTCT CACTTGTGCA GTGTTGACAG TTCATATGTA CCATGTACAT GAAGAAGCTA
 9124  AATCCTTTAC TGTTAGTCAT TTGCTGAGCA TGTACTGAGC CTTGTAATTC TAAATGAATG
 9184  TTTACACTCT TTGTAAGAGT GGAACCAACA CTAACATATA ATGTTGTTAT TTAAAGAACA
 9244  CCCTATATTT TGCATAGTAC CAATCATTTT AATTATTATT CTTCATAACA ATTTTAGGAG
 9304  GACCAGAGCT ACTGACTATG GCTACCAAAA AGACTCTACC CATATTACAG ATGGGCAAAT
 9364  TAAGGCATAA GAAAACTAAG AAATATGCAC AATAGCAGTT GAAACAAGAA GCCACAGACC
 9424  TAGGATTTCA TGATTTCATT TCAACTGTTT GCCTTCTGCT TTTAAGTTGC TGATGAACTC
 9484  TTAATCAAAT AGCATAAGTT TCTGGGACCT CAGTTTTATC ATTTTCAAAA TGGAGGGAAT
 9544  AATACCTAAG CCTTCCTGCC GCAACAGTTT TTTATGCTAA TCAGGGAGGT CATTTTGGTA
 9604  AAATACTTCT CGAAGCCGAG CCTCAAGATG AAGGCAAAGC ACGAAATGTT ATTTTTTAAT
 9664  TATTATTTAT ATATGTATTT ATAAATATAT TTAAGATAAT TATAATATAC TATATTTATG
 9724  GGAACCCCTT CATCCTCTGA GTGTGACCAG GCATCCTCCA CAATAGCAGA CAGTGTTTTC
 9784  TGGGATAAGT AAGTTTGATT TCATTAATAC AGGGCATTTT GGTCCAAGTT GTGCTTATCC
 9844  CATAGCCAGG AAACTCTGCA TTCTAGTACT TGGGAGACCT GTAATCATAT AATAAATGTA
 9904  CATTAATTAC CTTGAGCCAG TAATTGGTCC GATCTTTGAC TCTTTTGCCA TTAAACTTAC
 9964  CTGGGCATTC TTGTTTCATT CAATTCCACC TGCAATCAAG TCCTACAAGC TAAAATTAGA
10024  TGAACTCAAC TTTGACAACC ATGAGACCAC TGTTATCAAA ACTTTCTTTT CTGGAATGTA
10084  ATCAATGTTT CTTCTAGGTT CTAAAAATTG TGATCAGACC ATAATGTTAC ATTATTATCA
10144  ACAATAGTGA TTGATAGAGT GTTATCAGTC ATAACTAAAT AAAGCTTGCA ACAAAATTCT
10204  CTGACACATA GTTATTCATT GCCTAATCA TTATTTTACT GCATGGTAAT TAGGGACAAA
10264  TGGTAAATGT TTACATAAAT AATTGTATTT AGTGTTACTT TATAAAATCA AACCAAGATT
10324  TTATATTTTT TTCTCCTCTT TGTTAGCTGC CAGTATGCAT AAATGGCATT AAGAATGATA
10384  ATATTTCCGG GTTCACTTAA AGCTCATATT ACACATACAC AAAACATGTG TTCCCATCTT
10444  TATACAAACT CACACATACA GAGCTACATT AAAAACAACT AATAGGCCAG GCACGGTGGC
10504  TCAGACCTGT AATCCCAGCA CTTTGGGAGG
```

FIGURE 1D

FIGURE 2A  DNA Sequence of the human IL-1B gene. (GenBank Accession No. X04500)

```
-1933 AGAAAGAAAG AGAGAGAGAA AGAAAAGAAA GAGGAAGGAA GGAAGGAAGG AAGAAAGACA
-1873 GGCTCTGAGG AAGGTGGCAG TTCCTACAAC GGGAGAACCA GTGGTTAATT TGCAAAGTGG
-1813 ATCCTGTGGA GGCANNCAGA GGAGTCCCCT AGGCCACCCA GACAGGGCTT TTAGCTATCT
-1753 GCAGGCCAGA CACCAAATTT CAGGAGGGCT CAGTGTTAGG AATGGATTAT GGCTTATCAA
-1693 ATTCACAGGA AACTAACATG TTGAACAGCT TTTAGATTTC CTGTGGAAAA TATAACTTAC
-1633 TAAAGATGGA GTTCTTGTGA CTGACTCCTG ATATCAAGAT ACTGGGAGCC AAATTAAAAA
-1573 TCAGAAGGCT GCTTGGAGAG CAAGTCCATG AAATGCTCTT TTTCCCACAG TAGAACCTAT
-1513 TTCCCTCGTG TCTCAAATAC TTGCACAGAG GCTCACTCCC TTGGATAATG CAGAGCGAGC
-1453 ACGATACCTG GCACATACTA ATTTGAATAA AATGCTGTCA AATTCCCATT CACCCATTCA
-1393 AGCAGCAAAC TCTATCTCAC CTGAATGTAC ATGCCAGGCA CTGTGCTAGA CTTGGCTCAA
-1333 AAAGATTTCA GTTCCTGGA GGAACCAGGA GGGCAAGGTT TCAACTCAGT GCTATAAGAA
-1273 GTGTTACAGG CTGGACACGG TGGCTCACGC CTGTAATCCC AACATTTGGG AGGCCGAGGC
-1213 GGGCAGATCA CAAGGTCAGG AGATCGAGAC CATCCTGGCT AACATGGTGA AACCCTGTCT
-1153 CTACTAAAAA TACAAAAAAT TAGCCGGGCG TTGGCGGCAG GTGCCTGTAG TCCCAGCTGC
-1093 TGGGGAGGCT GAGGCAGGAG AATGGTGTGA ACCCGGGAGG CGGAACTTGC AGGGGCCGA
-1033 GATCGTGCCA CTGCACTCCA GCCTGGGCGA CAGAGTGAGA CTCTGTCTCA AAAAAAAAAA
 -973 AAAAGTGTTA TGATGCAGAC CTGTCAAAGA GGCAAAGGAG GGTGTTCCTA CACTCCAGGC
 -913 ACTGTTCATA ACCTGGACTC TCATTCATTC TACAAATGGA GGGCTCCCCT GGGCAGATCC
 -853 CTGGAGCAGG CACTTTGCTG GTGTCTCGGT TAAAGAGAAA CTGATAACTC TTGGTATTAC
 -793 CAAGAGATAG AGTCTCAGAT GGATATTCTT ACAGAAACAA TATTCCCACT TTTCAGAGTT
 -733 CACCAAAAAA TCATTTTAGG CAGAGCTCAT CTGGCATTGA TCTGGTTCAT CCATGAGATT
 -673 GGCTAGGGTA ACAGCACCTG GTCTTGCAGG GTTGTGTGAG CTTATCTCCA GGGTTGCCCC
 -613 AACTCCGTCA GGAGCCTGAA CCCTGCATAC CGTATGTTCT CTGCCCCAGC CAAGAAAGGT
 -553 CAATTTTCTC CTCAGAGGCT CCTGCAATTG ACAGAGAGCT CCCGAGGCAG AGAACAGCAC
 -493 CCAAGGTAGA GACCCACACC CTCAATACAG ACAGGGAGGG CTATTGGCCC TTCATTGTAC
 -433 CCATTTATCC ATCTGTAAGT GGGAAGATTC CTAAACTTAA GTACAAAGAA GTGAATGAAG
 -373 AAAAGTATGT GCATGTATAA ATCTGTGTGT CTTCCACTTT GTCCCACATA TACTAAATTT
 -313 AAACATTCTT CTAACGTGGG AAAATCCAGT ATTTTAATGT GGACATCAAC TGCACAACGA
 -253 TTGTCAGGAA AACAATGCAT ATTTGCATGG TGATACATTT GCAAAATGTG TCATAGTTTG
 -193 CTACTCCTTG CCCTTCCATG AACCAGAGAA TTATCTCAGT TTATTAGTCC CCTCCCCTAA
 -133 GAAGCTTCCA CCAATACTCT TTTCCCCTTT CCTTTAACTT GATTGTGAAA TCAGGTATTC
  -73 AACAGAGAAA TTTCTCAGCC TCCTACTTCT GCTTTTGAAA GCTATAAAAA CAGCGAGGGA
  -13 GAAACTGGCA GATACCAAAC CTCTTCGAGG CACAAGGCAC AACAGGCTGC TCTGGGATTC
   48 TCTTCAGCCA ATCTTCATTG CTCAAGTATG ACTTAATCT TCCTTACAAC TAGGTGCTAA
  108 GGGAGTCTCT CTGTCTCTCT GCCTCTTTGT GTGTATGCAT ATTCTCTCTC TCTCTCTCTT
  168 TCTTTCTCTG TCTCTCCTCT CCTTCCTCTC TGCCTCCTCT CTCAGCTTTT TGCAAAAATG
  228 CCAGGTGTAA TATAATGCTT ATGACTCGGG AAATATTCTG GGAATGGATA CTGCTTATCT
  288 AACAGCTGAC ACCCTAAAGG TTAGTGTCAA AGCCTCTGCC CCAGCTCTCC TAGCCAATAC
  238 ATTGCTAGTT GGGGTTTGGT TTAGCAAATG CTTTTCTCTA GACCCAAAGG ACTTCTCTTT
  308 CACACATTCA TTCATTTACT CAGAGATCAT TTCTTTGCAT GACTGCCATG CACTGGATGC
  468 TGAGAGAAAT CACACATGAA CGTAGCCGTC ATGGGGAAGT CACTCATTTT CTCCTTTTTA
  528 CACAGGTGTC TGAAGCAGCC ATGGCAGAAG TACCTGAGCT CGCCAGTGAA ATGATGGCTT
  588 ATTACAGGTC AGTGGAGACG CTGAGACCAG TAACATGAGC AGGTCTCCTC TTTCAAGAGT
  648 AGAGTGTTAT CTGTGCTTGG AGACCAGATT TTTCCCCTAA ATTGCCTCTT TCAGTGGCAA
  708 ACAGGGTGCC AAGTAAATCT GATTTAAAGA CTACTTTCCC ATTACAAGTC CCTCCAGCCT
  768 TGGGACCTGG AGGCTATCCA GATGTGTTGT TGCAAGGGCT TCCTGCAGAG GCAAATGGGG
  828 AGAAAAGATT CCAAGCCCAC AATACAAGGA ATCCCTTTGC AAAGTGTGGC TTGGAGGGAG
  888 AGGGAGAGCT CAGATTTTAG CTGACTCTGC TGGGCTAGAG GTTAGGCCTC AAGATCCAAC
  948 AGGGAGCACC AGGGTGCCCA CCTGCCAGGC CTAGAATCTG CCTTCTGGAC TGTTCTGCGC
 1008 ATATCACTGT GAAACTTGCC AGGTGTTTCA GGCAGCTTTG AGAGGCAGGC TGTTTGCAGT
```

```
1068  TTCTTATGAA CAGTCAAGTC TTGTACACAG GGAAGGAAAA ATAAACCTGT TTAGAAGACA
1128  TAATTGAGAC ATGTCCCTGT TTTTATTACA GTGGCAATGA GGATGACTTG TTCTTTGAAG
1188  CTGATGGCCC TAAACAGATG AAGGTAAGAC TATGGGTTTA ACTCCCAACC CAAGGAAGGG
1248  CTCTAACACA GGGAAAGCTC AAAGAAGGGA GTTCTGGGCC ACTTTGATGC CATGGTATTT
1308  TGTTTTAGAA AGACTTTAAC CTCTTCCAGT GAGACACAGG CTGCACCACT TGCTGACCTG
1368  GCCACTTGGT CATCATATCA CCACAGTCAC TCACTAACGT TGGTGGTGGT GGCCACACTT
1428  GGTGGTGACA GGGGAGGAGT AGTGATAATG TTCCCATTTC ATAGTAGGAA GACAACCAAG
1488  TCTTCAACAT AAATTTGATT ATCCTTTTAA GAGATGGATT CAGCCTATGC CAATCACTTG
1548  AGTTAAACTC TGAAACCAAG AGATGATCTT GAGAACTAAC ATATGTCTAC CCCTTTTGAG
1608  TAGAATAGTT TTTTGCTACC TGGGGTGAAG CTTATAACAA CAAGACATAG ATGATATAAA
1668  CAAAAAGATG AATTGAGACT TGAAAGAAAA CCATTCACTT GCTGTTTGAC CTTGACAAGT
1728  CATTTTACCC GCTTTGGACC TCATCTGAAA AATAAAGGGC TGAGCTGGAT GATCTCTGAG
1788  ATTCCAGCAT CCTGCAACCT CCAGTTCTGA AATATTTTCA GTTGTAGCTA AGGGCATTTG
1848  GGCAGCAAAT GGTCATTTTT CAGACTCATC CTTACAAAGA GCCATGTTAT ATTCCTGCTG
1908  TCCCTTCTGT TTTATATGAT GCTCAGTAGC CTTCCTAGGT GCCCAGCCAT CAGCCTAGCT
1968  AGGTCAGTTG TGCAGGTTGG AGGCAGCCAC TTTTCTCTGG CTTTATTTTA TTCCAGTTTG
2028  TGATAGCCTC CCCTAGCCTC ATAATCCAGT CCTCAATCTT GTTAAAAACA TATTTCTTTA
2088  GAAGTTTTAA GACTGGCATA ACTTCTTGGC TGCAGCTGTG GGAGGAGCCC ATTGGCTTGT
2148  CTGCCTGGCC TTTGCCCCCC ATTGCCTCTT CCAGCAGCTT GGCTCTGCTC CAGGCAGGAA
2208  ATTCTCTCCT GCTCAACTTT CTTTTGTGCA CTTACAGGTC TCTTTAACTG TCTTTCAAGC
2268  CTTTGAACCA TTATCAGCCT TAAGGCAACC TCAGTGAAGC CTTAATACGG AGCTTCTCTG
2328  AATAAGAGGA AAGTGGTAAC ATTTCACAAA AAGTACTCTC ACAGGATTTG CAGAATGCCT
2388  ATGAGACAGT GTTATGAAAA AGGAAAAAAA AGAACAGTGT AGAAAAATTG AATACTTGCT
2448  GAGTGAGCAT AGGTGAATGG AAAATGTTAT GGTCATCTGC ATGAAAAGC AAATCATAGT
2508  GTGACAGCAT TAGGGATACA AAAAGATATA GAGAAGGTAT ACATGTATGG TGTAGGTGGG
2568  GCATGTACAA AAAGATGACA AGTAGAATCG GGATTTATTC TAAAGAATAG CCTGTAAGGT
2628  GTCCAGAAGC CACATTCTAG TCTTGAGTCT GCCTCTACCT GCTGTGTGCC CTTGAGTACA
2688  CCCTTAACCT CCTTGAGCTT CAGAGAGGGA TAATCTTTTT ATTTTATTTT ATTTTATTTT
2748  GTTTTGTTTT GTTTTGTTTT GTTTTATGAG ACAGAGTCTC ACTCTGTTGC CCAGGCTGGA
2808  GTGCAGTGGT ACAATCTTGG CTTACTGCAT CCTCCACCTC CTGAGTTCAA GCGATTCTCC
2868  TTCCTCAGTC TCCTGAATAG CTAGGATTAC AGGTGCACCC CACCACACCC AGCTAATTTT
2928  TGTATTTTTA GTAGAGAAGG GGTTTCGCCA TGTTGGCCAG GCTGGTTTTG AAGTCCTGAC
2988  CTAAATGATT CATCCACCTC GGCTTCCCAA AGTGCTGGGA TTACAGGCAT GAGCCACCAC
3048  GCCTGGCCCA GAGAGGGATG ATCTTTAGAA GCTCGGGATT CTTTCAAGCC CTTTCCTCCT
3108  CTCTGAGCTT TCTACTCTCT GATGTCAAAG CATGGTTCCT GGCAGGACCA CCTCACCAGG
3168  CTCCCTCCCT CGCTCTCTCC GCAGTGCTCC TTCCAGGACC TGGACCTCTG CCCTCTGGAT
3228  GGCGGCATCC AGCTACGAAT CTCCGACCAC CACTACAGCA AGGGCTTCAG GCAGGCCGCG
3288  TCAGTTGTTG TGGCCATGGA CAAGCTGAGG AAGATGCTGG TTCCCTGCCC ACAGACCTTC
3348  CAGGAGAATG ACCTGAGCAC CTTCTTTCCC TTCATCTTTG AAGAAGGTAG TTAGCCAAGA
3408  GCAGGCAGTA GATCTCCACT TGTGTCCTCT TGGAAGTCAT CAAGCCCCAG CCAACTCAAT
3468  TCCCCCAGAG CCAAAGCCCT TTAAAGGTAG AAGGCCCAGC GGGGAGACAA AACAAAGAAG
3528  GCTGGAAACC AAAGCAATCA TCTCTTTAGT GGAAACTATT CTTAAAGAAG ATCTTGATGG
3588  CTACTGACAT TTGCAACTCC CTCACTCTTT CTCAGGGGCC TTTCACTTAC ATTGTCACCA
3648  GAGGTTCGTA ACCTCCCTGT GGGCTAGTGT TATGACCATC ACCATTTTAC CTAAGTAGCT
3708  CTGTTGCTCG GCCACAGTGA GCAGTAATAG ACCTGAAGCT GGAACCCATG TCTAATAGTG
3768  TCAGGTCCAG TGTTCTTAGC CACCCCACTC CCAGCTTCAT CCCTACTGGT GTTGTCATCA
3828  GACTTTGACC GTATATGCTC AGGTGTCCTC CAAGAAATCA AATTTTGCCA CCTCGCCTCA
3888  CGAGGCCTGC CCTTCTGATT TTATACCTAA ACAACATGTG CTCCACATTT CAGAACCTAT
3948  CTTCTTCGAC ACATGGGATA ACGAGGCTTA TGTGCACGAT GCACCTGTAC GATCACTGAA
4008  CTGCACGCTC CGGGACTCAC AGCAAAAAAG CTTGGTGATG TCTGGTCCAT ATGAACTGAA
4068  AGCTCTCCAC CTCCAGGGAC AGGATATGGA GCAACAAGGT AAATGGAAAC ATCCTGGTTT
4128  CCCTGCCTGG CCTCCTGGCA GCTTGCTAAT TCTCCATGTT TTAAACAAAG TAGAAAGTTA
4188  ATTTAAGGCA AATGATCAAC ACAAGTGAAA AAAATATTA AAAGGAATA TACAAACTTT
```

FIGURE 2B

```
4248 GGTCCTAGAA ATGGCACATT TGATTGCACT GGCCAGTGCA TTTGTTAACA GGAGTGTGAC
4308 CCTGAGAAAT TAGACGGCTC AAGCACTCCC AGGACCATGT CCACCCAAGT CTCTTGGGCA
4368 TAGTGCAGTG TCAATTCTTC CACAATATGG GGTCATTTGA TGGACATGGC CTAACTGCCT
4428 GTGGGTTCTC TCTTCCTGTT GTTGAGGCTG AAACAAGAGT GCTGGAGCGA TAATGTGTCC
4488 ATCCCCCTCC CCAGTCTTCC CCCCTTGCCC CAACATCCGT CCCACCCAAT GCCAGGTGGT
4548 TCCTTGTAGG GAAATTTTAC CGCCCAGCAG GAACTTATAT CTCTCCGCTG TAACGGGCAA
4608 AAGTTTCAAG TGCGGTGAAC CCATCATTAG CTGTGGTGAT CTGCCTGGCA TCGTGCCACA
4668 GTAGCCAAAG CCTCTGCACA GGAGTGTGGG CAACTAAGGC TGCTGACTTT GAAGGACAGC
4728 CTCACTCAGG GGGAAGCTAT TTGCTCTCAG CCAGGCCAAG AAAATCCTGT TTCTTTGGAA
4788 TCGGGTAGTA AGAGTGATCC CAGGGCCTCC AATTGACACT GCTGTGACTG AGGAAGATCA
4848 AAATGAGTGT CTCTCTTTGG AGCCACTTTC CCAGCTCAGC CTCTCCTCTC CCAGTTTCTT
4908 CCCATGGGCT ACTCTCTGTT CCTGAAACAG TTCTGGTGCC TGATTTCTGG CAGAAGTACA
4968 GCTTCACCTC TTTCCTTTCC TTCCACATTG ATCAAGTTGT TCCGCTCCTG TGGATGGGCA
5028 CATTGCCAGC CAGTGACACA ATGGCTTCCT TCCTTCCTTC CTTCAGCATT TAAAATGTAG
5088 ACCCTCTTTC ATTCTCCGTT CCTACTGCTA TGAGGCTCTG AGAAACCCTC AGGCCTTTGA
5148 GGGGAAACCC TAAATCAACA AAATGACCCT GCTATTGTCT GTGAGAAGTC AAGTTATCCT
5208 GTGTCTTAGG CCAAGGAACC TCACTGTGGG TTCCACAGA GGCTACCAAT TACATGTATC
5268 CTACTCTCGG GGCTAGGGGT TGGGGTGACC CTGCATGCTG TGTCCCTAAC CACAAGACCC
5328 CCTTCTTTCT TCAGTGGTGT TCTCCATGTC CTTTGTACAA GGAGAAGAAA GTAATGACAA
5388 AATACCTGTG GCCTTGGGCC TCAAGGAAAA GAATCTGTAC CTGTCCTGCG TGTTGAAAGA
5448 TGATAAGCCC ACTCTACAGC TGGAGGTAAG TGAATGCTAT GGAATGAAGC CCTTCTCAGC
5508 CTCCTGCTAC CACTTATTCC CAGACAATTC ACCTTCTCCC CGCCCCATC CCTAGGAAAA
5568 GCTGGGAACA GGTCTATTTG ACAAGTTTTG CATTAATGTA AATAAATTTA ACATAATTTT
5628 TAACTGCGTG CAACCTTCAA TCCTGCTGCA GAAAATTAAA TCATTTTGCC GATGTTATTA
5688 TGTCCTACCA TAGTTACAAC CCCAACAGAT TATATATTGT TAGGGCTGCT CTCATTTGAT
5748 AGACACCTTG GGAAATAGAT GACTTAAAGG GTCCCATTAT CACGTCCACT CCACTCCCAA
5808 AATCACCACC ACTATCACCT CCAGCTTTCT CAGCAAAAGC TTCATTTCCA AGTTGATGTC
5868 ATTCTAGGAC CATAAGGAAA AATACAATAA AAAGCCCTG GAAACTAGGT ACTTCAAGAA
5928 GCTCTAGCTT AATTTTCACC CCCCCAAAAA AAAAAAATTC TCACCTACAT TATGCTCCTC
5988 AGCATTTGGC ACTAAGTTTT AGAAAAGAAG AAGGGCTCTT TTAATAATCA CACAGAAAGT
6048 TGGGGGCCCA GTTACAACTC AGGAGTCTGG CTCCTGATCA TGTGACCTGC TCGTCAGTTT
6108 CCTTTCTGGC CAACCCAAAG AACATCTTTC CCATAGGCAT CTTTGTCCCT TGCCCCACAA
6168 AAATTCTTCT TTCTCTTTCG CTGCAGAGTG TAGATCCCAA AAATTACCCA AGAAGAAGA
6228 TGGAAAAGCG ATTTGTCTTC AACAAGATAG AAATCAATAA CAAGCTGGAA TTTGAGTCTG
6288 CCCAGTTCCC CAACTGGTAC ATCAGCACCT CTCAAGCAGA AAACATGCCC GTCTTCCTGG
6348 GAGGGACCAA AGGCGGCCAG GATATAACTG ACTTCACCAT GCAATTTGTG TCTTCCTAAA
6408 GAGAGCTGTA CCCAGAGAGT CCTGTGCTGA ATGTGGACTC AATCCCTAGG GCTGGCAGAA
6468 AGGGAACAGA AAGGTTTTTG AGTACGGCTA TAGCCTGGAC TTTCCTGTTG TCTACACCAA
6528 TGCCCAACTG CCTGCCTTAG GGTAGTGCTA AGAGGATCTC CTGTCCATCA GCCAGGACAG
6588 TCAGCTCTCT CCTTTCAGGG CCAATCCCCA GCCCTTTTGT TGAGCCAGGC CTCTCTCACC
6648 TCTCCTACTC ACTTAAAGCC CGCCTGACAG AAACCACGGC CACATTTGGT TCTAAGAAAC
6708 CCTCTGTCAT TCGCTCCCAC ATTCTGATGA GCAACCGCTT CCCTATTTAT TTATTTATTT
6768 GTTTGTTTGT TTTGATTCAT TGGTCTAATT TATTCAAAGG GGGCAAGAAG TAGCAGTGTC
6828 TGTAAAAGAG CCTAGTTTTT AATAGCTATG GAATCAATTC AATTTGGACT GGTGTGCTCT
6888 CTTTAAATCA AGTCCTTTAA TTAAGACTGA AAATATATAA GCTCAGATTA TTTAAATGGG
6948 AATATTTATA AATGAGCAAA TATCATACTG TTCAATGGTT CTGAAATAAA CTTCACTGAA
7008 GAAAAAAAAA AAAGGGTCTC TCCTGATCAT TGACTGTCTG GATTGACACT GACAGTAAGC
7068 AAACAGGCTG TGAGAGTTCT TGGGACTAAG CCCACTCCTC ATTGCTGAGT GCTGCAAGTA
7128 CCTAGAAATA TCCTTGGCCA CCGAAGACTA TCCTCCTCAC CCATCCCCTT TATTTCGTTG
7188 TTCAACAGAA GGATATTCAG TGCACATCTG GAACAGGATC AGCTGAAGCA CTGCAGGGAG
7248 TCAGGACTGG TAGTAACAGC TACCATGATT TATCTATCAA TGCACCAAAC ATCTGTTGAG
7308 CAAGCGCTAT GTACTAGGAG CTGGGAGTAC AGAGATGAGA ACAGTCACAA GTCCCTCCTC
7368 AGATAGGAGA GGCAGCTAGT TATAAGCAGA ACAAGGTAAC ATGACAAGTA GAGTAAGATA
```

FIGURE 2C

```
7428 GAAGAACGAA GAGGAGTAGC CAGGAAGGAG GGAGGAGAAC GACATAAGAA TCAAGCCTAA
7488 AGGGATAAAC AGAAGATTTC CACACATGGG CTGGGCCAAT TGGGTGTCGG TTACGCCTGT
7548 AATCCCAGCA CTTTGGGTGG CAGGGGCAGA AAGATCGCTT GAGCCCAGGA GTTCAAGACC
7608 AGCCTGGGCA ACATAGTGAG ACTCCCATCT CTACAAAAAA TAAATAAATA AATAAAACAA
7668 TCAGCCAGGC ATGCTGGCAT GCACCTGTAG TCCTAGCTAC TTGGGAAGCT GACACTGGAG
7728 GATTGCTTGA GCCCAGAAGT TCAAGACTGC AGTGAGCTTA TCCGTTGACC TGCAGGTCGA
7788 C
```

FIGURE 2D

FIGURE 3A  DNA Sequence of the human IL-1RN gene. (GenBank Accession No. X64532)

```
-5988  GTCGACCTGC AGGTCAACGG ATCTGAGAGG AGAGTAGCTT CTTGTAGATA ACAGTTGGAT
-5928  TATATACCAT GTCCTGATCC CCTTCATCAT CCAGGAGAGC AGAGGTGGTC ACCCTGATAG
-5868  CAGCAAGCCT GGGGGCTGCA GCTTGGTGGG TAGAGGTACT CAGGGGTACA GATGTCTCCA
-5808  AACCTGTCCT GCTGCCTTAG GGAGCTTCTA ATAAGTTGAT GGATTTGGTT AAAATTAACT
-5748  TGGCTACTTG GCAGGACTGG GTCAGTGAGG ACCAACAAAA AGAAGCATC AGATTATACC
-5688  CTGGGGGTTT GTATTTCTTG TGTTTCTTTC TCTTCTTTGT ACTAAAATAT TTACCCATGA
-5628  CTGGGAAAGA GCAACTGGAG TCTTTGTAGC ATTATCTTAG CAAAAATTTA CAAAGTTTGG
-5568  AAAACAAATAT TGCCCATATT GTGTGGTGTG TCCTGTGACA CTCAGGATTC AAGTGTTGGC
-5508  CGAAGCCACT AAATGTGAGA TGAAGCCATT ACAAGGCAGT GTGCACATCT GTCCACCCAA
-5448  GCTGGATGCC AACATTTCAC AAATAGTGCT TGCGTGACAC AAATGCAGTT CCAGGAGGCC
-5388  CAAATGAAAA TGTTTGTACT GAAATTTGTT AAAGCTTCCC GACAAACTAG ATTTATCAGT
-5328  AAGGATTGTT TTCTGCAAGG GGGATGAAAC TTGTGGGGTG AGCCATTTGG GCTGAGGAGG
-5268  AGGGAGGTTG GAGCTGAGAA ATGTGGAGAC AATTTCCCTT TAGAAGGACT GAATCTCCCT
-5208  GCCTCTCTGG GGTGCGGCAG CCAGCAGGAT CCAATGGTGT ATATGTCTCC CCAGCTCCCC
-5148  ATTCAGTGAT ATCATGTCAG TAGCTTGAAA TTATCCGTGG TGGGAGTATT ATGTCATGGA
-5088  AATTGGCAAA TGGAAACTTT TATTGGAGAT TCAATTGTTA AACTTTTACC AGCACAACAC
-5028  TGCCCTGCCT TCAGAGTCAA TGACCCTATC CAAGTTTAAT CCATCTGTCC ACTGTCTCCA
-4968  ACACGATCTT TATAAAACAC ACCTGACAAC ATTACCCTTT TATTCAGTTT TTTAAAAGAT
-4908  AAGTTTCCAG CTCATCGGGG TGGCTTTAAA GGCCATTTCT CCTCTGGACC TCACCCAACT
-4848  TTTCAAATCA CTTTTCCTAC CCCTACCTCT AAATGCTACT CAAACTCCAG CCATCCTGAA
-4788  TAATAAGACT TTTGAAAAGT AGATTATGGG CTGGCACAG TGGCTCACAC CTGTAATCCC
-4728  AGCACTTTGG GAGGCCAAGA TGGGTGGATC ACCTGAGGTC GGGAGTTCGA GACCAGCCTG
-4668  ACTAACATAG TGAAACCCTG TCTCTACTAA AAATACAAAA TTAGTTGGGG GTGGTGGCAC
-4608  AAGCCTGTAA TCCCAGCTAC TCAGGAGGTT GAGGCAGGGG AATTGCTTGA ACCTGGGAGG
-4548  CGGAGGTTGC GGTGAGCCTA GATTGCTCCA CTGCACTCCA GCCTGGGCAA CAAGAGCGAA
-4488  ACTCCATCTC AAAAAAATAA ATAAATAAAT AAAGTAGATT ACATCAGATA CCTCTGGCCT
-4428  AGGTTGTTTA TGACCAACTC TCCTGCTGAG AATAACTAGA AAAGCTAGAC AAAACATATT
-4368  TCCAAAAGAT CTCTTTGGAG GCATCAGAGA ATGGCCAAGG CTGTAAGGAA CTGCCTGAGC
-4308  CCAGAGAGGT GGAGCCCAGC ACTGGTGCCC TTTACTCCTG GGGACATGTG CTGGTTTCAA
-4248  AAACTTCAGC TGAGCTTTTG AGCATTCATG GAACTTGGTG GGGGAGATGA AATTTGTACC
-4188  TTAAATCCTG CCTACAGGGA GGGTCCCTGA TAATCCCCAC CCAATTTGGA AATCTGGGTC
-4128  AGCCTTCACA GGTACTGAAG CCCTCCTCTG AATGATCTCA AGTCCTGCTA GGGTAGAGGT
-4068  TACCTGCTTT TGAAAGGCTC CTGGCCTACC TGTGCAGCAG GAGCAAAAGT GAACCATCTC
-4008  AGGGTACAGA TAACAATCAT CCAGAGCCTT GAATGACCTC TACTGTGCTT AATATATAGT
-3948  ATTCAGCAGT CAGTAAAAAG GATTTAGGCA CATGCAAGAT GACCTGTGTA TCAGGGAGAA
-3888  ATAGGCAATA AATTGAGATC CAGCAGGGAT TTGAATCATG GATTTGAATC AGGGGCAGCC
-3828  TTCGAAAGAA CTATGGAGAA TATACTCAGA TTTAAAACAT AAGATTGGAA TTTTTGGCAG
-3768  AGAACTAACA ACTGTACAAA AAAGGAACCA AATGGAAATC CTAGAACTGA AAGATGCAAT
-3708  TAACCGATGT TGAGAAATAG CCAACATCTA TTGAACACTT CCCATGTGGA CAGCTGTGCT
-3648  AAACACTTTA CAGGCATCAA CATAAGATGT GTCCCCTTAC AGCAGTGCAG TGTCCCTCCT
-3588  AAGACATGGA CAGCCTGGTT TCCCTATCTC TCTGCTTCAT CAAAACCCCT TTACGTGGGG
-3528  CTTAGACACT CCTGTTGTCT CTAGTGTCTA GTAGCACAGG GCTCAGCACA TGGAAGCCAC
-3468  TAGATACAAT TTGATGACCA GGACCTCCGA TGAAAGCCAT GGGTGCTGAT TGGGAAGGCA
-3408  TTGTCTTTTA TGTGCTATGG TCTTAAAGCT TCATCCAGGA AGCAGAACTC GGGGGGTGCT
-3348  GAGGACCCAG AACCGAGAAT AAGATTAGTC AGAGATTTCC TGTGGGCAGA AATCATAAGG
-3288  ACGCCAACTG TTTGGGTGAG ATAAGACGAA ACCAAGAGTG GACTTGTGGC CAGAAGCGTG
-3228  AGGAAGAGGG AGAGAGCTTC CCTTGTCCCC TTTCTTCCTC TCCCTAAGCC ACAGTGATTG
-3168  ACAGCCCCCC CGCTTTGGAG TCAGAGCAGG CTTGAGACTG GACTGGGAAA GGAGGGTGGG
-3108  TCAGGATACA GAGCAGGAAG GCTGGGAGTG CAGGGCAGGA GCAAGGGGCT GGGGCATTCA
-3048  TTGTGCCTGA TCTCTCCCAC TTTACCTGGG GTAAAGAAGC ATATGCAAAA GCCACGGTGT
```

```
-2988 GAGTATTTCC CAAGTGCCAG GGTCAGGGCA TGATTCATCA CGTGCAGCAT TTCATTCAAT
-2928 CCTTATAGTA ACCGATGATG TGGCTTCTAT TATTAGCTCT ATCAGATAAT GAAACTGAGA
-2868 CCAAGACAGG CTCTGCACAT TGTGTGGGGT AATGACACAG GGGGATTCAG ACCTAGACTC
-2808 CATAACTCCT GCCCCAGGGA CCACCCCCAC CCTCACCCTG TGCATGTCGA CAAAGGACAG
-2748 ACTGGGCCAC TTCTCAGGAC ACAGCGGGGA AATGACACAG AGCAGGGAGG TTCCAGGAGC
-2688 CCCGAGCGTC TTTTCTCCAG GAGAATACTC TCTGAATTCA GACTGGGGTC AGAGAAACAT
-2628 TTACCCAGGA GCCGCAGTGT GGGTGGGGCT TTTTACTTGA AACGCTGTCT GAAGGCAGTG
-2568 GCAGGATGAA CTCTCCACCC TACCTTGGCA AGCCACTTCT CTTCTGCAAT CTGTAAGGAC
-2508 ATTGTTGAGA GAATTATGGT CTTCCAATTC GGAGGGTTG AAGAAAGACA AATAGGAGAG
-2448 AACCTATCAT AGTCAGGTGC TAGCTGCCTT CTCTTTCAGA GAGTGTGAGA ATAAAGTGAT
-2388 ACACTTGATT ATTAGCAAAT ACTTTGGAAA TTTTAAACGC TAATATTCAA CACACTCTGG
-2328 AAGAGGCAAA TAAGTAGACA GGTTCATATA CATCATCTCC TTCAGCTAGT CCTCACAAAA
-2268 ACAAACAAAT GAATAAACAA AATTCTTCTT TGGCCCTCAT AGGAAGACAC TGTTTCTTGA
-2208 ACGTGTTTCA AAAAGGATGG GTGACTCACT CAAGGTCACA CTGTTTATGA GGACAGTACA
-2148 GGAATACAGA CATGCCATTT TGCCTGAAAA AATCCATCAC CCAGGGAGGT GACACAATTT
-2088 TGCAGAAATG TTCTATTTCC TCTGAAGGAT ACATTCTTTA AACCTTGGG AAATTCATTC
-2028 ATAGTCTTCC TCCTTTGAAG GATTACTCTC TGGACACAAA GTGTTTGATT CTGATTTGTT
-1968 GGTTGGAAGA TGTGTTGGTT GAGAGAAAGA TTCTGATTTG TTGGTTGAAA ATAGACTCAT
-1908 CAAGATCAAC TGCTGTAGTA GTAAATATTT TGACATTTTG TCTGTATTCC TGTGCTGCCC
-1848 TCACAAGCTG CATCACCTTG AGTGAGTCAT TCATACTTTT TTGTTTGTTT TTGTTTTGGA
-1788 GATGGAGTCT TACTCTGTTG CCTAGGCTGG AGTGCGGTGG CGTGATCTTG GCTCACTGCG
-1728 ACCTCCATCT CCTGGGTTCA AGTGATCCTC CTGCCTCAGC CTCCCGAGTA GCTGGGATTA
-1668 CAGGCACATG CCACCATCCC TGCTAATTTT TGCATTTTCA GTAGAGACGG AGTTTCACCA
-1608 TGTTGGTCAG GTTGGTCTTG AACTCCTGAC CTCAGGTGAT CCGCCCACCT CAGCCTCCCC
-1548 AAGTGCTGGG ATTACAGGTG TGAGCCACCG TGCCCAGCCC AGCCATCATT TTTGAAACAC
-1488 GTTTGAGAAA TAGTGTCTTC CTTTGAGGGC CAAGGAGACA TTTTTTTTGT TTATTTGTTT
-1428 GTTTTTGTGA GGACTAGCTG AAGGGGGTGA TGTATATTAA CCTGCCTACT TATTTGCCTC
-1368 TTCCCAGAGT GTGATGAATA TTAGGGTTTA AGTTTCTGA AGCATTTGTT AATAAAGCCC
-1308 GGGGCTGGAG GTCAGAAGAC CTGGATTTCT CTGCATACTT TTGCCATCAG CAAGCTGTGT
-1248 GACCTTGGAC AGATCCCTTT TTTGTCTAAA TCTTTCTGAG TCTTCTTGAA AACAATGCCA
-1188 GGTTGGGACA GGATGATTGC CAAGCTCCCG TCCAGCTCTA AAACACTGCA ACGTATGCTT
-1128 CTGCACCAGC ACTGTCCATC CTGTAGATCA TGCAGAAATT CTCTTCAACT TTTTCCTACC
-1068 CATAAAATAG GAGCATGCTT ACCTTTTCC TAATGTTCCA GGCCCCGGGT CTAGATATTG
-1008 TAAGTAAGGA AGTTAATGTG TATCAGAGCC CATTATGGGC CAGAAGTTCT CCTCTTCCTT
 -948 CCTACACCTG CTTCCTCCCT CCCTCCCTCC CTCTTTCCCT TCCTTCCTTC CATCCATTTG
 -888 TGAAGAAGAC ATGATCACCC TCATTCTGAG AGTGAAGAGA CAGAGGCTCA ACTAATGAAA
 -828 TGATTTGTTC AAGGTCACAC GGGTGGCACA AGGCAAGTGG CAGAGGTTGA ATTTAGACCC
 -768 ATTCCTGTCC AAATGCTGAG TTTATGTCAT CGTCCCGAGA CCATAACTTT AAAGATGTAA
 -708 GATAGTGGGA AAAGAGTTGA TTTCAAAGCA CCTCTCAGAA GGACTCACTT TACATCAGGG
 -648 GTCAGCAGAC TCAGGCCAAA TCCGGTCCAT TCCCCGCTTT TGCAAAGAAA GTTGTAGTGG
 -588 AACACAGCTA GGCTTATTGA TTTATGGATT GCCAACGTCC TTTTGTGAAA CAGACAGCTG
 -528 AGCTGAGTAA TCGTGGCGCA CAAAACCTAA AATATTTACT ATCTCGTCCT TTACAGAATG
 -468 TTTGCCAATC TATGGTCCGG AGTCCAAGGC TGTCCATTTT TCAAAGAACA CAAAGTGACA
 -408 TGAGACTGTC CCATGTGCAG GGAGCCCTAT CATTTTATTA TGAAAAAACG GCCTTTCTGC
 -348 TCAAATCTGT TTTTTAAAAA GTCAACAAAC AGACTCTGGG TACCTGTCAG GAACAGTAGG
 -288 GAGTTTGGTT TCCATTGTGC TCTTCTTCCC AGGAACTCAA TGAAGGGGAA ATAGAAATCT
 -228 TAATTTTGGG GAAATTGCAC AGGGGAAAAA GGGGAGGGAA TCAGTTACAA CACTCCATTG
 -168 CGACACTTAG TGGGGTTGAA AGTGACAACA GCAAGGGTTT CTCTTTTTGG AAATGCGAGG
 -108 AGGGTATTTC CGCTTCTCGC AGTGGGGCAG GGTGGCAGAC GCCTAGCTTG GGTGAGTGAC
  -48 TATTTCTTTA TAAACCACAA CTCTGGGCCC GCAATGGCAG TCCACTGCTT GCTGCAGTCA
   13 CAGAATGGAA ATCTGCAGAG GCCTCCGCAG TCACCTAATC ACTCTCCTCC TCTTCCTGTT
   73 CCATTCAGAG ACGATCTGCC GACCCTCTGG GAGAAAATCC AGCAAGATGC AAGCCTTCAG
  133 GTAAGGCTAC CCCAAGGAGG AGAAGGTGAG GGTGGATCAG CTGGAGACTG GAAACATATC
```

FIGURE 3B

```
 193 ACAGCTGCCA GGGCTGCCAG GCCAGAGGGC CTGAGAACTG GGTTTGGGCT GGAGAGGATG
 253 TCCATTATTC AAGAAAGAGG CTGTTACATG CATGGGCTTC AGGACTTGTG TTTCAAAATA
 313 TCCCAGATGT GGATAGTGCG ACCGGAGGGC TGTCTTACTT TCCCAGAGAC TCAGGAACCC
 373 AGTGAGTAAT AGATGCATGC AAGGAGTGG GACTGCGATT CAGGCCTAGT TGAATGTGCT
 433 GACAGAGAAG CAGAGAGGGG CACCAGGGGC ACAGCCCGAA GGCCCAGACT GATATGGGCA
 493 AGGCCTGTCT GTGCTGACAT GTCGGAGGGT CCCACTCTCC AGGGACCTTG GTTTCCCCGT
 553 CTGTGACATC TGTGACATGA GAGTCACGAT AACTCCTTGT GTGCCTTACA GGGTTGTTGT
 613 GAAAATTAAA TGCACAGATA ATAGCGTAAC AGTATTCCGT GCATTGTAAA GAGCCTGAAA
 673 ACCATTATGA TTTGAAAATG GAATCGGCTT TGTGAGACCA TCACTATTGT AAAGATGTGA
 733 TGCTGATAGA AATGACAGGA CTGCTTGTGC ATGCCCTCTG CAGTGTGACA TTCCAGCAGT
 793 GAAATCATGT TGGGGTGACT TCTCCCCCAC TCTGACCTTT ATGTTTGTCT GGGCCGAGGC
 853 TGCAAGTCGG GCTCTGTGGG TGTATGAGTG ACAAGTCTCT CCCTTCCAGA TATGGGGACT
 913 GTCTGCTTCC CTAGGTTGCC TCTCCCTGCT CTGATCAGCT AGAAGCTCCA GGAGATCCTC
 973 CTGGAGGCCC CAGCAGGTGA TGTTTATCCC TCCAGACTGA GGCTAAATCT AGAAACTAGG
1033 ATAATCACAA ACAGGCCAAT GCTGCCATAT GCAAAGCACT TTGGTTTGCC TGGCCACCCC
1093 TCGTCGAGCA TGTGGGCTCT TCAGAGCACC TGATGAGGTG GGTACAGTTA GCCACACTTC
1153 ACAGGTGAAG AGGTGAGGCA CAGGTCCCAG GTCAGGCTGG CCGGAGCTCT GTTTATTACG
1213 TCTCACAGCT TTGAGTCCTG CTCTCAACCA GAGAGGCCCT TTACCAAGAA GAAAGGATTG
1273 GGACCCAGAA TCAGGTCACT GGCTGAGGTA GAGAGGAAGC CGGGTTGTTC CAAGGGTAG
1333 CTGCTCCTGC AGGACTCTGA GCAGGTCACC AGCTAATGGA GGAAAGGCTC TAGGGAAAGA
1393 CCCTTCTGGT CTCAGACTCA GAGCGAGTTA GCTGCAAGGT GTTCCGTCTC TTGAAACTTC
1453 TACCTAGGTG CTATGGTAGC CACTAGTCTC AGGTGGCTAT TTAAATTTAT ACTTAAATGA
1513 ATGAAAATAG AAGAAAATTT AAAATCCAGA CCCTTGGTCA CACTATCCAC ATTTAAAGAG
1573 GTCAATAGCC ACATGTGGTT AGTGGCCACC CTATTGGGCA GTGCAGCTAC AGAACATTTT
1633 TGCATCCCAG AAAGTTCTTT TGGATGTTGC TGCTCTACAG CATGCTTTGC TGAAACAGAA
1693 GTGCCTTCCC TGGGAATCTC AGATGGGAAG CAAGTAAGGA GGGGAGTCAA ATGTGGGCTC
1753 ACTGCTCACC AGCTGTGAGG GTTGGGCCTG CCTCTTAACC ATTGTCAGCC TCAGTCTTCT
1813 CATCCATGCA TGCCGTGGGT ATACTAAAAT ACTATACCCC TGGAAGAGCT GGATGCAAAT
1873 TTGACAAGTT CTGGGGGACA CAGGAAGGTG CCAAGCACAA GGCTGGGCAC ATGGTGGCTG
1933 TGCACTACAG CTGAGTCCTT TTCCTTTTCA GAATCTGGGA TGTTAACCAG AAGACCTTCT
1993 ATCTGAGGAA CAACCAACTA GTTGCTGGAT ACTTGCAAGG ACCAAATGTC AATTTAGAAG
2053 GTGAGTGGTT GCCAGGAAAG CCAATGTATC TGGGCATCAC GTCACTTTGC CCGTCTGTCT
2113 GCAGCAGCAT GGCCTGCCTG CACAAACCCT AGGTGCAATG TCCTAATCCT TGTTGGGTCT
2173 TTGTATTCAA GTTTGAAGCT GGGAGGGCCT GGCTACTGAA GGGCACATAT GAGGGTAGCC
2233 TGAAGAGGGT GTGGAGAGGT AGAGTCTAGG TCAGAGGTCA GTGCCTATAG CAAGTGGTC
2293 CCAGGGCCAC AGCTGGGAAG GGCAAATACC AGAAGGCAAG GTTGACCATT CCCTTCCTCA
2353 AGTGCCTATT AAGGCTCCAT GTTCCTATGT TGTTCAAACC CTAACTCAAT CCCAAATTAA
2413 TCCACCATGT ATAAGGTTGA GCTATGTCTC TTATTCCTGG ACACCATACT CAGCCATATC
2473 TGGTCCACAC ATTAACAGCT GGATGACCTT GAAGAAGCTT CACCCACTCT GTTCCTCAGC
2533 TTTCCCTTCA GTGGGATGAT ATCAACTGGA CAACAGGATG TGCGATTCTT TTAGTTCCAG
2593 CCTTCCAGGA TGTTTTCACT CCCCTGTTTG TTGTTGTAGG ATGGTATTAC CTCCACCTTC
2653 CCACCTTCCC TATGCCCTGG TTCTGTCTCC TGTGCCTCGC TCTGAAAGTG GATGAGACCT
2713 ACAATTCCTG TCCTGGTAGT TCTCCTAATG AACACACTGA AGCACGAGGA AGCTGAGATT
2773 TTTGTTGCTA CATGAGAGCA TGGAGGCCTC TTAGGGAGAG AGGAGGTTCA GAGACTCCTA
2833 GGCTCCTGGT GGAGCCCCAC TCATGGCCTT GTTCATTTTC CCTGCCCCTC AGCAACACTC
2893 CTATTGACCT GGAGCACAGG TATCCTGGGG AAAGTGAGGG AAATATGGAC ATCACATGGA
2953 ACAACATCCA GGAGACTCAG GCCTCTAGGA GTAACTGGGT AGTGTGCATC CTGGGGAAAG
3013 TGAGGGAAAT ATGGACATCA CATGGAACAA CATCCAGGAG ACTCAGGCCT CTAGGAGTAA
3073 CTGGGTAGTG TGCATCCTGG GGAAAGTGAG GGAAATATGG ACATCACATG GAACAACATC
3133 CAGGAGACTC AGGCCTCTAG GAGTAACTGG GTAGTGTGCA TCCTGGGGAA AGTGAGGGAA
3193 ATATGGACAT CACATGGAAC AACATCCAGG AGACTCAGGC CTCTAGGAGT AACTGGGTAG
3253 TGTGCTTGGT TTAATCTTCT ATTTACCTGC AGACCAGGAA GATGAGACCT CTCTGCCCTT
3313 CTGACCTCGG GATTTTAGTT TTGTGGGGAC CAGGGGAGAT AGAAAAATAC CCGGGGTCTC
```

FIGURE 3C

```
3373 TTCATTATTG CTGCTTCCTC TTCTATTAAC CTGACCCTCC CCTCTGTTCT TCCCCAGAAA
3433 AGATAGATGT GGTACCCATT GAGCCTCATG CTCTGTTCTT GGGAATCCAT GGAGGGAAGA
3493 TGTGCCTGTC CTGTGTCAAG TCTGGTGATG AGACCAGACT CCAGCTGGAG GTAAAAACAT
3553 GCTTTGGATC TCAAATCACC CCAAAACCCA GTGGCTTGAA ACAACCAAAA TTTTTTCTTA
3613 TGATTCTGTG GGTTGACCAG GATTAGCTGG GTAGTTCTGT TCCATGTGGT GGAACATGCT
3673 GGGGTCACTT TGGAAGCTGC ATTCAGCAGA GTGCCAGGCT TGCGCTGGGC ATCCAAGGTG
3733 GTCCCTCATC CTCCAGGCTC TCTTTCCATG TGATCTCTCA GTGTTTAAGA GTTAGTTGGA
3793 GCTTCCTTAC AGCATGGCGG CTGACTTCCA AAAGGGATTA TTCCAAAAAG AGCCTCAACA
3853 TGCAGGCGCT TATTATGACT TCTGCTTGCA TCATCCTATT GGCCAAAGCC AGTCACGTGG
3913 CTAAGTCTAG CCCCCTGTGA GAGGAGACTG CATAAGAGTG TGAACACCAG GAGACACGGT
3973 CACTGGGGGC CACCACTGTA ACCATCTACC ACAGGACCTG AATCTCTGTG TGCTACTCCC
4033 TTGCTCAAGG GCCCCCCTAC CCACGCAGAC CTGCTGTCTT CTAGCAAAGC CCATCCTCAG
4093 GACCTTTCTC TTCCAATCCT TATTGACTCA AATTGATTAG TTGGTGCTCC ACCCAGAGCC
4153 CTGTGCTCCT TTATCTCATG TAATGTTAAT GGGTTTCCCA GCCTGGGAA AACATGGCTT
4213 TGTCTCAGGG GCTTGCTGGA TGCAACCTTA ACCTCAATGT GAGTGGCCAT ACTGTGGCAC
4273 TGTCCCATCC CTCACCAGGG ACACTGTTCT GGAGGGTGAC TGCCTGTTCT GTGAGGAGTG
4333 GGGATGGCTA GGACATTGCA TGGAACACAC CACCACCCCA TCTTCTCAGA GCTCAAACCC
4393 TGACAGAACA CCAGCTCCAC AGGCCTTGGC TTCTGCTGAT GGTGCCGTGT ATTTACCAGA
4453 CTTAGTGGTC CAAGGCCAGA GTGGCAGATT TCCCAAAGTC AAGGTGTGAC AGTGGGACAG
4513 CCTCTTTGTG TCTTTGCTGT CCTAAGAAAC CTGGGCCAGG CCAGGCGCAG TGGCTCACGC
4573 CTTGTAATCC CAGCACTTTG AGAGGCCAAG GTGGGCAGAT CACGAGGTCA GGAGTTTGAG
4633 ACCAGCCTGG CCAACATTGG TGAAACCCTG TCTCTATTAA AAATAGAAAA CATTAGACAG
4693 GTGTGGTGGT GCATGCCTGT AATCCCAGCT ACTCAGGAGG CTGAGGCAGG AGAATCGCTT
4753 GAACCCAGGA GGTGGAGGTT GCAGTGAGCC GAGATTGTGC CACTGCACTC CAGCCTAGGC
4813 GACAGAGCAA GACTCCGTCT CGGGAAAATT AATTAATAAA TAAATAAACC TAGGTCCCAG
4873 AGTCCCACAG AATGGCAGAC AGGAGCACCT GGGGGCTTTT AGGGTATGGC ATTTCCCCTG
4933 TACTAACTCT GGGCTGTCCA GAGGCGATTT CATGGCGTGG AGTGGAGAGG GAGGCAGCAC
4993 AGGACTTCCT AGGCCTCAGC TCTCACCTGC CCATCTTTTG ATTTCCAGGC AGTTAACATC
5053 ACTGACCTGA GCGAGAACAG AAAGCAGGAC AAGCGCTTCG CCTTCATCCG CTCAGACAGT
5113 GGCCCCACCA CCAGTTTTGA GTCTGCCGCC TGCCCCGGTT GGTTCCTCTG CACAGCGATG
5173 GAAGCTGACC AGCCCGTCAG CCTCACCAAT ATGCCTGACG AAGGCGTCAT GGTCACCAAA
5233 TTCTACTTCC AGGAGGACGA GTAGTACTGC CCAGGCCTGC CTGTTCCCAT TCTTGCATGG
5293 CAAGGACTGC AGGGACTGCC AGTCCCCTG CCCCAGGGCT CCCGGCTATG GGGGCACTGA
5353 GGACCAGCCA TTGAGGGGTG GACCCTCAGA AGGCGTCACA ACAACCTGGT CACAGGACTC
5413 TGCCTCCTCT TCAACTGACC AGCCTCCATG CTGCCTCCAG AATGGTCTTT CTAATGTGTG
5473 AATCAGAGCA CAGCAGCCCC TGCACAAAGC CCTTCCATGT CGCCTCTGCA TTCAGGATCA
5533 AACCCCGACC ACCTGCCCAA CCTGCTCTCC TCTTGCCACT GCCTCTTCCT CCCTCATTCC
5593 ACCTTCCCAT GCCCTGGATC CATCAGGCCA CTTGATGACC CCCAACCAAG TGGCTCCCAC
5653 ACCCTGTTTT ACAAAAAAGA AAAGACCAGT CCATGAGGGA GGTTTTAAG GGTTTGTGGA
5713 AAATGAAAAT TAGGATTTCA TGATTTTTTT TTTTCAGTCC CCGTGAAGGA GAGCCCTTCA
5773 TTTGGAGATT ATGTTCTTTC GGGGAGAGGC TGAGGACTTA AAATATTCCT GCATTTGTGA
5833 AATGATGGTG AAAGTAAGTG GTAGCTTTTC CCTTCTTTTT CTTCTTTTTT TGTGATGTCC
5893 CAACTTGTAA AAATTAAAAG TTATGGTACT ATGTTAGCCC CATAATTTTT TTTTTCCTTT
5953 TAAAACACTT CCATAATCTG GACTCCTCTG TCCAGGCACT GCTGCCCAGC CTCCAAGCTC
6013 CATCTCCACT CCAGATTTTT TACAGCTGCC TGCAGTACTT TACCTCCTAT CAGAAGTTTC
6073 TCAGCTCCCA AGGCTCTGAG CAAATGTGGC TCCTGGGGGT TCTTTCTTCC TCTGCTGAAG
6133 GAATAAATTG CTCCTTGACA TTGTAGAGCT TCTGGCACTT GGAGACTTGT ATGAAAGATG
6193 GCTGTGCCTC TGCCTGTCTC CCCACCAGGC TGGGAGCTCT GCAGAGCAGG AAACATGACT
6253 CGTATATGTC TCAGGTCCCT GCAGGGCCAA GCACCTAGCC TCGCTCTTGG CAGGTACTCA
6313 GCGAATGAAT GCTGTATATG TTGGGTGCAA AGTTCCCTAC TTCCTGTGAC TTCAGCTCTG
6373 TTTTACAATA AAATCTTGAA AATGCCTATA TTGTTGACTA TGTCCTTGGC CTTGACAGGC
6433 TTTGGGTATA GAGTGCTGAG GAAACTGAAA GACCAATGTG TYTTYCTTAC CCCAGAGGCT
6493 GGCGCCTGGC CTCTTCTCTG AGAGTTCTTT TCTTCCTTCA GCCTCACTCT CCCTGGATAA
```

FIGURE 3D

6553 CATGAGAGCA AATCTCTCTG CGGGG

FIGURE 3E

Figure 4. DNA Sequence of human IL-13 gene. (GenBank Accession No. U31120)

```
   1 GGATCCCCGC TGACAATCTA GAAACAAGCA ACAGACCCTC TGATGTAGCC ATCTGTGCCG
  61 CGCCTCTCCG CACGGCCCGC CACGCCTTGG TCCCTGGAGA CCACCCTCCA GGGCAGGGGC
 121 TGCCGCTCGG CCGGGCCCGC GGGGTCCCTC GGCCTGACAT GGCCGGTGCT GGAGCGGCAC
 181 GTGCGCGCCT CGGCCCCTCG GCCGCTCCCG CCCCTCGCCG GTGCGCACCG GCGCTCGGGG
 241 AGCCGCTGGC CCGGGTGTCC AGCCGGCCCT TGCCCTGCCT GGCGCTCGGA CCGCCACCTT
 301 TGCCGCCCCC TCGCCAGCCT CCGCAGCTTC CAGACTGGCC GGTCTGCGCG CCCACCCCTG
 361 CCTCCCGGAC CGGCCACCGC CGGAGGCCGC GGAGGAGGGC CCGGCCGCGC AGATCCCGCT
 421 TATCGGGCCC CATCTCCCGT TACATAAGGC CACCCCCCTA TCTCCGCGGG CCATCGCCGC
 481 CGCAACCGCC GCGCCAGCGC TTCTCCCAC GCGCGGGGC GCCCCTGCCC ACCGCTCCCG
 541 GCAGGGCTTT TGGTGGCCAT GGGGGATAAG GGGCGTTGAC TCACCCGGGC GGGGCTCCGG
 601 GAGTTGCACA GACCAAGGTA GTTCCCCGCT CCTTCCCCCA TCACGGAGAC CCTGTGGGAG
 661 ATGCCGTGGG CCCTCTACTA CAGATTAGGA AACAGGCCCG TAGAGGGGTC GCGCGGCCAA
 721 GTAGCGGCAC TCCAGGCACT GGGGGCCCTC GAGGGAAGGG GCAGACTTCT GGGAGTCAGA
 781 GCCAGCAGCT GGGCTGGGAA GCTTCGAGTG TGGACAGAGA GGGTGGGAAT GACGTTCCCT
 841 GTGGGAAGAG AGGGTGGGCA AGCCTGGGAT GCCTCTGAGC GGGAATCCAG CATGCCTTGT
 901 GAGGAGGGTC ACAAGCACAC CCTTGTGAGG AGGTTGAGCC CCATCGAGGA CAGGACGGAG
 961 GGAGCCTGAG CAGGCAGAGA GGGGGCCTGG GGAGGCGCTG GTTCGGGGAG GAAGTGGGTA
1021 GGGGAGAAAT CTTGACATCA ACACCCAACA GGCAAATGCC GTGGCCTCTG CTGTGGGGT
1081 TTCTGGAGGA CTTCTAGGAA AACGAGGGAA GAGCAGGAAA AGGCGACATG GCTGTAGGGC
1141 CAAGCCCAGG AGCCGCCCTC CACAGCACTC ATTCTGCAGA AGGGAAATTT GAGGCCCCCA
1201 GACGGCAGGG GTTGATCCTG CAGAGACTGG TGAGCAAAGG GGATCACCCC AAGCCCCAGT
1261 GGCACTAGGA ACACTTACAA TCTCTGACCT GGACTAAGGC TGCCAGCCTG GCCCAGTTAA
1321 GAGTTTCCCA AAGGATGGC CCATACACTT TAAATTAAAG GGGCCAGACA CGTGCACACT
1381 ACTTCCAGCC ACTCTGGAAG CTGAGGTGGG GGGATCGCTT GAGTCTGGGA GTTGGAGGCC
1441 AGCCTAGGCA GGCAACATAG TGAGACCCCA TCTCCAAAAA AACAAAACAA AACAAAACAA
1501 AAAAACACCA AAAAAGCTCC CAGAAAGACC TCTGAATCTT TCTGGATCTC TCAGTGGAGA
1561 CCTGGAAATC TGAACTTTGA CAATCCCTCT CACAGTGGGG CCAAGGAGGA ATTAGGCAAG
1621 CCAAAAGAAG TGAACTTTAC TCTTCTATTG CCTGTTTGAA TTTTGTATCC AAGCAAGTGT
1681 TACTTAAGTA ATTTAAGAGA CTGGTTCATC GAAAAAATAA AACTCCCCAA ATTCCCATAG
1741 CTGGTAGACT GTGGTCACAG CCACAGTGCA CTAAGACTAT CTGCTCAGCA CTTCTGGTGA
1801 CCCAAAAGGG TCTGAGGACA GGAGCTCAGA GTTGGGTCAG CTGTCCAGGT ACTCAGGGTT
1861 GTCACAGGCA AAACTGCTGG AACTCAGGGC AGCATTGCAA ATGCCACGCC GCTCTCAGGG
1921 CCCCTTGCCT GCCGCTGGAA TTAAACCCAC CCAGATCTTG GAAACTCTGC CCTGGACCCT
1981 TCTCAATAAG TCCATGAGAA ATCAAACTCT TTCCTTTATG CGACACTGGA TTTTCCACAA
2041 AGTAAAATCA AGATGAGTAA AGATGTGGTT TCTAGATAGT GCCTGAAAAA GCAGAGACCA
2101 TGGTGTCAGG CGTCACCACT TGGGCCTATA AAAGCTGCCA CAAGACGCCA AGGCCACAAG
2161 CCACCCAGCC TATGCATCCG CTCCTCAATC CTCTCCTGTT GGCACTGGGC CTCATGGCGC
2221 TTTTGTTGAC CACGGTCATT GCTCTCACTT GCCTTGGCGG CTTTGCCTCC CCAGGCCCTG
2281 TGCCTCCCTC TACAGCCCTC AGGGAGCTCA TTGAGGAGCT GGTCAACATC ACCCAGAACC
2341 AGAAGGTGAG TGTCGGCTAG CCAGGGTCCT AGCTATGAGG CTCCAGGGT GGGTGATTCC
2401 CAAGATGAGG TCATGAGCAG GCTGGGCCTG GTCCTAAGAT GCCTGTAGGT CAGGAAAAAT
2461 CTCCATGGAC CAAGGCCGG CCCAGCCATG AGGGAGAGAG GAGCTGGGCT GGGGGGCTCA
2521 GCACTGTGGA TGGACCTATG GAGGTGTCTG GCAGACTCCC CAGGGACTAC CTGCTCTCCT
2581 GGCCTGGCCT TGTCTGCCAC TGCCAGCTCC TACTCAGCCA TTCCTGAACA GAGGACAGCA
2641 GAGAAGGGCC AGCACCCTCC CAGAACCATG TGGCATTTGC CAACTGGATT TTGACCATAA
2701 CAATGCAGCC ATTCTCCCCA GCACCATCAT AGGCCCGCCC TTACAGGAGG ATTCGTTAGT
2761 AGAGTCCGCT CCTTGCCCCA CTAGTAACAG CTCACATGTC TGAGCACTGC TTACACCAGG
2821 CCTGGTGCAC GTGCTTTATG TGTCATTTCA TCACTGCCAG CCACCTCAAG AGGCAGGTAC
2881 GATGAACCCA TTCTGCTAAG GTTCAGTGAG GTTAAGTGAC AGAGGCTGGA TTCAAGCCAG
2941 GCCTGGCCAA CACCAGAGTG TCCATGCTCC TAACTGCAGT GTTCCCTCAC CATCAGAAGG
```

DIAGNOSTICS AND THERAPEUTICS FOR AN OBSTRUCTIVE AIRWAY DISEASE

PRIORITY INFORMATION AND INCORPORATION BY REFERENCE

The present application is a continuation-in-part of U.S. application Ser. No. 09/005,923, filed Jan. 12, 1998, which issued as U.S. Pat. No. 6,140,047 on Oct. 31, 2000. The contents of this priority application is incorporated herein by reference in its entirety.

1. BACKGROUND OF THE INVENTION

Asthma

Asthma is a chronic lung disease characterized by coughing, chest tightness, shortness of breath, and wheezing due to a reversible obstruction of airflow resulting from inflammation and hyper-responsiveness of the airways. An asthma attack is a dangerous overreaction by the immune systems, the lungs pump out mucus and inflammatory molecules, clogging and swelling constricted airways; in severe cases, all airflow is cut off and the attack may be fatal.

In sensitized individuals, inhalation of allergens may produce inflammation of the airway lining, and precipitate a flare-up of asthma. Asthma may also occur as a result of other inflammatory stimuli, such as respiratory tract infections. Individuals who have become sensitized to specific foods may have severely and possibly life-threatening reactions after ingestion of these substances. Asthma, once thought of as a "simple" hypersensitivity reaction, is now known to be a complex condition with a probable spectrum of causes and contributing factors, with airway inflammation as its central attribute.

Allergies contribute to both the incidence and severity of asthmatic symptoms. An allergy (also known as immediate hypersensitivity) is defined as an abnormal sensitivity to a substance which is normally tolerated and generally considered harmless, and for which the triggering event is dose-independent, as opposed to a dose-dependent idiosyncratic reaction to a substance. While all immune responses occur as a result of exposure to foreign substances, allergic reactions are distinct from the protective or enhanced "immunity" conferred by immunizations or natural infection. Only about a quarter of the children with asthma outgrow the condition when their airways reach adult size; for the rest, the condition is a lifelong ordeal. The condition persists, according to a research report published by the American Lung Association, in 85 percent of women and in 72 percent of men. (Journal of Allergy and Clinical Immunology Vol. 96:5 11/96). Asthma is typically characterized as either acute or chronic, although chronic diseases can have acute manifestations.

There were 4,964 deaths from asthma recorded in 1993 in the United States alone. The incidence of asthma mortality in children doubled from 1980 to 1993. Among persons between the ages of 15 and 24 years, the number of deaths rose from 2.5 cases per million in 1980 to 5.2 cases per million in 1993. In 1993, asthma accounted for 342 deaths and approximately 198,000 hospitalization in persons under 25 years of age.

African-Americans account for 21 percent of deaths due to asthma. African-American children are four times more likely to die of asthma than Caucasian children. African-American males between the ages of 15 and 24 have the highest risk of mortality.

A positive family history tends to be one of the strongest risk factors associated with asthma. Positive identification though, can be difficult. Asthma may coexist with other conditions such as congenital abnormalities, infectious conditions, and cystic fibrosis. Additional indicators are considered when the history is atypical or the response to good medical management is poor. Physicians with less experience in the management of this disease may treat these symptoms as an infection, not realizing that the underlying cause is asthma.

The identification of asthma in children relies heavily on the parents' observations for clinical clues. Correct identification requires an asthma and allergy specialist who recognizes the uniqueness of childhood asthma. More subtle signs of asthma, such as chest tightness, may be overlooked, particularly by children. Recurrent or constant coughing spells may be the only common observable symptoms of asthma in young children. Although, demonstration of a favorable clinical response to bronchodilator therapy can help confirm the presence of asthma.

Genetics of the IL-1 Gene Cluster The IL-1 gene cluster is on the long arm of chromosome 2 (2q13) and contains at least the genes for IL-1α (IL-1A), IL-1β (IL-1B), and the IL-1 receptor antagonist (IL-1RN), within a region of 430 Kb (Nicklin, et al. (1994) Genomics, 19: 382–4). The agonist molecules, IL-1α and IL-1β, have potent pro-inflammatory activity and are at the head of many inflammatory cascades. Their actions, often via the induction of other cytokines such as IL-6 and IL-8, lead to activation and recruitment of leukocytes into damaged tissue, local production of vasoactive agents, fever response in the brain and hepatic acute phase response. All three IL-1 molecules bind to type I and to type II IL-1 receptors, but only the type I receptor transduces a signal to the interior of the cell. In contrast, the type II receptor is shed from the cell membrane and acts as a decoy receptor. The receptor antagonist and the type II receptor, therefore, are both anti-inflammatory in their actions.

Inappropriate production of IL-1 plays a central role in the pathology of many autoimmune and inflammatory diseases, including rheumatoid arthritis, inflammatory bowel disorder, psoriasis, and the like. In addition, there are stable inter-individual differences in the rates of production of IL-1, and some of this variation may be accounted for by genetic differences at IL-1 gene loci. Thus, the IL-1 genes are reasonable candidates for determining part of the genetic susceptibility to inflammatory diseases, most of which have a multifactorial etiology with a polygenic component.

Certain alleles from the IL-1 gene cluster are known to be associated with particular disease states. For example, IL-1RN (VNTR) allele 2 has been shown to be associated with osteoporosis (U.S. Pat. No. 5,698,399), nephropathy in diabetes mellitus (Blakemore, et al. (1996) Hum. Genet. 97(3): 369–74), alopecia areata (Cork, et al., (1995) J. Invest. Dermatol. 104(5 Supp.): 15S–16S; Cork et al. (1996) Dermatol Clin 14: 671–8), Graves disease (Blakemore, et al. (1995) J. Clin. Endocrinol. 80(1): 111–5), systemic lupus erythematosus (Blakemore, et al. (1994) Arthritis Rheum. 37: 1380–85), lichen sclerosis (Clay, et al. (1994) Hum. Genet 94: 407–10), and ulcerative colitis (Mansfield, et al. (1994) Gastoenterol. 106(3): 637–42)).

In addition, the IL-1A allele 2 from marker −889 and IL-1B (TaqI) allele 2 from marker +3954 have been found to be associated with periodontal disease (U.S. Pat. No. 5,686,246; Kornman and diGiovine (1998) Ann Periodont 3: 327–38; Hart and Kornman (1997) Periodontol 2000 14: 202–15; Newman (1997) Compend Contin Educ Dent 18: 881–4; Kornman et al. (1997) J. Clin Periodontol 24:

72–77). The IL-1A allele 2 from marker −889 has also been found to be associated with juvenile chronic arthritis, particularly chronic iridocyclitis (McDowell, et al. (1995) Arthritis Rheum. 38: 221–28). The IL-1B (TaqI) allele 2 from marker +3954 of IL-1B has also been found to be associated with psoriasis and insulin dependent diabetes in DR3/4 patients (di Giovine, et al. (1995) Cytokine 7: 606; Pociot, et al. (1992) Eur J. Clin. Invest. 22: 396–402). Additionally, the IL-1RN (VNTR) allele 1 has been found to be associated with diabetic retinopathy (see U.S. Ser. No. 09/037472, and PCT/GB97/02790). Furthermore allele 2 of IL-1RN (VNTR) has been found to be associated with ulcerative colitis in Caucasian populations from North America and Europe (Mansfield, J. et al., (1994) Gastroenterology 106: 637–42). Interestingly, this association is particularly strong within populations of ethnically related Ashkenazi Jews (PCT W097/25445).

IL-13 and Asthma

IL13 is a cytokine produced by different T-cell subsets and dendritic cells. It shares many biological activities with IL 4 as both cytokines share the IL 4R alpha chain, which is important in signal transduction, and the IL-13 alpha 1 chain which amplifies this signal (DeWaal, M R and J E deVries "Interleukin 13, pp 427–442 in "The Cytokine Handbook" A. Thomas, Ed, (3rd ed) Academic Press, 1998). IL 13 inhibits inflammatory cytokine production (such as IL-1 beta, TNF alpha, IL 8, GRO beta and IL 6) induced by LPS in human peripheral blood monocytes (similar biologically to other TH2 cytokines like IL 4 and IL 10) and acts on B lymphocytes increasing their proliferation and expression of CD23, and inducing IgG4 and IgE production (Minty, A. et al., (1993) *Nature* 362: 248–250). IL 13 is the product of a gene located on chromosome 5q31. In this region, there is a cluster of genes with common structure, such as IL 3, IL 4, IL 5, with IL 13 particularly close to IL 4 (12 kb 5' to IL 4 gene in a tail-to-head orientation) (Smimov, D V et al., (1995) *Gene* 155(2): 277–281).

Important for the development of an atopic response such as asthma is the expansion of TH2 lymphocytes, which are characterized by the production of cytokines such as interleukin-4 (IL4), IL-5, IL-10 and IL-13 (Romagnani, S (1996) *Clin Immunol Immunopathol* 80(3): 225–235), encoded on chromosome 5q31, altogether with IL-3, IL-9, GM-CSF and the beta 2 $^{adrenergic}$ receptor (ADRB2 gene). Several studies have suggested that allelic variation in this region may play a role in the inheritance of IgE levels and asthma (Marsh, D G et al., (1994) *Science* 264:1152–1156; Meyers, D A et al., (1994) *Genet Epidemiol* 8: 351–359; Meyers, D A et al., (1994) *Genomics* 23: 464–470; Postma, D S et. al., (1995) *N Engl J Med* 333: 894–900).

Genotype Screening

Traditional methods for the screening of heritable diseases have depended on either the identification of abnormal gene products (e.g., sickle cell anemia) or an abnormal phenotype (e.g., mental retardation). These methods are of limited utility for heritable diseases with late onset and no easily identifiable phenotypes such as, for example, obstructive airway diseases. With the development of simple and inexpensive genetic screening methodology, it is now possible to identify polymorphisms that indicate a propensity to develop disease, even when the disease is of polygenic origin. The number of diseases that can be screened by molecular biological methods continues to grow with increased understanding of the genetic basis of multifactorial disorders.

Genetic screening (also called genotyping or molecular screening), can be broadly defined as testing to determine if a patient has mutations (or alleles or polymorphisms) that either cause a disease state or are "linked" to the mutation causing a disease state. Linkage refers to the phenomenon that DNA sequences which are close together in the genome have a tendency to be inherited together. Two sequences may be linked because of some selective advantage of co-inheritance. More typically, however, two polymorphic sequences are co-inherited because of the relative infrequency with which meiotic recombination events occur within the region between the two polymorphisms. The co-inherited polymorphic alleles are said to be in linkage disequilibrium with one another because, in a given human population, they tend to either both occur together or else not occur at all in any particular member of the population. Indeed, where multiple polymorphisms in a given chromosomal region are found to be in linkage disequilibrium with one another, they define a quasi-stable genetic "haplotype." In contrast, recombination events occurring between two polymorphic loci cause them to become separated onto distinct homologous chromosomes. If meiotic recombination between two physically linked polymorphisms occurs frequently enough, the two polymorphisms will appear to segregate independently and are said to be in linkage equilibrium.

While the frequency of meiotic recombination between two markers is generally proportional to the physical distance between them on the chromosome, the occurrence of "hot spots" as well as regions of repressed chromosomal recombination can result in discrepancies between the physical and recombinational distance between two markers. Thus, in certain chromosomal regions, multiple polymorphic loci spanning a broad chromosomal domain may be in linkage disequilibrium with one another, and thereby define a broad-spanning genetic haplotype. Furthermore, where a disease-causing mutation is found within or in linkage of this haplotype, one or more polymorphic alleles of the haplotype can be used as a diagnostic or prognostic indicator of the likelihood of developing the disease. This association between otherwise benign polymorphisms and a disease-causing polymorphism occurs if the disease mutation arose in the recent past, so that sufficient time has not elapsed for equilibrium to be achieved through recombination events. Therefore identification of a human haplotype which spans or is linked to a disease-causing mutational change, serves as a predictive measure of an individual's likelihood of having inherited that disease-causing mutation. Importantly, such prognostic or diagnostic procedures can be utilized without necessitating the identification and isolation of the actual disease-causing lesion. This is significant because the precise determination of the molecular defect involved in a disease process can be difficult and laborious, especially in the case of multifactorial diseases such as inflammatory disorders.

Indeed, the statistical correlation between a disorder and a polymorphism does not necessarily indicate that the polymorphism directly causes the disorder. Rather the correlated polymorphism may be a benign allelic variant which is linked to (i.e. in linkage disequilibrium with) a disorder-causing mutation which has occurred in the recent human evolutionary past, so that sufficient time has not elapsed for equilibrium to be achieved through recombination events in the intervening chromosomal segment. Thus, for the purposes of diagnostic and prognostic assays for a particular disease, detection of a polymorphic allele associated with that disease can be utilized without consideration of whether the polymorphism is directly involved in the etiology of the disease. Furthermore, where a given benign polymorphic locus is in linkage disequilibrium with an apparent disease-causing polymorphic locus, still other polymorphic loci which are in linkage disequilibrium with the benign polymorphic locus are also likely to be in linkage disequilibrium with the disease-causing polymorphic locus. Thus these other polymorphic loci will also be prognostic or diagnostic of the likelihood of having inherited the disease-causing polymorphic locus. Indeed, a broad-spanning human haplotype (describing the typical pattern of co-inheritance of alleles of a set of linked polymorphic markers) can be targeted for diagnostic purposes once an association has been drawn between a particular disease or condition and a corresponding human haplotype. Thus, the determination of an individual's likelihood for developing a particular disease of condition can be made by characterizing one or more disease-associated polymorphic alleles (or even one or more disease-associated haplotypes) without necessarily determining or characterizing the causative genetic variation.

There is a tremendous need for early identification of those who are generally susceptible to obstructive airway disease, such as asthma and those who are susceptible to acute episodes. Early identification would facilitate the prevention or administration of appropriate treatment at the earliest stage, thereby increasing the probability of a positive outcome.

2. SUMMARY OF THE INVENTION

In one aspect, the invention features assays for determining whether a subject has or is susceptible to developing an obstructive airway disease or prognosticating on the rapidity and/or ultimate progression (severity) of the disease in that subject. In one embodiment, the method comprises determining whether an allele associated with the disease is present in a nucleic acid from the subject. In a preferred embodiment the allele is IL-1B allele 2 (+3954) or an allele in linkage disequilibrium therewith or IL-1B allele 2 (−511) or an allele in linkage disequilibrium therewith. In another preferred embodiment for determining the likely severity of the disease, the allele is an allele of IL-13, eg. IL-13 allele 2 (+2581).

Appropriate alleles can be detected by any of a variety of means, including: 1) performing a hybridization reaction between the nucleic acid sample and a probe or probes that are capable of hybridizing to the allele; 2) sequencing at least a portion of the allele; or 3) determining the electrophoretic mobility of the allele or a component thereof. In another preferred embodiment, the allele is subject to an amplification step, prior to performance of the detection step. Preferred amplification steps are selected from the group consisiting of: the polymerase chain reaction (PCR), the ligase chain reaction (LCR), strand displacement amplification (SDA), cloning, and variations of the above (e.g. RT-PCR and allele specific amplification). In a particularly preferred embodiment, the sample is hybridized with a set of primers, which hybridize 5' and 3' to a sense or antisense sequence of an allele and is subject to a PCR amplification.

In another aspect, the invention features kits for performing the above-described assays. The kit can include DNA sample collection means and a means for determining an allele that is indicative of the existence and/or severity of an obstructive airway disease in a subject. The kit may also comprise control samples or standards.

Information obtained using the assays and kits described herein (alone or in conjunction with information on another genetic defect or environmental factor, which contributes to an obstructive airway disease) is useful for determining whether a subject has or is susceptible to developing an obstructive airway disease or prognosticating on the severity, rapidity and/or ultimate progression of the disease in that subject. In addition, the information alone or in conjunction with information on another genetic defect contributing to the same disease (the genetic profile of chronic obstructive airway disease) allows customization of therapy to the individual's genetic profile. For example, this information can enable a doctor to: 1) more effectively prescribe a drug that will address the molecular basis of chronic obstructive airway disease; and 2) better determine the appropriate dosage of a particular drug for a particular patient. The ability to target patient populations expected to show the highest clinical benefit, can enable: 1) the repositioning of marketed drugs with disappointing market results; 2) the rescue of drug candidates whose clinical development has been discontinued as a result of safety or efficacy limitations, which are patient subgroup-specific; and 3) an accelerated and less costly development for drug candidates and more optimal drug labeling.

Other features and advantages of the invention will be apparent from the following detailed description and claims.

3. BRIEF DESCRIPTION OF THE DRAWINGS

FIG. 1 shows the DNA sequence of the human IL-1A gene (GenBank Accession No. X03833; SEQ ID No. 1).

FIG. 2 shows the DNA sequence of the human IL-1B gene (GenBank Accession No. X04500; SEQ ID No. 2).

Figure 3E:
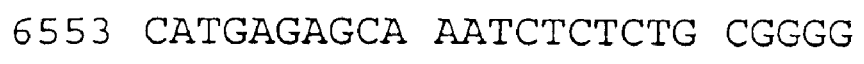

FIG. 3 shows the DNA sequence of the human IL1-RN gene (GenBank Accession No. X64532; SEQ ID NO. 3).

FIG. 4 shows the DNA sequence of the human IL-13 gene (GenBank Accession No. U31120; SEQ ID No. 4).

FIG. 5 is a graph showing the frequencies of various haplotype patterns in a Caucasian population.

4. DETAILED DESCRIPTION OF THE INVENTION

4.1 Definitions

For convenience, the meaning of certain terms and phrases employed in the specification, examples, and appended claims are provided below.

The term "allele" refers to the different sequence variants found at different polymorphic regions. For example, IL-1RN (VNTR) has at least five different alleles. The sequence variants may be single or multiple base changes, including without limitation insertions, deletions, or substitutions, or may be a variable number of sequence repeats.

The term "allelic pattern" refers to the identity of an allele or alleles at one or more polymorphic regions. For example, an allelic pattern may consist of a single allele at a polymorphic site, as for IL-1RN (VNTR) allele 1, which is an allelic pattern having at least one copy of IL-1RN allele 1 at the VNTR of the IL-1RN gene loci. Alternatively, an allelic pattern may consist of either a homozygous or heterozygous state at a single polymorphic site. For example, IL1-RN (VNTR) allele 2,2 is an allelic pattern in which there are two copies of the second allele at the VNTR marker of IL-1RN and that corresponds to the homozygous IL-RN (VNTR) allele 2 state. Alternatively, an allelic pattern may consist of the identity of alleles at more than one polymorphic site.

The term "antibody" as used herein is intended to refer to a binding agent including a whole antibody or a binding fragment thereof which is specifically reactive with an IL-1B polypeptide. Antibodies can be fragmented using conventional techniques and the fragments screened for utility in the same manner as described above for whole antibodies. For example, F(ab)$_2$ fragments can be generated by treating an antibody with pepsin. The resulting F(ab)$_2$ fragment can be treated to reduce disulfide bridges to produce Fab fragments. The antibody of the present invention is further intended to include bispecific, single-chain, and chimeric and humanized molecules having affinity for an IL-1B polypeptide conferred by at least one CDR region of the antibody.

"Biological activity" or "bioactivity" or "activity" or "biological function", which are used interchangeably, for the purposes herein means an effector or antigenic function that is directly or indirectly performed by an IL-1 polypeptide (whether in its native or denatured conformation), or by any subsequence thereof. Biological activities include binding to a target peptide, e.g., an IL-1 receptor. An IL-1 bioactivity can be modulated by directly affecting an IL-1 polypeptide. Alternatively, an IL-1 bioactivity can be modulated by modulating the level of an IL-1 polypeptide, such as by modulating expression of an IL-1 gene.

As used herein the term "bioactive fragment of an IL-1 polypeptide" refers to a fragment of a full-length IL-1 polypeptide, wherein the fragment specifically mimics or antagonizes the activity of a wild-type IL-1 polypeptide. The bioactive fragment preferably is a fragment capable of interacting with an interleukin receptor.

The term "an aberrant activity", as applied to an activity of a polypeptide such as IL-1, refers to an activity which differs from the activity of the wild-type or native polypeptide or which differs from the activity of the polypeptide in a healthy subject. An activity of a polypeptide can be aberrant because it is stronger than the activity of its native counterpart. Alternatively, an activity can be aberrant because it is weaker or absent relative to the activity of its native counterpart. An aberrant activity can also be a change in an activity. For example an aberrant polypeptide can interact with a different target peptide. A cell can have an aberrant IL-1 activity due to overexpression or underexpression of an IL-1 locus gene encoding an IL-1 locus polypeptide.

"Cells", "host cells" or "recombinant host cells" are terms used interchangeably herein to refer not only to the particular subject cell, but to the progeny or potential progeny of such a cell. Because certain modifications may occur in succeeding generations due to either mutation or environmental influences, such progeny may not, in fact be identical to the parent cell, but is still included within the scope of the term as used herein.

A "chimera," "mosaic," "chimeric mammal" and the like, refers to a transgenic mammal with a knock-out or knock-in construct in at least some of its genome-containing cells.

The terms "control" or "control sample" refer to any sample appropriate to the detection technique employed. The control sample may contain the products of the allele detection technique employed or the material to be tested. Further, the controls may be positive or negative controls. By way of example, where the allele detection technique is PCR amplification, followed by size fractionation, the control sample may comprise DNA fragments of an appropriate size. Likewise, where the allele detection technique involves detection of a mutated protein, the control sample may comprise a sample of a mutant protein. However, it is preferred that the control sample comprises the material to be tested. For example, the controls may be a sample of genomic DNA or a cloned portion of the IL-1 gene cluster. However, where the sample to be tested is genomic DNA, the control sample is preferably a highly purified sample of genomic DNA.

The phrases "disruption of the gene" and "targeted disruption" or any similar phrase refers to the site specific interruption of a native DNA sequence so as to prevent expression of that gene in the cell as compared to the wild-type copy of the gene. The interruption may be caused by deletions, insertions or modifications to the gene, or any combination thereof.

"Genotyping" refers to the analysis of an individual's genomic DNA (or a nucleic acid corresponding thereto) to identify a particular disease causing or contributing mutation or polymorphism, directly or based on detection of a mutation or polymorphism (a marker) that is in linkage disequilibrium with the disease causing or contributing gene.

The term "haplotype" as used herein is intended to refer to a set of alleles that are inherited together as a group (are in linkage disequilibrium) at statistically significant levels ($p_{corr}$<0.05). As used herein, the phrase "an IL-1 haplotype" refers to a haplotype in the IL-1 loci.

The terms "IL-1 gene cluster" and "IL-1 loci" as used herein include all the nucleic acid at or near the 2q13 region of chromosome 2, including at least the IL-1A, IL-1B and IL-1RN genes and any other linked sequences. (Nicklin et al., Genomics 19: 382–84, 1994). The terms "IL-1A", "IL-1B", and "IL-1RN" as used herein refer to the genes coding for IL-1, IL-1, and IL-1 receptor antagonist, respectively. The gene accession number for IL-1A, IL-1B, and IL-1RN are X03833, X04500, and X64532, respectively.

"IL functional mutation" refers to a mutation within an interleukin gene that results in an altered phenotype (i.e. effects the function of an interleukin gene or protein). Examples include: IL-1A (+4845) allele 2, IL-1B (+3954) allele 2, IL-1B (+6912) allele 2 and IL-1RN (+2018allele 2.

"IL-1X (Z) allele Y" refers to a particular allelic form, designated Y, occurring at an IL-1 locus polymorphic site in gene X, wherein X is IL-1A, B, or RN or some other gene in the IL-1 gene loci, and positioned at or near nucleotide Z, wherein nucleotide Z is numbered relative to the major transcriptional start site, which is nucleotide +1, of the particular IL-1 gene X. As further used herein, the term "IL-1X allele (Z)" refers to all alleles of an IL-1 polymorphic site in gene X positioned at or near nucleotide Z. For example, the term "IL-1RN (+2018) allele" refers to alternative forms of the IL-1RN gene at marker +2018. "IL-1RN (+2018) allele 1" refers to a form of the IL-1RN gene which contains a cytosine (C) at position +2018 of the sense strand. Clay et al., Hum. Genet. 97:723–26,1996. "IL-1RN (+2018) allele 2" refers to a form of the IL-1RN gene which contains a thymine (T) at position +2018 of the plus strand. When a subject has two identical IL-1RN alleles, the subject is said to be homozygous, or to have the homozygous state. When a subject has two different IL-1RN alleles, the subject is said to be heterozygous, or to have the heterozygous state. The term "IL-1RN (+2018) allele 2,2" refers to the homozygous IL-1RN (+2018) allele 2 state. Conversely, the term "IL-1RN (+2018) allele 1,1" refers to the homozygous IL-1RN (+2018) allele 1 state. The term "IL-1RN (+2018) allele 1,2" refers to the heterozygous allele 1 and 2 state.

"IL-1 related" as used herein is meant to include all genes related to the human IL-1 locus genes on human chromosome 2 (2q 12–14). These include IL-1 genes of the human IL-1 gene cluster located at chromosome 2 (2q 13–14)

which include: the IL-1A gene which encodes interleukin-1α, the IL-1B gene which encodes interleukin-1β, and the IL-1RN (or IL-1ra) gene which encodes the interleukin-1 receptor antagonist. Furthermore these IL-1 related genes include the type I and type II human IL-1 receptor genes located on human chromosome 2 (2q12) and their mouse homologs located on mouse chromosome 1 at position 19.5 cM. Interleukin-1α, interleukin-1β, and interleukin-1RN are related in so much as they all bind to IL-1 type I receptors, however only interleukin-1α and interleukin-1β are agonist ligands which activate IL-1 type I receptors, while interleukin-1RN is a naturally occurring antagonist ligand. Where the term "IL-1" is used in reference to a gene product or polypeptide, it is meant to refer to all gene products encoded by the interleukin-1 locus on human chromosome 2 (2q 12–14) and their corresponding homologs from other species or functional variants thereof. The term IL-1 thus includes secreted polypeptides which promote an inflammatory response, such as IL-1α and IL-1β, as well as a secreted polypeptide which antagonize inflammatory responses, such as IL-1 receptor antagonist and the IL-1 type II (decoy) receptor.

An "IL-1 receptor" or "IL-1R" refers to various cell membrane bound protein receptors capable of binding to and/or transducing a signal from IL-1 locus-encoded ligand. The term applies to any of the proteins which are capable of binding interleukin-1 (IL-1) molecules and, in their native configuration as mammalian plasma membrane proteins, presumably play a role in transducing the signal provided by IL-1 to a cell. As used herein, the term includes analogs of native proteins with IL-1-binding or signal transducing activity. Examples include the human and murine IL-1 receptors described in U.S. Pat. No. 4,968,607. The term "IL-1 nucleic acid" refers to a nucleic acid encoding an IL-1 protein.

An "IL-1 polypeptide" and "IL-1 protein" are intended to encompass polypeptides comprising the amino acid sequence encoded by the IL-1 genomic DNA sequences shown in FIGS. 1, 2, and 3, or fragments thereof, and homologs thereof and include agonist and antagonist polypeptides.

An "IL-13 receptor" or "IL-13R" refers to various cell membrane bound protein receptors capable of binding to and/or transducing a signal from IL-13 locus-encoded ligand. The term applies to any of the proteins which are capable of binding interleukin-13 (IL-13) molecules and, in their native configuration as mammalian plasma membrane proteins, presumably play a role in transducing the signal provided by IL-13 to a cell. As used herein, the term includes analogs of native proteins with IL-13-binding or signal transducing activity.

An "EL-13 polypeptide" and "IL-13 protein" are intended to encompass polypeptides comprising the amino acid sequence encoded by the IL-13 genomic DNA sequence shown in FIG. 4 or fragments thereof, and homologs thereof and include agonist and antagonist polypeptides.

"Increased risk" refers to a statistically higher frequency of occurrence of the disease or condition in an individual carrying a particular polymorphic allele in comparison to the frequency of occurrence of the disease or condition in a member of a population that does not carry the particular polymorphic allele.

The term "interact" as used herein is meant to include detectable relationships or associations (e.g. biochemical interactions) between molecules, such as interactions between protein-protein, protein-nucleic acid, nucleic acid-nucleic acid and protein-small molecule or nucleic acid-small molecule in nature.

A "knock-in" transgenic animal refers to an animal that has had a modified gene introduced into its genome and the modified gene can be of exogenous or endogenous origin.

A "knock-out" transgenic animal refers to an animal in which there is partial or complete suppression of the expression of an endogenous gene (e.g, based on deletion of at least a portion of the gene, replacement of at least a portion of the gene with a second sequence, introduction of stop codons, the mutation of bases encoding critical amino acids, or the removal of an intron junction, etc.).

A "knock-out construct" refers to a nucleic acid sequence that can be used to decrease or suppress expression of a protein encoded by endogenous DNA sequences in a cell. In a simple example, the knock-out construct is comprised of a gene, such as the IL-1RN gene, with a deletion in a critical portion of the gene so that active protein cannot be expressed therefrom. Alternatively, a number of termination codons can be added to the native gene to cause early termination of the protein or an intron junction can be inactivated. In a typical knock-out construct, some portion of the gene is replaced with a selectable marker.

"Linkage disequilibrium" refers to co-inheritance of two alleles at frequencies greater than would be expected from the separate frequencies of occurrence of each allele in a given control population. The expected frequency of occurrence of two alleles that are inherited independently is the frequency of the first allele multiplied by the frequency of the second allele. Alleles that co-occur at expected frequencies are said to be in "linkage disequilibrium". The cause of linkage disequilibrium is often unclear. It can be due to selection for certain allele combinations or to recent admixture of genetically heterogeneous populations. In addition, in the case of markers that are very tightly linked to a disease gene, an association of an allele (or group of linked alleles) with the disease gene is expected if the disease mutation occurred in the recent past, so that sufficient time has not elapsed for equilibrium to be achieved through recombination events in the specific chromosomal region. When referring to allelic patterns that are comprised of more than one allele, a first allelic pattern is in linkage disequilibrium with a second allelic pattern if all the alleles that comprise the first allelic pattern are in linkage disequilibrium with at least one of the alleles of the second allelic pattern. An example of linkage disequilibrium is that which occurs between the alleles at the IL-1RN (+2018) and IL-1RN (VNTR) polymorphic sites. The two alleles at IL-1RN (+2018) are 100% in linkage disequilibrium with the two most frequent alleles of IL-1RN (VNTR), which are allele 1 and allele 2.

The term "marker" refers to a sequence in the genome that is known to vary among individuals. For example, the IL-1RN gene has a marker that consists of a variable number of tandem repeats (VNTR).

A "mutated gene" or "mutation" or "functional mutation" refers to an allelic form of a gene, which is capable of altering the phenotype of a subject having the mutated gene relative to a subject which does not have the mutated gene. The altered phenotype caused by a mutation can be corrected or compensated for by certain agents. If a subject must be homozygous for this mutation to have an altered phenotype, the mutation is said to be recessive. If one copy of the mutated gene is sufficient to alter the phenotype of the subject, the mutation is said to be dominant. If a subject has one copy of the mutated gene and has a phenotype that is intermediate between that of a homozygous and that of a heterozygous subject (for that gene), the mutation is said to be co-dominant.

A "non-human animal" of the invention includes mammals such as rodents, non-human primates, sheep, dogs, cows, goats, etc. amphibians, such as members of the *Xenopus genus*, and transgenic avians (e.g. chickens, birds, etc.). The term "chimeric animal" is used herein to refer to animals in which the recombinant gene is found, or in which the recombinant gene is expressed in some but not all cells of the animal. The term "tissue-specific chimeric animal" indicates that one of the recombinant IL-1 genes is present and/or expressed or disrupted in some tissues but not others. The term "non-human mammal" refers to any member of the class Mammalia, except for humans.

As used herein, the term "nucleic acid" refers to polynucleotides or oligonucleotides such as deoxyribonucleic acid (DNA), and, where appropriate, ribonucleic acid (RNA). The term should also be understood to include, as equivalents, analogs of either RNA or DNA made from nucleotide analogs (e.g. peptide nucleic acids) and as applicable to the embodiment being described, single (sense or antisense) and double-stranded polynucleotides.

An "obstructive lung disease" or "obstructive airway disease" (OAD) are terms used to describe a complex of chronic and acute conditions that have in common airflow limitation or airflow obstruction. OADs includes asthma, emphysema, chronic bronchitis, and chronic bronchiolitis. The sites of airway obstruction in OADs vary from the upper airways to the most peripheral bronchioles. The exact cause of most diseases of the airways is not well understood. The definition of airway diseases add to the confusion. Chronic bronchitis is defined clinically by the chronic presence of cough and sputum production. Emphysema, on the other hand, is defined anatomically, on the basis of the breakdown of lung tissue and the enlargement of the alveolar sacs. OADs all have airway narrowing as a disease parameter and they also share inflammation as a component of the disease process.

An "OAD associated allele" or "an allele associated with an obstructive airway disorder" refers to an allele whose presence in a subject indicates that the subject has or is susceptible to developing an OAD. Examples of an OAD associated allele include: IL-13 allele 2 (+2581), IL-1B allele 2 (+3954) and IL-1B allele 2 (−511).

An "OAD causative functional mutation" refers to a mutation which causes or contributes to the development of an OAD in a subject. Preferred mutations occur within an interleukin gene. An OAD causative functional mutation occurring within an interleukin gene or a gene locus, which is linked thereto, may alter, for example, the open reading frame or splicing pattern of the gene, thereby resulting in the formation of an inactive or hypoactive gene product. For example, a mutation which occurs in intron 6 of the IL-1A locus corresponds to a variable number of tandem repeat 46 bp sequences corresponding to from five to 18 repeat units (Bailly, et al. (1993) Eur. J. Immunol. 23: 1240–45). These repeat sequences contain three potential binding sites for transcriptional factors: an SP1 site, a viral enhancer element, and a glucocorticoid-responsive element; therefore individuals carrying IL-1A intron 6 VNTR alleles with large numbers of repeat units may be subject to altered transcriptional regulation of the IL-1A gene and consequent perturbations of inflammatory cytokine production. Indeed, there is evidence that increased repeat number at this polymorphic IL-1A locus leads to decreased IL-1α synthesis (Bailly et al. (1996) Mol Immunol 33: 999–1006). Alternatively, a mutation can result in a hyperactive gene product. For example, allele 2 of the IL-1B (G at+6912) polymorphism occurs in the 3' UTR (untranslated region) of the IL-1B mRNA and is associated with an approximately four-fold increase in the steady state levels of both IL-1B mRNA and IL-1B protein compared to those levels associated with allele 1 of the IL-1B gene © at+6912). Further, an IL-1B (−511) mutation occurs near a promoter binding site for a negative glucocorticoid response element (Zhang et al. (1997) DNA Cell Biol 16: 145–52). This element potentiates a four-fold repression of IL-1B expression by dexamethosone and a deletion of this negative response elements causes a 2.5-fold increase in IL-1B promoter activity. The IL-1B (−511) polymorphism may thus directly affect cytokine production and inflammatory responses. These examples demonstrate that genetic variants occurring in the IL-1A or IL-1B gene can directly lead to the altered production or regulation of IL-1 cytokine activity.

The term "polymorphism" refers to the coexistence of more than one form of a gene or portion (e.g., allelic variant) thereof. A portion of a gene of which there are at least two different forms, i.e., two different nucleotide sequences, is referred to as a "polymorphic region of a gene". A specific genetic sequence at a polymorphic region of a gene is an allele. A polymorphic region can be a single nucleotide, the identity of which differs in different alleles. A polymorphic region can also be several nucleotides long.

The term "propensity to disease," also "predisposition" or "susceptibility" to disease or any similar phrase, means that certain alleles are hereby discovered to be associated with or predictive of a subject's incidence of developing a particular disease (e.g. a chronic obstructive airway disease). The alleles are thus over-represented in frequency in individuals with disease as compared to healthy individuals. Thus, these alleles can be used to predict disease even in pre-symptomatic or pre-diseased individuals.

"Small molecule" as used herein, is meant to refer to a composition, which has a molecular weight of less than about 5 kD and most preferably less than about 4 kD. Small molecules can be nucleic acids, peptides, peptidomimetics, carbohydrates, lipids or other organic or inorganic molecules.

As used herein, the term "specifically hybridizes" or "specifically detects" refers to the ability of a nucleic acid molecule to hybridize to at least approximately 6 consecutive nucleotides of a sample nucleic acid.

"Transcriptional regulatory sequence" is a generic term used throughout the specification to refer to DNA sequences, such as initiation signals, enhancers, and promoters, which induce or control transcription of protein coding sequences with which they are operably linked.

As used herein, the term "transgene" means a nucleic acid sequence (encoding, e.g., one of the IL polypeptides, or an antisense transcript thereto) which has been introduced into a cell. A transgene could be partly or entirely heterologous, i.e., foreign, to the transgenic animal or cell into which it is introduced, or, is homologous to an endogenous gene of the transgenic animal or cell into which it is introduced, but which is designed to be inserted, or is inserted, into the animal's genome in such a way as to alter the genome of the cell into which it is inserted (e.g., it is inserted at a location which differs from that of the natural gene or its insertion results in a knockout). A transgene can also be present in a cell in the form of an episome. A transgene can include one or more transcriptional regulatory sequences and any other nucleic acid, such as introns, that may be necessary for optimal expression of a selected nucleic acid.

A "transgenic animal" refers to any animal, preferably a non-human mammal, bird or an amphibian, in which one or more of the cells of the animal contain heterologous nucleic acid introduced by way of human intervention, such as by transgenic techniques well known in the art. The nucleic acid is introduced into the cell, directly or indirectly by introduction into a precursor of the cell, by way of deliberate genetic manipulation, such as by microinjection or by infection with a recombinant virus. The term genetic manipulation does not include classical cross-breeding, or in vitro fertilization, but rather is directed to the introduction of a recombinant DNA molecule. This molecule may be integrated within a chromosome, or it may be extrachromosomally replicating DNA. In the typical transgenic animals described herein, the transgene causes cells to express a recombinant form of one of an IL polypeptide, e.g. either agonistic or antagonistic forms. However, transgenic animals in which the recombinant gene is silent are also contemplated, as for example, the FLP or CRE recombinase dependent constructs described below. Moreover, "transgenic animal" also includes those recombinant animals in which gene disruption of one or more genes is caused by human intervention, including both recombination and antisense techniques. The term is intended to include all progeny generations. Thus, the founder animal and all F1, F2, F3, and so on, progeny thereof are included.

The term "treating" as used herein is intended to encompass curing as well as ameliorating at least one symptom of a condition or disease.

The term "vector" refers to a nucleic acid molecule, which is capable of transporting another nucleic acid to which it has been linked. One type of preferred vector is an episome, i.e., a nucleic acid capable of extra-chromosomal replication. Preferred vectors are those capable of autonomous replication and/or expression of nucleic acids to which they are linked. Vectors capable of directing the expression of genes to which they are operatively linked are referred to herein as "expression vectors". In general, expression vectors of utility in recombinant DNA techniques are often in the form of "plasmids" which refer generally to circular double stranded DNA loops which, in their vector form are not bound to the chromosome. In the present specification, "plasmid" and "vector" are used interchangeably as the plasmid is the most commonly used form of vector. a However, the invention is intended to include such other forms of expression vectors which serve equivalent functions and which become known in the art subsequently hereto.

The term "wild-type allele" refers to an allele of a gene which, when present in two copies in a subject results in a wild-type phenotype. There can be several different wild-type alleles of a specific gene, since certain nucleotide changes in a gene may not affect the phenotype of a subject having two copies of the gene with the nucleotide changes.

4.2 Predictive Medicine
4.2.1. Prognostic Assays and Kits

The invention is based, at least in part, on the findings, which are described in detail in the following examples, that the IL-1B allele 2 (+3954) and IL-1B allele 2 (−511) are significantly associated with the development of asthma in a subject and that IL-1B (−511) and IL-13 allele 2 (+2581) are significantly associated with severe asthma. The present invention, therefore provides methods and kits for determining whether a subject has or is likely to develop asthma and/or for predicting the extent or progression or relative severity of such a disease in a subject.

In addition to the allelic patterns described above, as described herein, one of skill in the art can readily identify other alleles (including polymorphisms and mutations) that are in linkage disequilibrium with an allele associated with an obstructive airway disease. For example, a nucleic acid sample from a first group of subjects without a particular disorder can be collected, as well as DNA from a second group of subjects with the disorder. The nucleic acid sample can then be compared to identify those alleles that are over-represented in the second group as compared with the first group, wherein such alleles are presumably associated with a disorder, which is caused or contributed to by inappropriate interleukin 1 regulation. Alternatively, alleles that are in linkage disequilibrium with an allele that is associated with the disorder can be identified, for example, by genotyping a large population and performing statistical analysis to determine which alleles appear more commonly together than expected. Preferably the group is chosen to be comprised of genetically related individuals. Genetically related individuals include individuals from the same race, the same ethnic group, or even the same family. As the degree of genetic relatedness between a control group and a test group increases, so does the predictive value of polymorphic alleles which are ever more distantly linked to a disease-causing allele. This is because less evolutionary time has passed to allow polymorphisms which are linked along a chromosome in a founder population to redistribute through genetic cross-over events. Thus race-specific, ethnic-specific, and even family-specific diagnostic genotyping assays can be developed to allow for the detection of disease alleles which arose at ever more recent times in human evolution, e.g., after divergence of the major human races, after the separation of human populations into distinct ethnic groups, and even within the recent history of a particular family line.

Linkage disequilibrium between two polymorphic markers or between one polymorphic marker and a disease-causing mutation is a meta-stable state. Absent selective pressure or the sporadic linked reoccurrence of the underlying mutational events, the polymorphisms will eventually become disassociated by chromosomal recombination events and will thereby reach linkage equilibrium through the course of human evolution. Thus, the likelihood of finding a polymorphic allele in linkage disequilibrium with a disease or condition may increase with changes in at least two factors: decreasing physical distance between the polymorphic marker and the disease-causing mutation, and decreasing number of meiotic generations available for the dissociation of the linked pair. Consideration of the latter factor suggests that, the more closely related two individuals are, the more likely they will share a common parental chromosome or chromosomal region containing the linked polymorphisms and the less likely that this linked pair will have become unlinked through meiotic cross-over events occurring each generation. As a result, the more closely related two individuals are, the more likely it is that widely spaced polymorphisms may be co-inherited. Thus, for individuals related by common race, ethnicity or family, the reliability of ever more distantly spaced polymorphic loci can be relied upon as an indicator of inheritance of a linked disease-causing mutation.

In another embodiment, the method of the invention may be employed by detecting the presence of an IL-1 associated polymorphism that is in linkage disequilibrium with one or more of the aforementioned restenosis-predictive alleles. For example, the following alleles of the IL-1 (44112332) haplotype are known to be in linkage disequilibrium:

allele 4 of the 222/223 marker of IL-1A
allele 4 of the gz5/gz6 marker of IL-1A
allele 1 of the −889 marker of IL-1A
allele 1 of the +3954 marker of IL-1B
allele 2 of the −511 marker of IL-1B
allele 3 of the gaat.p33330 marker
allele 3 of the Y31 marker
allele 2 of the VNTR or (+2018) marker of IL-1RN Also, the following alleles of the IL-1 (33221461) haplotype are in linkage disequilibrium:

allele 3 of the 222/223 marker of IL-1A
allele 3 of the gz5/gz6 marker of IL-1A
allele 2 of the −889 marker of IL-1A
allele 2 of the +3954 marker of IL-1B
allele 1 of the −511 marker of IL-1B
allele 4 of the gaat.p33330 marker
allele 6 of the Y31 marker
allele 1 of the VNTR or (+2018) marker of IL-1RN Appropriate probes may be designed to hybridize to a specific gene of the IL-1 locus, such as IL-1A, IL-1B or IL-1RN, 1L-13 or a related gene. These genomic DNA sequences are shown in FIGS. 1–4, respectively, and further correspond to SEQ ID Nos. 1–4, respectively. Alternatively, these probes may incorporate other regions of the relevant genomic locus, including intergenic sequences. Indeed the IL-1 region of human chromosome 2 spans some 400,000 base pairs and, assuming an average of one single nucleotide polymorphism every 1,000 base pairs, includes some 400 SNPs loci alone. Yet other polymorphisms available for use with the immediate invention are obtainable from various public sources. For example, the human genome database collects intragenic SNPs, is searchable by sequence and currently contains approximately 2,700 entries (http://hgbase.interactiva.de). Also available is a human polymorphism database maintained by the Massachusetts Institute of Technology (MIT SNP database (http://www.genome.wi.mit.edu/SNP/human/index.html)). From such sources SNPs as well as other human polymorphisms may be found.

For example, examination of the IL-1 region of the human genome in any one of these databases reveals that the IL-1 locus genes are flanked by a centromere proximal polymorphic marker designated microsatellite marker AFM220ze3 at 127.4 cM (centiMorgans) (see GenBank Acc. No. Z17008) and a distal polymorphic marker designated microsatellite anchor marker AFM087xa1 at 127.9 cM (see GenBank Acc. No. Z16545). These human polymorphic loci are both CA dinucleotide repeat microsatellite polymorphisms, and, as such, show a high degree of heterozygosity in human populations. For example, one allele of AFM220ze3 generates a 211 bp PCR amplification product with a 5' primer of the sequence TGTACCTAAGC-CCACCCTTTAGAGC (SEQ ID No. 5) and a 3' primer of the sequence TGGCCTCCAGAAACCTCCAA (SEQ ID No. 6). Furthermore, one allele of AFM087xa1 generates a 177 bp PCR amplification product with a 5' primer of the sequence GCTGATATTCTGGTGGGAAA (SEQ ID No. 7) and a 3' primer of the sequence GGCAAGAG-CAAAACTCTGTC (SEQ ID No. 8). Equivalent primers corresponding to unique sequences occurring 5' and 3' to these human chromosome 2 CA dinucleotide repeat polymorphisms will be apparent to one of skill in the art. Reasonable equivalent primers include those which hybridize within about 1 kb of the designated primer, and which further are anywhere from about 17 bp to about 27 bp in length. A general guideline for designing primers for amplification of unique human chromosomal genomic sequences is that they possess a melting temperature of at least about 50° C., wherein an approximate melting temperature can be estimated using the formula $T_{melt}=[2\times(\#$ of A or T$)+4\times(\#$ of G or C$)]$.

A number of other human polymorphic loci occur between these two CA dinucleotide repeat polymorphisms and provide additional targets for determination of a prognostic allele in a family or other group of genetically related individuals. For example, the National Center for Biotechnology Information web site (www.ncbi.nlm.nih.gov/genemap/) lists a number of polymorphism markers in the region of the IL-1 locus and provides guidance in designing appropriate primers for amplification and analysis of these markers.

Accordingly, the nucleotide segments of the invention may be used for their ability to selectively form duplex molecules with complementary stretches of human chromosome 2 q 12–13 or cDNAs from that region or to provide primers for amplification of DNA or cDNA from this region. The design of appropriate probes for this purpose requires consideration of a number of factors. For example, fragments having a length of between 10, 15, or 18 nucleotides to about 20, or to about 30 nucleotides, will find particular utility. Longer sequences, e.g., 40, 50, 80, 90, 100, even up to full length, are even more preferred for certain embodiments. Lengths of oligonucleotides of at least about 18 to 20 nucleotides are well accepted by those of skill in the art as sufficient to allow sufficiently specific hybridization so as to be useful as a molecular probe. Furthermore, depending on the application envisioned, one will desire to employ varying conditions of hybridization to achieve varying degrees of selectivity of probe towards target sequence. For applications requiring high selectivity, one will typically desire to employ relatively stringent conditions to form the hybrids. For example, relatively low salt and/or high temperature conditions, such as provided by 0.02 M–0.15M NaCl at temperatures of about 50° C. to about 70° C. Such selective conditions may tolerate little, if any, mismatch between the probe and the template or target strand.

Other alleles or other indicia of a disorder can be detected or monitored in a subject in conjunction with detection of the alleles described above.

Many methods are available for detecting specific alleles at human polymorphic loci. The preferred method for detecting a specific polymorphic allele will depend, in part, upon the molecular nature of the polymorphism. For example, the various allelic forms of the polymorphic locus may differ by a single base-pair of the DNA. Such single nucleotide polymorphisms (or SNPs) are major contributors to genetic variation, comprising some 80% of all known polymorphisms, and their density in the human genome is estimated to be on average 1 per 1,000 base pairs. SNPs are most frequently biallelic-occurring in only two different forms (although up to four different forms of an SNP, corresponding to the four different nucleotide bases occurring in DNA, are theoretically possible). Nevertheless, SNPs are mutationally more stable than other polymorphisms, making them suitable for association studies in which linkage disequilibrium between markers and an unknown variant is used to map disease-causing mutations. In addition, because SNPs typically have only two alleles, they can be genotyped by a simple plus/minus assay rather than a length measurement, making them more amenable to automation.

A variety of methods are available for detecting the presence of a particular single nucleotide polymorphic allele in an individual. Advancements in this field have provided accurate, easy, and inexpensive large-scale SNP genotyping. Most recently, for example, several new techniques have been described including dynamic allele-specific hybridization (DASH), microplate array diagonal gel electrophoresis (MADGE), pyrosequencing, oligonucleotide-specific ligation, the TaqMan system as well as various DNA "chip" technologies such as the Affymetrix SNP chips. These methods require amplification of the target genetic region, typically by PCR. Still other newly developed methods, based on the generation of small signal molecules by invasive cleavage followed by mass spectrometry or immobilized padlock probes and rolling-circle amplification, might eventually eliminate the need for PCR. Several of the methods known in the art for detecting a specific single nucleotide polymorphisms are summarized below. The method of the present invention is understood to include all available methods.

Several methods have been developed to facilitate analysis of single nucleotide polymorphisms. In one embodiment, the single base polymorphism can be detected by using a specialized exonuclease-resistant nucleotide, as disclosed, e.g., in Mundy, C. R. (U.S. Pat. No. 4,656,127). According to the method, a primer complementary to the allelic sequence immediately 3' to the polymorphic site is permitted to hybridize to a target molecule obtained from a particular animal or human. If the polymorphic site on the target molecule contains a nucleotide that is complementary to the particular exonuclease-resistant nucleotide derivative present, then that derivative will be incorporated onto the end of the hybridized primer. Such incorporation renders the primer resistant to exonuclease, and thereby permits its detection. Since the identity of the exonuclease-resistant derivative of the sample is known, a finding that the primer has become resistant to exonucleases reveals that the nucleotide present in the polymorphic site of the target molecule was complementary to that of the nucleotide derivative used in the reaction. This method has the advantage that it does not require the determination of large amounts of extraneous sequence data.

In another embodiment of the invention, a solution-based method is used for determining the identity of the nucleotide of a polymorphic site. Cohen, D. et al. (French Patent 2,650,840; PCT Appln. No. WO91/02087). As in the Mundy method of U.S. Pat. No. 4,656,127, a primer is employed that is complementary to allelic sequences immediately 3' to a polymorphic site. The method determines the identity of the nucleotide of that site using labeled dideoxynucleotide derivatives, which, if complementary to the nucleotide of the polymorphic site will become incorporated onto the terminus of the primer.

An alternative method, known as Genetic Bit Analysis or GBA™ is described by Goelet, P. et al. (PCT Appln. No. 92/15712). The method of Goelet, P. et al. uses mixtures of labeled terminators and a primer that is complementary to the sequence 3' to a polymorphic site. The labeled terminator that is incorporated is thus determined by, and complementary to, the nucleotide present in the polymorphic site of the target molecule being evaluated. In contrast to the method of Cohen et al. (French Patent 2,650,840; PCT Appln. No. WO91/02087) the method of Goelet, P. et al. is preferably a heterogeneous phase assay, in which the primer or the target molecule is immobilized to a solid phase.

Recently, several primer-guided nucleotide incorporation procedures for assaying polymorphic sites in DNA have been described (Komher, J. S. et al., Nucl. Acids. Res. 17:7779–7784 (1989); Sokolov, B. P., Nucl. Acids Res. 18:3671 (1990); Syvanen, A. -C., et al., Genomics 8:684–692 (1990); Kuppuswamy, M. N. et al., Proc. Natl. Acad. Sci. (U.S.A.) 88:1143–1147 (1991); Prezant, T. R. et al., Hum. Mutat. 1:159–164 (1992); Ugozzoli, L. et al., GATA 9:107–112 (1992); Nyren, P. et al., Anal. Biochem. 208:171–175 (1993)). These methods differ from GBA™ in that they all rely on the incorporation of labeled deoxynucleotides to discriminate between bases at a polymorphic site. In such a format, since the signal is proportional to the number of deoxynucleotides incorporated, polymorphisms that occur in runs of the same nucleotide can result in signals that are proportional to the length of the run (Syvanen, A. -C., et al., Amer. J. Hum. Genet. 52:46–59 (1993)).

For mutations that produce premature termination of protein translation, the protein truncation test (PTT) offers an efficient diagnostic approach (Roest, et. al., (1993) *Hum. Mol. Genet.* 2:1719–21; van der Luijt, et. al., (1994) *Genomics* 20:1–4). For PTT, RNA is initially isolated from available tissue and reverse-transcribed, and the segment of interest is amplified by PCR. The products of reverse transcription PCR are then used as a template for nested PCR amplification with a primer that contains an RNA polymerase promoter and a sequence for initiating eukaryotic translation. After amplification of the region of interest, the unique motifs incorporated into the primer permit sequential in vitro transcription and translation of the PCR products. Upon sodium dodecyl sulfate-polyacrylamide gel electrophoresis of translation products, the appearance of truncated polypeptides signals the presence of a mutation that causes premature termination of translation. In a variation of this technique, DNA (as opposed to RNA) is used as a PCR template when the target region of interest is derived from a single exon.

Any cell type or tissue may be utilized to obtain nucleic acid samples for use in the diagnostics described herein. In a preferred embodiment, the DNA sample is obtained from a bodily fluid, e.g, blood, obtained by known techniques (e.g. venipuncture) or saliva. Alternatively, nucleic acid tests can be performed on dry samples (e.g. hair or skin). When using RNA or protein, the cells or tissues that may be utilized must express an IL-1 gene.

Diagnostic procedures may also be performed in situ directly upon tissue sections (fixed and/or frozen) of patient tissue obtained from biopsies or resections, such that no nucleic acid purification is necessary. Nucleic acid reagents may be used as probes and/or primers for such in situ procedures (see, for example, Nuovo, G. J., 1992, PCR in situ hybridization: protocols and applications, Raven Press, N.Y.).

In addition to methods which focus primarily on the detection of one nucleic acid sequence, profiles may also be assessed in such detection schemes. Fingerprint profiles may be generated, for example, by utilizing a differential display procedure, Northern analysis and/or RT-PCR.

A preferred detection method is allele specific hybridization using probes overlapping a region of an allele and having about 5, 10, 20, 25, or 30 nucleotides around the mutation or polymorphic region. In a preferred embodiment of the invention, several probes capable of hybridizing specifically to other allelic variants involved in asthma are attached to a solid phase support, e.g., a "chip" (which can hold up to about 250,000 oligonucleotides). Oligonucleotides can be bound to a solid support by a variety of processes, including lithography. Mutation detection analysis using these chips comprising oligonucleotides, also termed "DNA probe arrays" is described e.g., in Cronin et al. (1996) Human Mutation 7:244. In one embodiment, a chip comprises all the allelic variants of at least one polymorphic region of a gene. The solid phase support is then contacted with a test nucleic acid and hybridization to the specific probes is detected. Accordingly, the identity of numerous allelic variants of one or more genes can be identified in a simple hybridization experiment.

These techniques may also comprise the step of amplifying the nucleic acid before analysis. Amplification techniques are known to those of skill in the art and include, but are not limited to cloning, polymerase chain reaction (PCR), polymerase chain reaction of specific alleles (ASA), ligase chain reaction (LCR), nested polymerase chain reaction, self sustained sequence replication (Guatelli, J. C. et al., 1990, Proc. Natl. Acad. Sci. USA 87:1874–1878), transcriptional amplification system (Kwoh, D. Y. et al., 1989, Proc. Natl. Acad. Sci. USA 86:1173–1177), and Q-Beta Replicase (Lizardi, P. M. et al., 1988, Bio/Technology 6:1197).

Amplification products may be assayed in a variety of ways, including size analysis, restriction digestion followed by size analysis, detecting specific tagged oligonucleotide primers in the reaction products, allele-specific oligonucleotide (ASO) hybridization, allele specific 5' exonuclease detection, sequencing, hybridization, and the like.

PCR based detection means can include multiplex amplification of a plurality of markers simultaneously. For example, it is well known in the art to select PCR primers to generate PCR products that do not overlap in size and can be analyzed simultaneously. Alternatively, it is possible to amplify different markers with primers that are differentially labeled and thus can each be differentially detected. Of course, hybridization based detection means allow the differential detection of multiple PCR products in a sample. Other techniques are known in the art to allow multiplex analyses of a plurality of markers.

In a merely illustrative embodiment, the method includes the steps of (i) collecting a sample of cells from a patient, (ii) isolating nucleic acid (e.g., genomic, mRNA or both) from the cells of the sample, (iii) contacting the nucleic acid sample with one or more primers which specifically hybridize 5' and 3' to an appropriate allele under conditions such that hybridization and amplification of the allele occurs, and (iv) detecting the amplification product. These detection schemes are especially useful for the detection of nucleic acid molecules if such molecules are present in very low numbers.

In a preferred embodiment of the subject assay, the allele is identified by alterations in restriction enzyme cleavage patterns. For example, sample and control DNA can be isolated, amplified (optionally), digested with one or more restriction endonucleases, and fragment length sizes are determined by gel electrophoresis.

In yet another embodiment, any of a variety of sequencing reactions known in the art can be used to directly sequence the allele. Exemplary sequencing reactions include those based on techniques developed by Maxim and Gilbert ((1977) Proc. Natl Acad Sci USA 74:560) or Sanger (Sanger et al (1977) Proc. Nat. Acad. Sci USA 74:5463). It is also contemplated that any of a variety of automated sequencing procedures may be utilized when performing the subject assays (see, for example Biotechniques (1995) 19:448), including sequencing by mass spectrometry (see, for example PCT publication WO 94/16101; Cohen et al. (1996) Adv Chromatogr 36:127–162; and Griffin et al. (1993) Appl Biochem Biotechnol 38:147–159). It will be evident to one of skill in the art that, for certain embodiments, the occurrence of only one, two or three of the nucleic acid bases need be determined in the sequencing reaction. For instance, A-track or the like, e.g., where only one nucleic acid is detected, can be carried out.

In a further embodiment, protection from cleavage agents (such as a nuclease, hydroxylamine or osmium tetroxide and with piperidine) can be used to detect mismatched bases in RNA/RNA or RNA/DNA or DNA/DNA heteroduplexes (Myers, et al. (1985) Science 230:1242). In general, the art technique of "mismatch cleavage" starts by providing heteroduplexes formed by hybridizing (labeled) RNA or DNA containing the wild-type allele with the sample. The double-stranded duplexes are treated with an agent which cleaves single-stranded regions of the duplex such as which will exist due to base pair mismatches between the control and sample strands. For instance, RNA/DNA duplexes can be treated with RNase and DNA/DNA hybrids treated with S1 nuclease to enzymatically digest the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, for example, Cotton et al (1988) Proc. Natl Acad Sci USA 85:4397; and Saleeba et al (1992) Methods Enzymol. 217:286–295. In a preferred embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes). For example, the mutY enzyme of E. coli cleaves A at G/A mismatches and the thymidine DNA glycosylase from HeLa cells cleaves T at G/T mismatches (Hsu et al. (1994) Carcinogenesis 15:1657–1662). According to an exemplary embodiment, a probe based on an allele of an IL-1 locus haplotype is hybridized to a cDNA or other DNA product from a test cell(s). The duplex is treated with a DNA mismatch repair enzyme, and the cleavage products, if any, can be detected from electrophoresis protocols or the like. See, for example, U.S. Pat. No. 5,459,039.

In other embodiments, alterations in electrophoretic mobility will be used to identify an IL-1 locus allele. For example, single strand conformation polymorphism (SSCP) may be used to detect differences in electrophoretic mobility between mutant and wild type nucleic acids (Orita et al. (1989) Proc Natl. Acad. Sci USA 86:2766, see also Cotton (1993) Mutat Res 285:125–144; and Hayashi (1992) Genet Anal Tech Appl 9:73–79). Single-stranded DNA fragments of sample and control IL-1 locus alleles are denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) Trends Genet 7:5).

In yet another embodiment, the movement of alleles in polyacrylamide gels containing a gradient of denaturant is assayed using denaturing gradient gel electrophoresis (DGGE) (Myers et al. (1985) Nature 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing agent gradient to identify differences in the mobility of control and sample DNA (Rosenbaum and Reissner (1987) Biophys Chem 265:12753).

Examples of other techniques for detecting alleles include, but are not limited to, selective oligonucleotide hybridization, selective amplification, or selective primer extension. For example, oligonucleotide primers may be prepared in which the known mutation or nucleotide difference (e.g., in allelic variants) is placed centrally and then hybridized to target DNA under conditions which permit hybridization only if a perfect match is found (Saiki et al. (1986) Nature 324:163); Saiki et al (1989) Proc. Natl Acad. Sci USA 86:6230). Such allele specific oligonucleotide hybridization techniques may be used to test one mutation or polymorphic region per reaction when oligonucleotides are hybridized to PCR amplified target DNA or a number of different mutations or polymorphic regions when the oligonucleotides are attached to the hybridizing membrane and hybridized with labelled target DNA.

Alternatively, allele specific amplification technology which depends on selective PCR amplification may be used in conjunction with the instant invention. Oligonucleotides used as primers for specific amplification may carry the mutation or polymorphic region of interest in the center of the molecule (so that amplification depends on differential hybridization) (Gibbs et al (1989) Nucleic Acids Res. 17:2437–2448) or at the extreme 3' end of one primer where, under appropriate conditions, mismatch can prevent, or reduce polymerase extension (Prossner (1993) Tibtech 11:238. In addition it may be desirable to introduce a novel restriction site in the region of the mutation to create cleavage-based detection (Gasparini et al (1992) Mol. Cell Probes 6:1). It is anticipated that in certain embodiments amplification may also be performed using Taq ligase for amplification (Barany (1991) Proc. Natl. Acad. Sci USA 88:189). In such cases, ligation will occur only if there is a perfect match at the 3' end of the 5' sequence making it possible to detect the presence of a known mutation at a specific site by looking for the presence or absence of amplification.

In another embodiment, identification of the allelic variant is carried out using an oligonucleotide ligation assay (OLA), as described, e.g., in U.S. Pat. No. 4,998,617 and in Landegren, U. et al. ((1988) Science 241:1077–1080). The OLA protocol uses two oligonucleotides which are designed to be capable of hybridizing to abutting sequences of a single strand of a target. One of the oligonucleotides is linked to a separation marker, e.g., biotinylated, and the other is detectably labeled. If the precise complementary sequence is found in a target molecule, the oligonucleotides will hybridize such that their termini abut, and create a ligation substrate. Ligation then permits the labeled oligonucleotide to be recovered using avidin, or another biotin ligand. Nickerson, D. A. et al. have described a nucleic acid detection assay that combines attributes of PCR and OLA (Nickerson, D. A. et al. (1990) Proc. Natl. Acad. Sci. USA 87:8923–27). In this method, PCR is used to achieve the exponential amplification of target DNA, which is then detected using OLA.

Several techniques based on this OLA method have been developed and can be used to detect alleles. For example, U.S. Pat. No. 5,593,826 discloses an OLA using an oligonucleotide having 3'-amino group and a 5'-phosphorylated oligonucleotide to form a conjugate having a phosphoramidate linkage. In another variation of OLA described in Tobe et al. ((1996) Nucleic Acids Res 24: 3728), OLA combined with PCR permits typing of two alleles in a single microtiter well. By marking each of the allele-specific primers with a unique hapten, i.e. digoxigenin and fluorescein, each OLA reaction can be detected by using hapten specific antibodies that are labeled with different enzyme reporters, alkaline phosphatase or horseradish peroxidase. This system permits the detection of the two alleles using a high throughput format that leads to the production of two different colors.

Another embodiment of the invention is directed to kits for detecting a predisposition for developing a chronic obstructive airway disease or for developing a severe form of the disease. This kit may contain one or more oligonucleotides, including 5' and 3' oligonucleotides that hybridize 5' and 3' to at least one allele of an IL-1 locus haplotype. PCR amplification oligonucleotides should hybridize between 25 and 2500 base pairs apart, preferably between about 100 and about 500 bases apart, in order to produce a PCR product of convenient size for subsequent analysis.

The design of additional oligonucleotides for use in the amplification and detection of IL-1 polymorphic alleles by the method of the invention is facilitated by the availability of both updated sequence information from human chromosome 2q13—which contains the human IL-1 locus, and updated human polymorphism information available for this locus. For example, the DNA sequence for the IL-1A, IL-1B, IL-1RN and IL-13 genes are shown in FIGS. 1–4 respectively. Suitable primers for the detection of a human polymorphism in these genes can be readily designed using this sequence information and standard techniques known in the art for the design and optimization of primers sequences. Optimal design of such primer sequences can be achieved, for example, by the use of commercially available primer selection programs such as Primer 2.1, Primer 3 or GeneFisher (See also, Nicklin M. H. J., Weith A. Duff G. W., "A Physical Map of the Region Encompassing the Human Interleukin-1α, interleukin-1β, and Interleukin-1 Receptor Antagonist Genes" Genomics 19: 382 (1995); Nothwang H. G., et al. "Molecular Cloning of the Interleukin-1 gene Cluster: Construction of an Integrated YAC/PAC Contig and a partial transcriptional Map in the Region of Chromosome 2q13" Genomics 41: 370 (1997); Clark, et al. (1986) Nucl. Acids. Res., 14:7897–7914 [published erratum appears in Nucleic Acids Res., 15:868 (1987) and the Genome Database (GDB) project at the URL http://www.gdb.org).

For use in a kit, oligonucleotides may be any of a variety of natural and/or synthetic compositions such as synthetic oligonucleotides, restriction fragments, cDNAs, synthetic peptide nucleic acids (PNAs), and the like. The assay kit and method may also employ labeled oligonucleotides to allow ease of identification in the assays. Examples of labels which may be employed include radio-labels, enzymes, fluorescent compounds, streptavidin, avidin, biotin, magnetic moieties, metal binding moieties, antigen or antibody moieties, and the like.

The kit may, optionally, also include DNA sampling means. DNA sampling means are well known to one of skill in the art and can include, but not be limited to substrates, such as filter papers, the AmpliCard™ (University of Sheffield, Sheffield, England S10 2JF; Tarlow, J W, et al., *J. of Invest. Dermatol.* 103:387–389 (1994)) and the like; DNA purification reagents such as Nucleon™ kits, lysis buffers, proteinase solutions and the like; PCR reagents, such as 10×reaction buffers, thermostable polyrnerase, dNTPs, and the like; and allele detection means such as the HinfI restriction enzyme, allele specific oligonucleotides, degenerate oligonucleotide primers for nested PCR from dried blood.

4.2.3. Pharmacogenomics

Knowledge of the particular alleles associated with a susceptibility to developing a particular disease or condition, alone or in conjunction with information on other genetic defects contributing to the particular disease or condition allows a customization of the prevention or treatment in accordance with the individual's genetic profile, the goal of "pharmacogenomics". Thus, comparison of an individual's IL-1 profile to the population profile for an obstructive airway disease, permits the selection or design of drugs or other therapeutic regimens that are expected to be safe and efficacious for a particular patient or patient population (i.e., a group of patients having the same genetic alteration).

In addition, the ability to target populations expected to show the highest clinical benefit, based on genetic profile can enable: 1) the repositioning of already marketed drugs; 2) the rescue of drug candidates whose clinical development has been discontinued as a result of safety or efficacy limitations, which are patient subgroup-specific; and 3) an accelerated and less costly development for candidate therapeutics and more optimal drug labeling (e.g. since measuring the effect of various doses of an agent on the causative mutation is useful for optimizing effective dose).

The treatment of an individual with a particular therapeutic can be monitored by determining protein (e.g. IL-1α, IL-1β, IL-1Ra, IL-13), mRNA and/or transcriptional level. Depending on the level detected, the therapeutic regimen can then be maintained or adjusted (increased or decreased in dose). In a preferred embodiment, the effectiveness of treating a subject with an agent comprises the steps of: (i) obtaining a preadministration sample from a subject prior to administration of the agent; (ii) detecting the level or amount of a protein, mRNA or genomic DNA in the preadministration sample; (iii) obtaining one or more post-administration samples from the subject; (iv) detecting the level of expression or activity of the protein, mRNA or genomic DNA in the post-administration sample; (v) comparing the level of expression or activity of the protein, mRNA or genomic DNA in the preadministration sample with the corresponding protein, mRNA or genomic DNA in the postadministration sample, respectively; and (vi) altering the administration of the agent to the subject accordingly.

Cells of a subject may also be obtained before and after administration of a therapeutic to detect the level of expression of genes other than an interleukin gene to verify that the therapeutic does not increase or decrease the expression of genes which could be deleterious. This can be done, e.g., by using the method of transcriptional profiling. Thus, mRNA from cells exposed in vivo to a therapeutic and mRNA from the same type of cells that were not exposed to the therapeutic could be reverse transcribed and hybridized to a chip containing DNA from numerous genes, to thereby compare the expression of genes in cells treated and not treated with the therapeutic.

4.3 Therapeutics for Obstructive Airway Diseases

An "OAD therapeutic" refers to any agent or therapeutic regimen (including pharmaceuticals, nutraceuticals and surgical means) that prevents or postpones the development of or alleviates the symptoms of an OAD in a subject. The therapeutic can be a polypeptide, peptidomimetic, nucleic acid or other inorganic or organic molecule, preferably a "small molecule" including vitamins, minerals and other nutrients. Preferably the therapeutic can modulate at least one activity of an interleukin polypeptide, e.g., interaction with a receptor, by mimicking or potentiating (agonizing) or inhibiting (antagonizing) the effects of a naturally-occurring polypeptide. An agonist can be a wild-type protein or derivative thereof having at least one bioactivity of the wild-type, e.g., receptor binding activity. An agonist can also be a compound that upregulates expression of a gene or which increases at least one bioactivity of a protein. An agonist can also be a compound which increases the interaction of a polypeptide with another molecule, e.g., a receptor. An antagonist can be a compound which inhibits or decreases the interaction between a protein and another molecule, e.g., a receptor or an agent that blocks signal transduction or post-translation processing (e.g., IL-1 converting enzyme (ICE) inhibitor). Accordingly, a preferred antagonist is a compound which inhibits or decreases binding to a receptor and thereby blocks subsequent activation of the receptor. An antagonist can also be a compound that downregulates expression of a gene or which reduces the amount of a protein present. The antagonist can be a dominant negative form of a polypeptide, e.g., a form of a polypeptide which is capable of interacting with a target peptide, e.g., a receptor, but which does not promote the activation of the receptor. The antagonist can also be a nucleic acid encoding a dominant negative form of a polypeptide, an antisense nucleic acid, or a ribozyme capable of interacting specifically with an RNA. Yet other antagonists are molecules which bind to a polypeptide and inhibit its action. Such molecules include peptides, e.g., forms of target peptides which do not have biological activity, and which inhibit binding to receptors. Thus, such peptides will bind to the active site of a protein and prevent it from interacting with target peptides. Yet other antagonists include antibodies that specifically interact with an epitope of a molecule, such that binding interferes with the biological function of the polypeptide. In yet another preferred embodiment, the antagonist is a small molecule, such as a molecule capable of inhibiting the interaction between a polypeptide and a target receptor. Alternatively, the small molecule can function as an antagonist by interacting with sites other than the receptor binding site. Agents for treating asthma (both chronic and acute) include: steroid inhalers (such as beclomethasone diproprionate, budesonide, flunisolide, fluticasone proprionate, triamcinolone and acetonide); cromolyn sodium and nedocromil, long acting beta-2 agonists (such as salmeterol, formoterol and albuterol), methylxanthines (such as theophylline and mepyramine-theophylline acetate), leukotriene modifiers (such as zafirlukast, zileuton, montekulast and pranlukast), quick relief beta-2 agonists (such as albuterol, bitolterol, pirbuterol, terbutaline and bambuterol), anticholinergics (such as ipatropium bromide), systemic corticosteroids (such as methylprednisolone, prednisolone, prednisone and deflazacort) and experimental agents (including monoclonal antibodies directed against intracellular adhesion molecules or IgE), thromboxane A2 synthetase inhibitors (OKY-046), thromboxane prostanoid receptor antagonists (S-1452), other eicosanoid modifiers (alprostadil vs. PGE1, dinoprostone vs. PGE2, epoprostenol vs. prostacyclin and PGI2 analogues (e.g. PG12 beraprost), seratrodast (e.g.AA-2414), ozagrel (OKY-046)), phosphodiesterase 4 isoenzyme inhibitors, thromboxane A2 synthetase inhibitors (e.g. azelastine), ditec (low dose disodium cromoglycate and fenoterol), platelet activating factor receptor antagonists (Y-24180), antihistamines, anti-thromboxane A2 (SWR- 00151), antibradykinins (such as icatibant), agents that inhibit activated eosinophils and T-cell recruitment (e.g. ketotifen), IL-13 blockers (such as soluble IL-13 receptor fragments), IL-4 blockers (such as soluble IL-4 receptor fragments), ligands that bind and block the activity of IL-13 or IL-4, and xanthine derivatives (such as pentoxifyolline and A802715).

4.3.1. Effective Dose

Toxicity and therapeutic efficacy of such compounds can be determined by standard pharmaceutical procedures in cell cultures or experimental animals, e.g., for determining The $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. While compounds that exhibit toxic side effects may be used, care should be taken to design a delivery system that targets such compounds to the site of affected tissues in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

4.3.2. Formulation and Use

Compositions for use in accordance with the present invention may be formulated in a conventional manner using one or more physiologically acceptable carriers or excipients. Thus, the compounds and their physiologically acceptable salts and solvates may be formulated for administration by, for example, injection, inhalation or insufflation (either through the mouth or the nose) or oral, buccal, parenteral or rectal administration.

For such therapy, the compounds of the invention can be formulated for a variety of loads of administration, including systemic and topical or localized administration. Techniques and formulations generally may be found in Remmington's Pharmaceutical Sciences, Meade Publishing Co., Easton, Pa. For systemic administration, injection is preferred, including intramuscular, intravenous, intraperitoneal, and subcutaneous. For injection, the compounds of the invention can be formulated in liquid solutions, preferably in physiologically compatible buffers such as Hank's solution or Ringer's solution. In addition, the compounds may be formulated in solid form and redissolved or suspended immediately prior to use. Lyophilized forms are also included.

For oral administration, the compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulfate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., ationd oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

Preparations for oral administration may be suitably formulated to give controlled release of the active compound. For buccal administration the compositions may take the form of tablets or lozenges formulated in conventional manner. For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulating agents such as suspending, stabilizing and/or dispersing agents. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt. Other suitable delivery systems include microspheres which offer the possibility of local noninvasive delivery of drugs over an extended period of time. This technology utilizes microspheres of precapillary size which can be injected via a coronary catheter into any selected part of the e.g. heart or other organs without causing inflammation or ischemia. The administered therapeutic is slowly released from these microspheres and taken up by surrounding tissue cells (e.g. endothelial cells).

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration bile salts and fusidic acid derivatives. In addition, detergents may be used to facilitate permneation. Transmucosal administration may be through nasal sprays or using suppositories. For topical administration, the oligomers of the invention are formulated into ointments, salves, gels, or creams as generally known in the art. A wash solution can be used locally to treat an injury or inflammation to accelerate healing.

The compositions may, if desired, be presented in a pack or disp enser device which may contain one or more unit dosage forms containing the active ingredient. The pack may for example comprise metal or plastic foil, such as a blister pack. The pack or dispenser device may be accompanied by in s tructions for administration.

4.4 Assays to Identify Therapeutics

Based on the identification of mutations that cause or contribute to the development of an obstructive airway disease, the invention further features cell-based or cell free assays for identifying therapeutics. In one embodiment, a cell expressing an IL-1 or IL-13 receptor, or a receptor for a protein that is encoded by a gene which is in linkage disequilibrium with an IL-1 or IL-13 gene, on the outer surface of its cellular membrane is incubated in the presence of a test compound alone or in the presence of a test compound and another protein and the interaction between the test compound and the receptor or between the protein (preferably a tagged protein) and the receptor is detected, e.g., by using a microphysiometer (McConnell et al. (1992) Science 257:1906). An interaction between the receptor and either the test compound or the protein is detected by the microphysiometer as a change in the acidification of the medium. This assay system thus provides a means of identifying molecular antagonists which, for example, function by interfering with protein-receptor interactions, as well as molecular agonist which, for example, function by activating a receptor.

Cellular or cell-free assays can also be used to identify compounds which modulate expression of an IL-1 or IL-13 gene or a gene in linkage disequilibrium therewith, modulate translation of an mRNA, or which modulate the stability of an mRNA or protein. Accordingly, in one embodiment, a cell which is capable of producing an IL-1 or IL-13, or other protein is incubated with a test compound and the amount of protein produced in the cell medium is measured and compared to that produced from a cell which has not been contacted with the test compound. The specificity of the compound vis a vis the protein can be confirmed by various control analysis, e.g., measuring the expression of one or more control genes. In particular, this assay can be used to determine the efficacy of antisense, ribozyme and triplex compounds.

Cell-free assays can also be used to identify compounds which are capable of interacting with a protein, to thereby modify the activity of the protein. Such a compound can, e.g., modify the structure of a protein thereby effecting its ability to bind to a receptor. In a preferred embodiment, cell-free assays for identifying such compounds consist essentially in a reaction mixture containing a protein and a test compound or a library of test compounds in the presence or absence of a binding partner. A test compound can be, e.g., a derivative of a binding partner, e.g., a biologically inactive target peptide, or a small molecule.

Accordingly, one exemplary screening assay of the present invention includes the steps of contacting a protein or functional fragment thereof with a test compound or library of test compounds and detecting the formation of complexes. For detection purposes, the molecule can be labeled with a specific marker and the test compound or library of test compounds labeled with a different marker. Interaction of a test compound with a protein or fragment thereof can then be detected by determining the level of the two labels after an incubation step and a washing step. The presence of two labels after the washing step is indicative of an interaction.

An interaction between molecules can also be identified by using real-time BIA (Biomolecular Interaction Analysis, Pharmacia Biosensor AB) which detects surface plasmon resonance (SPR), an optical phenomenon. Detection depends on changes in the mass concentration of macromolecules at the biospecific interface, and does not require any labeling of interactants. In one embodiment, a library of test compounds can be immobilized on a sensor surface, e.g., which forms one wall of a micro-flow cell. A solution containing the protein or fimctional fragment thereof is then flown continuously over the sensor surface. A change in the resonance angle as shown on a signal recording, indicates that an interaction has occurred. This technique is further described, e.g., in BIAtechnology Handbook by Pharmacia.

Another exemplary screening assay of the present invention includes the steps of (a) forming a reaction mixture including: (i) an IL-1, IL-13 or other protein, (ii) an appropriate receptor, and (iii) a test compound; and (b) detecting interaction of the protein and receptor. A statistically significant change potentiation or inhibition) in the interaction of the protein and receptor in the presence of the test compound, relative to the interaction in the absence of the test compound, indicates a potential antagonist (inhibitor). The compounds of this assay can be contacted simultaneously. Alternatively, a protein can first be contacted with a test compound for an appropriate amount of time, following which the receptor is added to the reaction mixture. The efficacy of the compound can be assessed by generating dose response curves from data obtained usog various concentrations of the test compound. Moreover, a control assay can also be performed to provide a baseline for comparison.

Complex formation between a protein and receptor may be detected by a variety of techniques. Modulation of the formation of complexes can be quantitated using, for example, delectably labeled proteins such as radiolabeled, fluorescently labeled, or enzymatically labeled proteins or receptors, by immunoassay, or by chromatographic detection.

Typically, it will be desirable to immobilize either the protein or the receptor to facilitate separation of complexes from uncomplexed forms of one or both of the proteins, as well as to accommodate automation of the assay. Binding of protein and receptor can be accomplished in any vessel suitable for containing the reactants. Examples include microtitre plates, test tubes, and micro-centrifuge tubes. In one embodiment, a fusion protein can be provided which adds a domain that aollow the protein to be bound to a matrix. For exiaple, glutathione-S-transferase fusion proteins can be adsorbed onto glutathione sepharose beads (Sigma Chemical, St. Louis, Mo.) or glutathione derivatized microtitre plates, which are then combined with the receptor, e.g. an $^{35}$S-labeled receptor, and the test compound, and the mixture incubated under conditions conducive to complex formation, e.g. at physiological conditions for salt and pH, though slightly more stringent conditions may be desired. Following incubation, the beads are washed to remove any unbound label, and the matrix immobilized and radiolabel determined directly (e.g. beads placed in scintillant), or in the supefatant after the complexes are subsequently dissociated. Alternatively, the complexes can be dissociated from the matrix, separated by SDS-PAGE, and the level of protein or receptor found in the bead fraction quantitated from the gel using standard electrophoretic techniques such as described in the appended examples. Other techniques for immobilizing proteins on matrices are also available for use in the subject assay. For instance, either protein or receptor can be immobilized utilizing conjugation of biotin and streptavidin. Transgenic animals can also be made to identify agonists and antagonists or to confirm the safety and efficacy of a candidate therapeutic. Transgenic animals of the invention can include non-human animals containing a restenosis causative mutation under the control of an appropriate endogenous promoter or under the control of a heterologous promoter.

The transgenic animals can also be animals containing a transgene, such as reporter gene, under the control of an appropriate promoter or fragment thereof. These animals are useful, e.g., for identifying drugs that modulate production of an IL-1 protein, such as by modulating gene expression. Methods for obtaining transgenic non-human animals are well known in the art. In preferred embodiments, the expression of the restenosis causative mutation is restricted to specific subsets of cells, tissues or developmental stages utilizing, for example, cis-acting sequences that control expression in the desired pattern. In the present invention, such mosaic expression of a protein can be essential for many forms of lineage analysis and can additionally provide a means to assess the effects of, for example, expression level which might grossly alter development in small patches of tissue within an otherwise normal embryo. Toward this end, tissue-specific regulatory sequences and conditional regulatory sequences can be used to control expression of the mutation in certain spatial patterns. Moreover, temporal patterns of expression can be provided by, for example, conditional recombination systems or prokaryotic transcriptional regulatory sequences. Genetic techniques, which allow for the expression of a mutation can be regulated via site-specific genetic manipulation in vivo, are known to those skilled in the art.

The transgenic animals of the present invention all include within a plurality of their cells a causative mutation transgene of the present invention, which transgene alters the phenotype of the "host cell". In an illustrative embodiment, either the cre/loxP recombinase system of bacteriophage P1 (Lakso et al. (1992) *PNAS* 89:6232–6236; Orban et al. (1992) *PNAS* 89:6861–6865) or the FLP recombinase system of *Saccharomyces cerevisiae* (O'Gorman et al. (1991) *Science* 251:1351–1355; PCT publication WO 92/15694) can be used to generate in vivo site-specific genetic recombination systems. Cre recombinase catalyzes the site-specific recombination of an intervening target sequence located between loxP sequences. loxP sequences are 34 base pair nucleotide repeat sequences to which the Cre recombinase binds and are required for Cre recombinase mediated genetic recombination. The orientation ofloxP sequences determines whether the intervening target sequence is exised or inverted when Cre recombinase is present (Abremski et al. (1984) *J. Biol. Chem.* 259:1509–1514); catalyzing the excision of the target sequence when the loxP sequences are oriented as direct repeats and catalyzes inversion of the target sequence when loxP sequences are oriented as inverted repeats.

Accordingly, genetic recombination of the target sequence is dependent on expression of the Cre recombinase. Expression of the recombinase can be regulated by promoter elements which are subject to regulatory control, e.g., tissue-specific, developmental stage-specific, inducible or repressible by externally added agents. This regulated control will result in genetic recombination of the target sequence only in cells where recombinase expression is mediated by the promoter element. Thus, the activation of expression of the causative mutation transgene can be regulated via control of recombinase expression.

Use of the cre/loxP recombinase system to regulate expression of a causative mutation transgene requires the construction of a tasgenicanimal containing transgenes encoding both the Cre recombinase and the subject protein. Animals containing both the Cre recombinase and the restenosis causative mutation transgene can be provided through the construction of "double" transgenic animals. A convenient method for providing such animals is to mate two transgenic animals each containing a transgene.

Similar conditional transgenes can be provided using prokaryotic promoter sequences which require prokaryotic proteins to be simultaneous expressed in order to facilitate expression of the tasgene. Exemplary promoters and the corresponding ers activating prokaryotic proteins are given in U.S. Pat. No. 4,833,080.

Moreover, expression of the conditional transgenes can be induced by gene therapy-like methods wherein a gene encoding the transactivating protein, e.g. a recombinase or a prokaryotic protein, is delivered to the tissue and caused to be expressed, such as in a cell-type specific manner. By this method, the transgene could remain silent into adulthood until "turned on" by the introduction of the transactivator.

In an exemplary embodiment, the "transgenic non-human animals" of the invention are produced by introducing transgenes into the germline of the non-human animal. Embryonal target cells at various developmental stages can be used to introduce transgenes. Different methods are used depending on the stage of development of the embryonal target cell. The specific line(s) of any animal used to practice this invention are selected for general good health, good embryo yields, good pronuclear visibility in the embryo, and good reproductive fitness. In addition, the haplotype is a significant factor. For example, when transgenic mice are to be produced, strains such as C57BL/6 or FVB lines are often used (Jackson Laboratory, Bar Harbor, Me.). Preferred strains are those with H-$2^b$, H-$2^d$ or H-2q haplotypes such as C57BL/6 or DBA/1. The line(s) used to practice this invention may themselves be transgenics, and/or may be knockouts (i.e., obtained from animals which have one or more genes partially or completely suppressed).

In one embodiment, the transgene construct is introduced into a single stage embryo. The zygote is the best target for microinjection. In the mouse, the male pronucleus reaches the size of approximately 20 micrometers in diameter which allows reproducible injection of 1–2 pl of DNA solution. The use of zygotes as a target for gene transfer has a major advantage in that in most cases the injected DNA will be incorporated into the host gene before the first cleavage (Brinster et al. (1985) *PNAS* 82:4438–4442). As a consequence, all cells of the transgenic animal will carry the incorporated transgene. This will in general also be reflected in the efficient transmission of the transgene to offspring of the founder since 50% of the germ cells will harbor the transgene.

Normally, fertilized embryos are incubated in suitable media until the pronuclei appear. At about this time, the nucleotide sequence comprising the transgene is introduced into the female or male pronucleus as described below. In some species such as mice, the male pronucleus is preferred. It is most preferred that the exogenous genetic material be added to the male DNA complement of the zygote prior to its being processed by the ovum nucleus or the zygote female pronucleus. It is thought that the ovum nucleus or female pronucleus release molecules which affect the male DNA complement, perhaps by replacing the protamines of the male DNA with histones, thereby facilitating the combination of the female and male DNA complements to form the diploid zygote. Thus, it is preferred that the exogenous genetic material be added to the male complement of DNA or any other complement of DNA prior to its being affected by the female pronucleus. For example, the exogenous genetic material is added to the early male pronucleus, as soon as possible after the formation of the male pronucleus, which is when the male and female pronuclei are well separated and both are located close to the cell membrane. Alternatively, the exogenous genetic material could be added to the nucleus of the sperm after it has been induced to undergo decondensation. Sperm containing the exogenous genetic material can then be added to the ovum or the decondensed sperm could be added to the ovum with the transgene constructs being added as soon as possible thereafter.

Introduction of the transgene nucleotide sequence into the embryo may be accomplished by any means known in the art such as, for example, microinjection, electroporation, or lipofection. Following introduction of the transgene nucleotide sequence into the embryo, the embryo may be incubated in vitro for varying amounts of time, or reimplanted into the surrogate host, or both. In vitro incubation to maturity is within the scope of this invention. One common method in to incubate the embryos in vitro for about 1–7 days, depending on the species, and then reimplant them into the surrogate host.

For the purposes of this invention a zygote is essentially the formation of a diploid cell which is capable of developing into a complete organism. Generally, the zygote will be comprised of an egg containing a nucleus formed, either naturally or artificially, by the fusion of two haploid nuclei from a gamete or gametes. Thus, the gamete nuclei must be ones which are naturally compatible, i.e., ones which result in a viable zygote capable of undergoing differentiation and developing into a functioning organism. Generally, a euploid zygote is preferred. If an aneuploid zygote is obtained, then the number of chromosomes should not vary by more than one with respect to the euploid number of the organism from which either gamete originated.

In addition to similar biological considerations, physical ones also govern the amount (e.g., volume) of exogenous genetic material which can be added to the nucleus of the zygote or to the genetic material which forms a part of the zygote nucleus. If no genetic material is removed, then the amount of exogenous genetic material which can be added is limited by the amount which will be absorbed without being physically disruptive. Generally, the volume of exogenous genetic material inserted will not exceed about 10 picoliters. The physical effects of addition must not be so great as to physically destroy the viability of the zygote. The biological limit of the number and variety of DNA sequences will vary depending upon the particular zygote and functions of the exogenous genetic material and will be readily apparent to one skilled in the art, because the genetic material, including the exogenous genetic material, of the resulting zygote must be biologically capable of initiating and maintaining the differentiation and development of the zygote into a functional organism.

The number of copies of the transgene constructs which are added to the zygote is dependent upon the total amount of exogenous genetic material added and will be the amount which enables the genetic transformation to occur. Theoretically only one copy is required; however, generally, numerous copies are utilized, for example, 1,000–20,000 copies of the transgene construct, in order to insure that one copy is functional. As regards the present invention, there will often be an advantage to having more than one functioning copy of each of the inserted exogenous DNA sequences to enhance the phenotypic expression of the exogenous DNA sequences.

Any technique which allows for the addition of the exogenous genetic material into nucleic genetic material can be utilized so long as it is not destructive to the cell, nuclear membrane or other existing cellular or genetic structures. The exogenous genetic material is preferentially inserted into the nucleic genetic material by microinjection. Microinjection of cells and cellular structures is known and is used in the art.

Reimplantation is accomplished using standard methods. Usually, the surrogate host is anesthetized, and the embryos are inserted into the oviduct. The number of embryos implanted into a particular host will vary by species, but will usually be comparable to the number of off spring the species naturally produces.

Transgenic offspring of the surrogate host may be screened for the presence and/or expression of the transgene by any suitable method. Screening is often accomplished by Southern blot or Northern blot analysis, using a probe that is complementary to at least a portion of the transgene. Western blot analysis using an antibody against the protein encoded by the transgene may be employed as an alternative or additional method for screening for the presence of the transgene product. Typically, DNA is prepared from tail tissue and analyzed by Southern analysis or PCR for the transgene. Alternatively, the tissues or cells believed to express the transgene at the highest levels are tested for the presence and expression of the trarsgene using Southern analysis or PCR, although any tissues or cell types may be used for this analysis.

Alternative or additional methods for evaluating the presence of the transgene include, without limitation, suitable biochemical assays such as enzyme and/or immunological assays, histological stains for particular marker or enzyme activities, flow cytometric analysis, and the like. Analysis of the blood may also be useful to detect the presence of the transgene product in the blood, as well as to evaluate the effect of the transgene on the levels of various types of blood cells and other blood constituents.

Progeny of the transgenic animals may be obtained by mating the transgenic animal with a suitable partner, or by in vitro fertilization of eggs and/or sperm obtained from the transgenic animal. Where mating with a partner is to be performed, the partner may or may not be transgenic and/or a knockout; where it is transgenic, it may contain the same or a different transgene, or both. Alternatively, the partner may be a parental line. Where in vitro fertilization is used, the fertilized embryo may be implanted into a surrogate host or incubated in vitro, or both. Using either method, the progeny may be evaluated for the presence of the transgene using methods described above, or other appropriate methods.

The transgenic animals produced in accordance with the present invention will include exogenous genetic material. Further, in such embodiments the sequence will be attached to a transcriptional control element, e.g., a promoter, which preferably allows the expression of the transgene product in a specific type of cell.

Retroviral infection can also be used to introduce the transgene into a non-human animal. The developing non-human embryo can be cultured in vitro to the blastocyst stage. During this time, the blastomeres can be targets for retroviral infection (Jaenich, R. (1976) *PNAS* 73:1260–1264). Efficient infection of the blastomeres is obtained by enzymatic treatment to remove the zona pellucida (*Manipulating the Mouse Embryo*, Hogan eds. (Cold Spring Harbor Laboratory Press, Cold Spring Harbor, 1986). The viral vector system used to introduce the transgene is typically a replication-defective retrovirus carrying the transgene (Jahner et al. (1985) *PNAS* 82:6927–6931; Van der Putten et al. (1985) *PNAS* 82:6148–6152). Transfection is easily and efficiently obtained by culturing the blastomeres on a monolayer of virus-producing cells (Van der Putten, supra; Stewart et al. (1987) *EMBO J.* 6:383–388). Alternatively, infection can be performed at a later stage. Virus or virus-producing cells can be injected into the blastocoele (Jahner et al. (1982) *Nature* 298:623–628). Most of the founders will be mosaic for the transgene since incorporation occurs only in a subset of the cells which formed the transgenic non-human animal. Further, the founder may contain various retroviral insertions of the transgene at different positions in the genome which generally will segregate in the offspring. In addition, it is also possible to introduce transgenes into the germ line by intrauterine retroviral infection of the midgestation embryo (Jahner et al. (1982) supra).

A third type of target cell for transgene introduction is the embryonal stem cell (ES). ES cells are obtained from pre-implantation embryos cultured in vitro and fused with embryos (Evans et al. (1981) *Nature* 292:154–156; Bradley et al. (1984) *Nature* 309:255–258; Gossler et al. (1986) *PNAS* 83: 9065–9069; and Robertson et al. (1986) *Nature* 322:445–448). Transgenes can be efficiently introduced into the ES cells by DNA transfection or by retrovirus-mediated transduction. Such transformed ES cells can thereafter be combined with blastocysts from a non-human animal. The ES cells thereafter colonize the embryo and contribute to the germ line of the resulting chimeric animal. For review see Jaenisch, R. (1988) *Science* 240:1468–1474.

The present invention is further illustrated by the following examples which should not be construed as limiting in any way. The contents of all cited references (including literature references, issued patents, published patent applications as cited throughout this application) are hereby expressly incorporated by reference. The practice of the present invention will employ, unless otherwise indicated, conventional techniques that are within the skill of the art. Such techniques are explained fully in the literature. See, for example, Molecular Cloning A Laboratory Manual, (2nd ed., Sambrook, Fritsch and Maniatis, eds., Cold Spring Harbor Laboratory Press: 1989); DNA Cloning, Volumes I and II (D. N. Glover ed., 1985); Oligonucleotide Synthesis (M. J. Gait ed., 1984); U.S. Pat. No. 4,683,195; U.S. Pat. No. 4,683,202; and Nucleic Acid Hybridization (B. D. Hames & S. J. Higgins eds., 1984).

EXAMPLE 1

Detection of IL-1B (+3954)

The screening of the single base variation (C/T) polymorphism at IL-1B base +3954 was conducted by PCR amplification of genomic templates. One mismatch was inserted in a primer to complete a TaqI site as a positive control. The polymorphic TaqI site is native. The following primers were produced in an ABI DNA synthesizer based on the genomic sequences (Clark et al., 1986; GenBank X04500):

5' CTC AGG TGT CCT CGA AGA AAT CAA A 3' (SEQ ID No:9)

5' GCT TTT TTG CTG TGA GTC CCG 3' (SEQ ID No:10)

The PCR reaction conditions were as follows:

[95 C (2 minutes)] 1 cycle;

[95 C(1 minute), 67.5 C (1 minute), 74 C (1 minute)] 38 cycles; and

[72 C (8 minutes)] 1 cycle.

Restriction enzyme digestion was conducted at 60° C., for 8 hours. Sizing was by 8% PAGE. The digestion of the PCR product with Taq I yields a segment of 12 bp (the absence of which indicates incomplete digestion) and either two further segments of 85 and 97 bp (allele 1), or a single one of 182 bp (allele 2).

EXAMPLE 2

Detection of IL-1B (−511)

The single base polymorphism (C/T) at position—511 in the IL-1B gene was screened by PCR amplification of genomic templates, followed by RFLP (Restriction Fragment Length Polymorphism) analysis. The gene variation completes an Ava I restriction site in the most frequent allele, and a Bsu 36 I site in the rarer allele. Hence digestion of the PCR product with these enzymes provides efficient analysis of the IL-1B (−511) locus.

The following primers were produced in an ABI synthesizer based on the genomic sequence (Clark et al, 1986; GenBank X04500):

5' TGG CAT TGA TCT GGT TCA TC-3' (SEQ ID No:11)

5' GTT TAG GAA TCT TCC CAC TT-3' (SEQ ID No:12)

PCR conditions were as follows:

[95 C (1 minute)] 1 cycle

[95 C (1 minute)] 53 C (1 minute), 72 (1 minute)] 35 cycles

[72 C (5 minute)] 1 cycle.

Each PCR reaction was divided in two 25 μl aliquots; one was added to 3 units of Ava I, the other to 3.7 units of Bsu 36 I, in addition to 3 μl of the specific 10×restriction buffer. Digestion was at 37° C. overnight, sizing was by 9% PAGE. Ava I digestion produced 190+114 bp segments with allele 1, while allele 2 was uncut (304 bp). The Bsu 36 I digestion produced 190+114 bp fragments with allele 2, while allele 1 was uncut (304 bp). The restriction pattern obtained was inverted in the two aliquots (identifying homozygotes) or identical (identifying heterozygotes). This protocol provided efficient analysis of the IL-1B (−511) locus.

EXAMPLE 3

Detection of IL-1RN (VNTR)

The existence of a variable number of tandem repeats in intron 2 of IL-1RN gene was first reported during the cloning of the gene (Steinkasserer, A. et al., (1991) Nucleic Acids Res 19: 5095). This VNTR was characterised by Tarlow et al ((1993) *Hum Genet*. 91:403404) as a variable number (2 to 6) of 86 bp repeats. The following primers were produced in an ABI synthesizer based on the genomic sequence (Genbank X64532):

5'-CTC.AGC.AAC.ACT.CCT.AT-3' (+2879/+2895) (SEQ ID NO. 13)

5'-TCC.TGG.TCT.GCA.GCT.AA-3' (+3274/+3290) (SEQ ID NO. 14)

The PCR reaction conditions were as follows:

Cycling is performed at [96°, 1 min]×1 min; 60° C., 1 min; 70° C., 2 min;]×35; [70°, 5 min]×1; 4° C. Electrophoresis in 2% agarose, 90V, 30 min.

The PCR product sizes are direct indication of number of repeats: the most frequent allele (allele 1) yields a 412 bp product. As the flanking regions extend for 66 bp, the remaining 344 imply four 86 bp repeats. Similarly, a 240 bp product indicates 2 repeats (allele 2), 326 is for 3 repeats (allele 3), 498 is 5 (allele 4), 584 is 6 (allele 6). Frequencies in a North British Caucasian population for the four most frequent alleles are 0.734, 0.241, 0.021 and 0.004.

EXAMPLE 4

Detection of IL-1RN (+2018)

This single base variation (C/T at +2016) in Exon 2 was described by Clay et al. ((1996) Hum. Genet 97:723–726). These PCR primers (mismatched to the genomic sequence) was engineered to two enzyme cutting sites on the two alleles. These two alleles are 100% in linkage disequilibrium with the two most frequent alleles of IL-1RN (VNTR). The following primers were produced in an ABI synthesizer based on the genomic sequence (Genbank X04532):

5'-CTA TCT GAG GAA CAA ACT AGT AGC-3' (+1990/+2015) (SEQ ID NO. 15)

5'-TAG GAC ATT GCA CCT AGG GTT TGT -3' (+2133/+2156) (SEQ ID NO. 16)

Cycling is performed at [96°, 1 min]×1; [94°, 1 min; 57°, 1 min; 70°, 2 min;]×35; [70°, 5 min]×1; 4C. Each PCR reaction is divided in two µl of the specific 10× restriction buffer. Incubation is at 37° C. overnight. Electrophosis is by PAGE 9%.

The two enzymes cut respectively the two different alleles. Alu/will produce 126+28 bp fragments for allele 1, while it does not digest allele 2 (154 bp). Msp/will produce 125+29 bp with allele , while allele 1 is uncut (154 bp). Hence the two reaction s (separated side by side in PAGE) will give inverted pattens of digestion for homozygote individuals, and identical patterns in heterozygotes. Allelic frequencies in a North British Caucasian population are 0.74 and 0.26. For 90% power at 0.05 level of significance in a similar genetic pool, 251 cases should be studied to detect 1.5 fold increases in frequency, or 420 for 0.1 absolute increase in frequency.

EXAMPLE 5

Detection of IL-1A (−889)

The C/T single variation in the IL-1A promoter was described by McDowell et al. (Arthritis and Rheumatism 38: 221–228 (1995). One of the PCR primers has a base change to create an Nco I site when amplifying allele 1 (cytosine at −889). The following primers were produced in an ABI synthesizer based on the genomic sequence (Genbank X03833):

5'-AAG CTT GTT CTA CCA CCT GAA CTA GGC.-3' (−967/−945) (SEQ ID NO. 17)

5'-TTA CAT ATG AGC CTT CCA TG.-3' (−888/−869) (SEQ ID NO. 18)

MgCl$_2$ is used at 1 mM final, and PCR primers at 0.8 µM. Cycling is performed at [96°, 1 min]×1; 94°, 1 min; 50°, 1 min; 72°, 2 min;]×45; [72°, 5 min]×1' 4° C.

Each PCR reaction is added of 6 Units of Nco 1 in addition to µl of the specific 10×restriction buffer. Incubation is at 37° C. overnight. Electrophoresis is by PAGE 6%.

Nco 1 will produce 83+16 for allele 1, while it does not cut allele 2 (99 bp.). Heterozygotes will have the three bands. Allelic frequencies in North English White Caucasian population are 0.71 and 0.29. For 90% power at 0.05 level of significance in a similar genetic pool, 214 cases should be studied to detect 1.5 fold increase in frequency, or 446 for 0.1 absolute increase in frequency.

EXAMPLE 6

Association of IL-1B Allele 2 (+3954) and IL-1B Allele 2 (−511) with the Presence of Asthma in a Subject The following study was conducted to evaluate whether there was an association between asthma and alleles found in the relevant regions of the IL-1B gene. One hundred six (106) asthma patients were recruited for the study. 251 North British white Caucasian non-asthmatic subjects were recruited as controls. All asthma patients fulfilled the ATS criteria for the definition of asthma (Amer Rev Respir Dis 1985, 132:180–182.), and where relevant had a PC20 methacholine of less than 4 mg/ml. Asthma patients were clinically categorized as having either mild or severe asthma. Severe asthma was defined as those patients requiring more than 800 mg/day of inhaled steroids. Asthma patients on beta-2 agonist alone were categorized as having mild asthma. Of the total number of asthma patients, 50 were mild asthmatics on beta 2 agonist alone (FEV1 92.5±1.5% pred) and had a mean age of 26.5±0.9, and 56 were severe asthmatics on a regimen of at least 800 mg per day of inhaled steroids (FEV1 58.4±3.4% pred) with a mean age of 47.2±2.3. After informed consent was obtained, 10 mls of venous blood was drawn and collected in EDTA-containing tubes from each patient. Total genomic DNA was extracted and allele frequencies were assessed in DNA extracted from the 106 patients. For IL-1B (+3954) 105 patients could be genotyped. 104 patients were genotyped for IL-1B (−511). For each DNA, a single PCR product spanning the relevant regions of the IL-1B gene was produced and analyzed as described in Example 1. The data were analyzed using the Chi square test to compare carriage of the rare allele (genotypes carrying at least one copy of allele 2 between cohorts). The results for IL-1B (+3954) are presented in the following Table 1 and the results for IL-1B (−511) are presented in the following Table 2.

TABLE 1

| | IL-1B (+3954) | | |
|---|---|---|---|
| | 1.1 | 1.2 | 2.2 |
| Disease Severity | | | |
| MILD (N = 50) | 28 | 17 | 5 |
| SEVERE (N = 55) | 26 | 24 | 5 |
| CONTROLS (N = 251) | 165 | 81 | 5 |
| Mild vs Severe | Chi$^2$ = 0.497 | p = 0.48 | (N.S.) |
| "all" vs Control | Chi$^2$ = 6.402 | p = 0.01 | O.R. = 1.81 (95% C.I. = 1.14–2.88) |
| Severe vs Control | Chi$^2$ = 6.557 | p = 0.01 | O.R. = 2.14 (95% C.I. = 1.19–3.86) |

TABLE 2

| | IL-1B (−511) | | |
|---|---|---|---|
| | 1.1 | 1.2 | 2.2 |
| Disease Severity | | | |
| MILD (N = 50) | 2 | 19 | 3 |
| SEVERE (N = 54) | 19 | 31 | 4 |
| CONTROLS (N = 251) | 89 | 129 | 33 |
| Severe vs Mild | Chi² = 4.541 | p = 0.033 | O.R. = 2.34 (95% C.I. = 1.06–5.16) |
| "all" vs Control | Chi² = 2.948 | p = 0.086 | (NS) |

As evidenced by Tables 1 and 2, the presence of IL-1B allele 2 (+3954) and IL-1B allele 2 (−511) are significantly associated with clinical asthma Further, the presence of at least one copy of allele 2 at the IL-1B (−511) locus was found to be associated with more severe disease.

EXAMPLE 7

Association of IL-13 Allele 2 (+2581) with Asthma Severity

Summary

Carriage of the IL-13 (+2581) allele 2 is marginally associated with susceptibility to asthma (p=0.0615). It is significantly associated with severe asthma as defined by %FEV values (p=0.02). Among individuals with asthma, carriers of IL-13 (+2581) allele 2 were at an increased risk for severe asthma (OR=2.64, 95% C.I.=1.04–6.69).

Materials & Methods

DNA Analysis

For each individual enrolled in the study, a 7-ml sample of venous blood was collected in EDTA. DNA was extracted from uncoagulated blood by a modification of the salt-out technique (Nucleon™, Scotlab, UK) and stored at a final concentration of 200 µg/ml until used for genotyping. (Aliquots of plasma were also freshly separated and stored in 0.5 ml aliquots frozen at −200 C, but not used in this study). A consecutive code number was assigned to each sample. The control population was composed of 199 anonymous blood donors of the London blood bank. Biological and genetic studies were performed blindly by scientists who were unaware of clinical status.

Samples were genotyped for IL-13 (+2581) by RFLP by using the enzyme Nhe I. A control site was created by modifying the reverse primer. Primer sequences and genotyping conditions are below:

Forward primer: 5' CCA GAC ATG TGG TGG GAC AGG G 3' (SEQ ID No. 19)
Reverse primer: 5' CGA GGC CCC AGG ACC CCA GTG AGC TAG CAG 3' (SEQ ID No. 20)
PCR Cycles: [96° C., 5 min]×1; [96° C., 1 min; 60° C., 1 min; 72° C., 1 min]×35; [72° C., 5 min]×1.
Allele 1=250 bp PCR product (+27 bp)
Allele 2=152 bp+98 bp (+27 bp)
PCR conditions: Genomic DNA at 200 ng/25 µl reaction. MgCl₂ at 4 mM and primers at 1 mM final concentation.

Result

The results from the genotyping of DNA from 291 consecutive blood donors from the Trent Region of Northern England are presented in Table 3.

TABLE 3

| | IL-13 (+2581) Genotype | | |
|---|---|---|---|
| | 1.1 | 1.2 | 2.2 |
| Sheffield (normals) | 200 | 84 | 7 |

Allele frequencies:
allele 1.8316
allele 2.1684

As shown in the following Table 4, genotypes were comparable for 199 blood donors from London classified as normal.

TABLE 4

| | IL-13 (+2581) Genotype | | |
|---|---|---|---|
| | 1.1 | 1.2 | 2.2 |
| London (normals) | 141 | 57 | 1 |

Allele frequencies:
allele 1.8517
allele 2.1483

In both cohorts, allelic distributions were according to Hardy Weinberg equilibrium. 175 London asthma patients were also genotyped and the results are presented in Table 5.

TABLE 5

| | IL-13 (+2581) Genotype | | |
|---|---|---|---|
| | 1.1 | 1.2 | 2.2 |
| London (asthma) | 108 | 62 | 5 |

Allele frequencies:
allele 1.7943
allele 2.2057

Carriage of the rare allele was marginally different between asthma patients and London controls. London subjects with the 1.2 genotype were grouped with the 2.2 homozygotes from London, to make a group composed of individuals carrying allele 2. The London 1.1 homozygotes were compared with individuals carrying allele 2 as shown in the following Table 6. Chi Square analysis showed that the rare allele 2 was marginally associated with asthma (Chi-sq. p=0.0615).

TABLE 6

| Occurrence of individuals carrying allele 2 versus the 1.1 homozygotes among asthma patients and normals. | | | |
|---|---|---|---|
| | 1.2 and 2.2 | 1.1 | Totals |
| London (Normal) | 58 | 141 | 199 |
| London (Asthma) | 67 | 108 | 175 |
| Totals | 125 | 249 | 374 |

Summary Table for Chi Square Test

| | |
|---|---|
| Num. Missing | 0 |
| DF | 1 |
| Chi Square | 3.496 |
| Chi Square P-Value | .0615 |
| G-Squared | 3.494 |
| G-Squared P-Value | .0616 |
| Contingency Coef. | .096 |
| Phi | .097 |
| Cty. Cor. Chi Square | 3.097 |
| Cty. Cor. P-Value | .0784 |
| Fisher's Exact P-Value | • |

Whether the presence of the rare allele (allele 2) was associated with disease severity was then tested. Severity was judged on the basis of FEV measurements expressed as a percentage of the expected values for specific age and sex. First, it was determined whether the FEV values were significantly different on the basis of IL-13 genotype. Among the London asthma patients, those with the 1.2 genotype were grouped with the 2.2 homozygotes, to make a group composed of asthma patients carrying allele 2 (the 1.2 +2.2 group). The other group was composed of asthma patients homozygous for allele 1 (the 1.1 group). To determine whether the rare allele 2 was associated with asthma severity, a nonparametric Mann-Whitney analysis was performed assessing differences in %FEV values of group 1.2+2.2 versus the 1.1 group. A significant difference was found (p=0.0199) as shown in Table 7. The carriage of allele 2 was associated with lower %FEV values (more severe asthma). Only 159 London asthma patients could be tested, because not all of the patients had FEV measurements.

TABLE 7

Summary of % FEV Values by Genotype

| Genotype | Count | Sum Ranks | Mean Rank |
|---|---|---|---|
| 1.1 | 99 | 8575.000 | 86.616 |
| 1.2 + 2.2 | 60 | 4145.000 | 69.083 |

Mann-Whitney U for Column 1
Grouping Variable: Column 2

| | |
|---|---|
| U | 2315.000 |
| U Prime | 3625.000 |
| Z-Value | −2.327 |
| P-Value | .0199 |
| Tied Z-Value | −2.328 |
| Tied P-Value | .0199 |
| # Ties | 39 |

The relative risk of severe asthma was assessed with allele 2 by dividing the lowest quartile %FEV with the highest quartile %FEV. Chi Square analysis revealed significance with OR=2.63 (95%CI: 1.03–6.685).

EXAMPLE 8

IL-13 Gene Variants

The IL-13 gene is shown in FIG. 4. The gene comprises the following 4 exons: Exon I=2158–2345; Exon II=3403–3456; Exon III=3709–3813; and Exon IV=4160–5095. The coding sequence is from 2214–4267 (i.e. the mRNA is approx 2053 bp). All polymorphisms numbered from the putative transcription initiation site (2158 in FIG. 4).

Genomic DNA from several normal donors was PCR amplified and analysed by Conformation Sensitive Gel Electrophoresis (CSGE) to identify heteroduplexes and consequently putative polymorphisms. Gene variations were confirmed by sequencing of PCR products.

+571 C/A (intron 1)

Allele 1=C allele 2=A the presence of the A disrupts a site for the enzyme Sau 3AI (ÑGATC) when the reverse primer is modified (see below).

PCR conditions:

forward primer 5' CAA TGC AGC CAT TCT CCC CAG CAC ÑGAT 3' (1819)

reverse primer 5' GTT CAT CGT ACC TGC CTC TGG 3' (1772).

Annealing temperature: 58° C.

Mg concentration: 4 mls/25 mls reaction.

PCR product size: 187 bp.

Expected Result:

allele 1=163 bp+24 bp allele 2=187 bp.

+1979 C/T (intron 3)

Allele 1=C allele 2=T the presence of the T disrupts a site for the enzyme Pml I (CACÑGTG).

PCR Conditions:

forward primer 5' CAT CGA GAA GAC CCA GAG GAT G 3' (1672)

reverse primer 5' CCT CGA TTT TGG TGT CTC GGA C 3' (1673).

Annealing temperature: 56° C.

Mg concentration: 3 mls/25 mls reaction.

PCR product size: 444 bp.

Expected Result:

allele 1=381 bp+63 bp allele 2=444 bp.

+2100 G/A (Exon 4)

Allele 1=G allele 2=A the presence of the A disrupts a site for the enzyme Bsc BI (GGNÑNCC) when the reverse primer is modified (see below).

PCR Conditions:

forward primer 5' CTC TGG CGT TCT ACT CAC G 3' (1637)

reverse primer 5' CAA ATA ATG ATG CTT TCG AAG TTT CAG TGG AÑA 3' (1861).

Annealing temperature: 54° C.

Mg concentration: 4 mls/25 mls reaction.

PCR product size: 174 bp.

Expected Result:

allele 1=143 bp+31 bp allele 2=174 bp.

+2581 G/A (Exon 4)

Allele 1=G allele 2=A the presence of the A create a site for the enzyme Nhe I (G ÑCTAGC).

PCR Conditions:

forward primer 5' CCA GAC ATG TGG TGG GAC AGG G 3' (1741)

reverse primer 5' CGA GGC CCC AGG ACC CCA GTG AGÑC TAG CAG 3 ' (1742).

The reverse primer has been modified in order to create a control site for the enzyme Nhe I.

Annealing temperature: 60° C.
Mg concentration: 2 mls/25 mis reaction.
PCR product size: 277 bp.
Expected Result:
allele 1=250 bp (+27 bp)
allele 2=152 bp+98 bp (+27 bp).

What is claimed is:

1. A method for determining whether a subject has or is predisposed to developing an obstructive airway disease (OAD), comprising the step of detecting in a nucleic acid sample from the subject, an OAD associated allele, which is selected from the group consisting of: allele 2 of IL-13 (+2581); allele 2 of IL-1B (−511); allele 2 of IL-1B (+3954); or an allele in linkage disequilibrium with allele 2 of IL-1B (−511) or allele 2 of IL-1B (+3954) selected from the group consisting of: allele 4 of IL-1A (222/223); allele 4 of IL-1A (gz5/gz6); allele 1 of IL-1A (−889); allele 1 of (+3954); allele 3 of the gaat.p33330 marker; allele 3 of the Y31 marker; allele 2 of IL-1RN (+2018); allele 2 of IL-1RN (VNTR); allele 3 of IL-1A (222/223); allele 3 of IL-1A (gz5/gz6); allele 2 of IL-1A(−889); allele 1 of IL-1B (−511); allele 4 of the gaat.p33330 marker; allele 6 of the Y31 marker; allele 1 of IL-1RN (+2018); and allele 1 of IL-1RN (VNTR), wherein detection of the obstructive airway disease associated allele indicates that the subject has or is predisposed to the development of an obstructive airway disease.

2. A method of claim 1, wherein said detecting step is selected from the group consisting of: a) allele specific oligonucleotide hybridization; b) size analysis; c) sequencing; d) hybridization; e) 5' nuclease digestion; f) single-stranded conformation polymorphism; g) allele specific hybridization; h) primer specific extension; and j) oligonucleotide ligation assay.

3. A method of claim 1, wherein prior to or in conjunction with detection, the nucleic acid sample is subject to an amplification step.

4. A method of claim 2, wherein said size analysis is preceded by a restriction enzyme digestion.

5. A method of claim 1, which additionally comprises the detecting an IL-13 polymorphism.

6. A kit for determining the existence of or a susceptibility to developing an obstructive airway disease (OAD) in a subject, said kit comprising a first primer oligonucleotide that hybridizes 5' or 3' to an allele selected from the group consisting of: allele 2 of IL-13 (+2581); allele 2 of IL-1B (−511); allele 2 of IL-1B (+3954); or an allele in linkage disequilibrium with allele 2 of IL-1B (−511) or allele 2 of IL-1B (+3954) selected from the group consisting of: allele 4 of IL-1A (222/223); allele 4 of IL-1A (gz5/gz6); allele 1 of IL-1A (−889); allele 1 of (+3954); allele 3 of the gaat.p33330 marker; allele 3 of the Y31 marker; allele 2 of IL-1RN (+2018); allele 2 of IL-1RN (VNTR); allele 3 of XL-1A (222/223); allele 3 of IL-1A (gz5/gz6); allele 2 of IL-1A (−889); allele 1 of IL-1B (−511); allele 4 of the gaat.p33330 marker; allele 6 of the Y31 marker; allele 1 of IL-1RN (+2018); and allele 1 of IL-1RN (VNTR).

7. A kit of claim 6, which additionally comprises a second primer oligonucleotide that hybridizes either 3' or 5' respectively to the allele, so that the allele can be amplified.

8. A kit of claim 7, wherein said first primer and said second primer hybridize to a region in the range of between about 50 and about 1000 base pairs.

9. A kit of claim 8, wherein said primer is selected from the group consisting of any of SEQ ID Nos. 9, 10, 11, 12, 19 and 20.

10. A kit of claim 8, which additionally comprises a detection means.

11. A kit of claim 10, wherein the detection means is selected from the group consisting of: a) allele specific oligonucleotide hybridization; b) size analysis; c) sequencing; d)hybridization; e) 5' nuclease digestion; f) single-stranded conformation polymorphism; g) allele specific hybridization; h) primer specific extension; and j) oligonucleotide ligation assay.

12. A kit of claim 8, which additionally comprises an amplification means.

13. A kit of claim 8, which further comprises a control.

14. A method for selecting an appropriate therapeutic for an individual that has or is predisposed to developing an obstructive airway disease (OAD), comprising the steps of: detecting whether the subject contains an OAD causative allele or an OAD associated allele that is associated with an OAD causative allele; and selecting a therapeutic that compensates for the OAD causative allele.

15. A method of claim 14, wherein said detecting is performed using a technique selected from the group consisting of: a) allele specific oligonucleotide hybridization; b) size analysis; c) sequencing; d) hybridization; e) 5' nuclease digestion; f) single-stranded conformation polymorphism;

g) allele specific hybridization; h) primer specific extension; and j) oligonucleotide ligation assay.

16. A method of claim 14, wherein prior to or in conjunction with detecting, the nucleic acid sample is subjected to an amplification step.

17. A method of claim 14, wherein said amplification step employs a primer selected from the group consisting of SEQ ID Nos. 9, 10, 11, 12, 19 and 20.

18. A method of claim 14, wherein the OAD therapeutic is selected from the group consisting of: a steroid inhaler, cromolyn sodium, nedocromil, long acting beta-2 agonists, methylxanthines, leukotriene modifiers, quick relief beta-2 agonists, anticholinergics, systemic corticosteroids, an antibody directed against an intracellular adhesion molecule, an antibody against IgE, a thromboxane A2 synthetase inhibitor, a thromboxane prostanoid receptor antagonist, an eicosanoid modifier, a seratrodast, an ozagrel, a phosphodiesterase 4 isoenzyme inhibitor, a thromboxane A2 synthetase inhibitor, ditec, a platelet activating factor receptor antagonist, an antihistamine, an anti-thromboxane A2, an antibradykinin, an agent that inhibits activated eosinophils and T-cell recruitment, an IL-13 blocker, an IL-4 blocker, a ligand that binds and blocks the activity of IL-13 or IL-4, and a xanthine derivative.

19. A method of claim 14, wherein the OAD therapeutic is a modulator of an IL-1 activity.

20. A method of claim 19, wherein the IL-1 activity is IL-1α.

21. A method of claim 19, wherein the IL-1 activity is IL-1β.

22. A method of claim 19, wherein the IL-1 activity is IL-1RN.

23. A method of claim 19, wherein the modulator of an IL-1 activity is a protein, peptide, peptidomimetic, small molecule, nucleic acid or a nutraceutical.

24. A method of claim 19, wherein the modulator is an agonist.

25. A method of claim 19, wherein the modulator is an antagonist.

26. A method of claim 14, wherein the OAD causative allele or OAD associated allele is selected from the group consisting of: allele 2 of IL-13 (+2581); allele 2 of IL-1B (−511); allele 2 of IL-1B (+3954); or an allele in linkage disequilibrium with allele 2 of IL-1B (−51 1) or allele 2 of IL-1B (+3954) selected from the group consisting of: allele 4 of IL-1A (222/223); allele 4 of IL-1A (gz5/gz6); allele 1 of IL-1A (−889); allele 1 of (+3954); allele 3 of the gaat.p33330 marker; allele 3 of the Y31 marker; allele 2 of IL-1RN (+2018); allele 2 of IL-1RN (VNTR); allele 3 of IL-1A (222/223); allele 3 of IL1A (gz5/gz6); allele 2 of IL-1A (−889); allele 1 of IL-1B (−511); allele 4 of the gaat.p33330 marker; allele 6 of the Y31 marker; allele 1 of IL-1RN (+2018); and allele 1 of IL-1RN (VNTR).

27. A method of claim 14, wherein the OAD causative functional mutation is allele 2 of IL-1B (−511).

28. A method for treating or preventing the development of an OAD in a subject comprising the steps of detecting the presence of an OAD causative mutation or an OAD associated allele that is associated with an OAD causative mutation; and administering to the subject a therapeutic that compensates for the OAD causative mutation.

29. A method of claim 28, wherein the detecting step is selected from the group consisting of: a) allele specific oligonucleotide hybridization; b) size analysis; c) sequencing; d) hybridization; e) 5' nuclease digestion; f) single-stranded conformation polymorphism; g) allele specific hybridization; h) primer specific extension; and j) oligonucleotide ligation assay.

30. A method of claim 28, wherein prior to or in conjunction with detecting, the nucleic acid sample is subjected to an amplification step.

31. A method of claim 30, wherein said amplification step employs a primer selected from the group consisting of any of SEQ ID Nos. 9, 10, 11, 12, 19 and 20.

32. A method of claim 29, wherein said size analysis is preceded by a restriction enzyme digestion.

33. A method of claim 32, wherein said restriction enzyme digestion uses a restriction enzyme selected from the group consisting of Alu I, Msp I, Nco I, Fnu 4HI, Ava I, Bsu 36 I, and Taq I.

34. A method of claim 28, wherein the therapeutic is selected from the group consisting of: a steroid inhaler, cromolyn sodium, nedocromil, long acting beta-2 agonists, methylxanthines, leukotriene modifiers, quick relief beta-2 agonists, anticholinergics, systemic corticosteroids, an antibody directed against an intracellular adhesion molecule, an antibody against IgE, a thromboxane A2 synthetase inhibitor, a thromboxane prostanoid receptor antagonist, an eicosanoid modifier, a seratrodast, an ozagrel, a phosphodiesterase 4 isoenzyme inhibitor, a thromboxane A2 synthetase inhibitor, ditec, a platelet activating factor receptor antagonist, an antihistamine, an anti-thromboxane A2, an antibradykinin, an agent that inhibits activated eosinophils and T-cell recruitment, an IL-13 blocker, an IL-4 blocker, a ligand that binds and blocks the activity of IL-13 or IL-4, and a xanthine derivative.

35. A method of claim 28, wherein the therapeutic is selected from the group consisting of: a modulator of an IL-1 activity.

36. A method of claim 35, wherein the IL-1 activity is IL-1α.

37. A method of claim 36, wherein the IL-1 activity is IL-1β.

38. A method of claim 36, wherein the IL-1 activity is IL-1Ra.

39. A method of claim 35, wherein the therapeutic is a protein, peptide, peptidomimetic, small molecule or a nucleic acid.

40. A method of claim 35, wherein the modulator is an agonist.

41. A method of claim 36, wherein the modulator is an antagonist.

42. A method of claim 28, wherein the OAD causative mutation or OAD associated allele is an allele of a polymorphic marker selected from the group consisting of: allele 2 of IL-13 (+2581); allele 2 of IL-1B (−511); allele 2 of IL-1B (+3954); or an allele in linkage disequilibrium with allele 2 of IL-1B (−511) or allele 2 of IL-1B (+3954) selected from the group consisting of: allele 4 of IL-1A (222/223); allele 4 of IL-1A (gz5/gz6); allele 1 of IL-1A (−889); allele 1 of (+3954); allele 3 of the gaat.p33330 marker; allele 3 of the Y31 marker; allele 2 of IL-1RN (+2018); allele 2 of IL-1RN (VNTR); allele 3 of IL-1A (222/223); allele 3 of IL-1A (gz5/gz6); allele 2 of IL-1A (−889); allele 1 of IL-1B (−511); allele 4 of the gaat.p33330 marker; allele 6 of the Y31 marker, allele 1 of IL-1RN (+2018); and allele 1 of IL-1RN (VNTR).

43. A method of claim 28, wherein the ILD causative functional mutation is IL-1B (−511) allele 2.

44. The method of claim 1, wherein the obstructive airway disease is asthma.

45. The method of claim 1 or 44, wherein the obstructive airway disease associated allele is allele 2 of IL-1B (−511) or IL-1B (+3954).

46. The kit of claim 6, wherein the obstructive airway disease is asthma.

47. The kit of claim 6 or 46, wherein the obstructive airway disease associated allele is allele 2 of IL-1B (−511) or IL-1B (+3954).

48. The method of claim 28 or 42, wherein the obstructive airway disease is asthma.

49. The method of claim 28 or 42, wherein the obstructive airway disease associated allele is allele 2 of IL-1B (−511) or IL-1B (+3954).

* * * * *

SEQUENCE LISTING

<160> NUMBER OF SEQ ID NOS: 28

<210> SEQ ID NO 1
<211> LENGTH: 11970
<212> TYPE: DNA
<213> ORGANISM: Homo sapiens

<400> SEQUENCE: 1

```
aagcttctac cctagtctgg tgctacactt acattgctta catccaagtg tggttatttc      60
tgtggctcct gttataacta ttatagcacc aggtctatga ccaggagaat tagactggca     120
ttaaatcaga ataagagatt ttgcacctgc aatagacctt atgacaccta accaacccca     180
ttatttacaa ttaaacagga acagagggaa tactttatcc aactcacaca agctgttttc     240
ctcccagatc catgcttttt tgcgtttatt attttttaga gatgggggct tcactatgtt     300
gcccacactg gactaaaact ctgggcctca agtgattgtc ctgcctcagc ctcctgaata     360
gctgggacta caggggcatg ccatcacacc tagttcattt cctctattta aaatatacat     420
ggcttaaact ccaactggga acccaaaaca ttcatttgct aagagtctgg tgttctacca     480
cctgaactag gctggccaca ggaattataa agctgagaa attctttaat aatagtaacc     540
aggcaacatc attgaaggct catatgtaaa aatccatgcc ttcctttctc ccaatctcca     600
ttcccaaact tagccactgg ttctggctga ggccttacgc atacctcccg gggcttgcac     660
acaccttctt ctacagaaga cacaccttgg gcatatccta cagaagacca ggcttctctc     720
tggtccttgg tagagggcta ctttactgta acagggccag ggtggagagt tctctcctga     780
agctccatcc cctctatagg aaatgtgttg acaatattca gaagagtaag aggatcaaga     840
cttctttgtg ctcaaatacc actgttctct tctctacccct gccctaacca ggagcttgtc     900
accccaaact ctgaggtgat ttatgcctta atcaagcaaa cttccctctt cagaaaagat     960
ggctcatttt ccctcaaaag ttgccaggag ctgccaagta ttctgccaat tcaccctgga    1020
gcacaatcaa caaattcagc cagaacacaa ctacagctac tattagaact attattatta    1080
ataaattcct ctccaaatct agcccctgga cttcggattt cacgatttct cccttcctcc    1140
tagaaacttg ataagtttcc cgcgcttccc tttttctaag actacatgtt tgtcatctta    1200
taaagcaaag gggtgaataa atgaaccaaa tcaataactt ctggaatatc tgcaaacaac    1260
aataatatca gctatgccat ctttcactat tttagccagt atcgagttga atgaacatag    1320
aaaaatacaa aactgaattc ttccctgtaa attccccgtt ttgacgacgc acttgtagcc    1380
acgtagccac gcctacttaa gacaattaca aaaggcgaag aagactgact caggcttaag    1440
ctgccagcca gagagggagt catttcattg gcgtttgagt cagcaaaggt attgtcctca    1500
catctctggc tattaaagta ttttctgttg ttgttttttct ctttggctgt tttctctcac    1560
attgccttct ctaaagctac agtctctcct ttcttttctt gtccctccct ggtttggtat    1620
```

```
gtgacctaga attacagtca gatttcagaa aatgattctc tcattttgct gataaggact    1680
gattcgtttt actgagggac ggcagaacta gtttcctatg agggcatggg tgaatacaac    1740
tgaggcttct catgggaggg aatctctact atccaaaatt attaggagaa aattgaaaat    1800
ttccaactct gtctctctct tacctctgtg taaggcaaat accttattct tgtggtgttt    1860
ttgtaacctc ttcaaacttt cattgattga atgcctgttc tggcaataca ttaggttggg    1920
cacataagga ataccaacat aaataaaaca ttctaaaaga gtttacgat ctaataaagg     1980
agacaggtac atagcaaact aattcaaagg agctagaaga tggagaaaat gctgaatgtg    2040
gactaagtca ttcaacaaag ttttcaggaa gcacaaagag gagggctcc cctcacagat     2100
atctggatta gaggctggct gagctgatgg tggctggtgt tctctgttgc agaagtcaag    2160
atggccaaag ttccagacat gtttgaagac ctgaagaact gttacaggta aggaataaga    2220
tttatctctt gtgatttaat gagggtttca aggctcacca gaatccagct aggcataaca    2280
gtggccagca tgggggcagg ccggcagagg ttgtagagat gtgtactagt cctgaagtca    2340
gagcaggttc agagaagacc cagaaaaact aagcattcag catgttaaac tgagattaca    2400
ttggcaggga gaccgccatt ttagaaaaat tattttgag gtctgctgag ccctacatga     2460
atatcagcat caacttagac acagcctctg ttgagatcac atgccctgat ataagaatgg    2520
gtttttactgg tccattctca ggaaaacttg atctcattca ggaacaggaa atggctccac   2580
agcaagctgg gcatgtgaac tcacatatgc aggcaaatct cactcagatg tagaagaaag    2640
gtaaatgaac acaagataa aattacgaa catattaaac taacatgatg tttccattat      2700
ctgtagtaaa tactaacaca aactaggctg tcaaaatttt gcctggatat tttactaagt    2760
ataaattatg aaatctgttt tagtgaatac atgaaagtaa tgtgtaacat ataatctatt    2820
tggttaaaat aaaaggaag tgcttcaaaa cctttctttt ctctaaagga gcttaacatt     2880
cttccctgaa cttcaattaa agctcttcaa tttgttagcc aagtccaatt tttacagata    2940
aagcacaggt aaagctcaaa gcctgtcttg atgactacta attccagatt agtaagatat    3000
gaattactct acctatgtgt atgtgtagaa gtccttaaat ttcaaagatg acagtaatgg    3060
ccatgtgtat gtgtgtgacc cacaactatc atggtcatta agtacattg gccagagacc     3120
acatgaaata acaacaatta cattctcatc atcttattt gacagtgaaa atgaagaaga    3180
cagttcctcc attgatcatc tgtctctgaa tcaggtaagc aaatgactgt aattctcatg    3240
ggactgctat tcttacacag tggtttcttc atccaaagag aacagcaatg acttgaatct    3300
taaatacttt tgttttaccc tcactagaga tccagagacc tgtctttcat tataagtgag    3360
accagctgcc tctctaaact aatagttgat gtgcattggc ttctcccaga acagagcaga    3420
actatcccaa atccctgaga actggagtct cctggggcag gcttcatcag gatgttagtt    3480
atgccatcct gagaaagccc cgcaggccgc ttcaccaggt gtctgtctcc taacgtgatg    3540
tgttgtggtt gtcttctctg acaccagcat cagaggttag agaaagtctc caaacatgaa    3600
gctgagagag aggaagcaag ccagctgaaa gtgagaagtc tacagccact catcaatctg    3660
tgttattgtg tttggagacc acaaatagac actataagta ctgcctagta tgtcttcagt    3720
actggcttta aaagctgtcc ccaaaggagt atttctaaaa tattttgagc attgttaagc    3780
agatttttaa cctcctgaga gggaactaat tggaaagcta ccactcacta caatcattgt    3840
taacctattt agttacaaca tctcattttt gagcatgcaa ataatgaaa aagtcttcct     3900
aaaaaaatca tcttttatc ctggaaggag gaaggaaggt gagacaaaag ggagagaggg     3960
agggaagcct aatgaaacac cagttaccta agaccagaat ggagatcctc ctcactacct    4020
```

```
ctgttgaata cagcacctac tgaaagaact ttcattccct gaccatgaac agcctctcag    4080
cttctgtttt ccttcctcac agaaatcctt ctatcatgta agctatggcc cactccatga    4140
aggctgcatg gatcaatctg tgtctctgag tatctctgaa acctctaaaa catccaagct    4200
taccttcaag gagagcatgg tggtagtagc aaccaacggg aaggttctga agaagagacg    4260
gttgagttta agccaatcca tcactgatga tgacctggag gccatcgcca atgactcaga    4320
ggaaggtaag gggtcaagca caataatatc tttcttttac agttttaagc aagtagggac    4380
agtagaattt aggggaaaat taaacgtgga gtcagaataa caagaagaca accaagcatt    4440
agtctggtaa ctatacagag gaaaattaat ttttatcctt ctccaggagg gagaaatgag    4500
cagtggcctg aatcgagaat acttgctcac agccattatt tcttagccat attgtaaagg    4560
tcgtgtgact tttagccttt caggagaaag cagtaataag accacttacg agctatgttc    4620
ctctcatact aactatgcct ccttggtcat gttacataat cttttcgtga ttcagtttcc    4680
tctactgtaa aatggagata atcagaatcc cccactcatt ggattgttgt aaagattaag    4740
agtctcaggc tttacagact gagctagctg ggccctcctg actgttataa agattaaatg    4800
agtcaacatc ccctaacttc tggactagaa taatgtctgg tacaaagtaa gcacccaata    4860
aatgttagct attactatca ttattattat tattttattt ttttttttg agatggagtc    4920 tggctctgtc acccaggctg gagtgcagtg gcacaatctc ggctcactgc aagctctgcc    4980
tcctgggttc atgccattct cctgcctcag cctcccgagt aagctgggaa tacaggcacc    5040
cgccactgtt cccggctaat ttttgtatt tttagtagag acggagtttc accgtggtct    5100
ccatctcctc gtgatccacc caccttggcc tcccaaagtg ccgggattac aggcgtgagc    5160
caccgcgccc ggcctattat tattattatt actactacta ctacctatat gaatactacc    5220
agcaatacta atttattaat gactggatta tgtctaaacc tcacaagaat cctaccttct    5280
cattttacat aaaaggaaac taagctcatt gagataggta aactgcccaa tggcatacat    5340
ctgtaagtgg gagagcctca aatctaattc agttctacct gagtaaaaaa atcatggttt    5400
ctcctccatc cctttactgt acaagcctcc acatgaacta taaacccaat attcctgttt    5460
ttaagataat acctaagcaa taacgcatgt tcacctagaa ggttttaaaa tgtaacaaaa    5520
tataagaaaa taaaaatcac tcatatcgtc agtgagagtt tactactgcc agcactatgg    5580
tatgtttcct taaaatcttt gctatacaca tacctacatg tgaacaaata tgtctaacat    5640
caagaccaca ctatttacaa ctttatatcc agcttttctt acttagcaat gtattgagga    5700
cattttagag tgcccgtttt tcaccattat aagcaatgca acaatgaaca tctgtataaa    5760
taaatattca tttctctcac cctttatttc cttagaatat attcctagaa gtagaatttc    5820
ccagagccat gaggatttgt gacgctattg atatgtgcca ctttgcactc tctgtgacat    5880
atataattat ttttaatgca ttcatttttt tctcagagtc cattcgtttg aaaacataga    5940
cgggaaatac tggtagtctt ccttgtcagt tagaaacacc caaacaatga aaatgaaaa    6000 agttgcacaa atagtctcta aaacaatga aactattgcc tgaggaattg aagtttaaaa    6060
agaagcacat aagcaacaac aaggataatc ctagaaaacc agttctgctg actgggtgat    6120
ttcacttctc tttgcttcct catctggatt ggaatattcc taatacccccc tccagaacta    6180 ttttcccctgt ttgtactaga ctgtgtatat catctgtgtt tgtacataga cattaatctg    6240
cacttgtgat catggtttta gaatcatcag agcctaggtc atcaccttt agcttcctga    6300 gcaatgtgaa atacaacttt atgaggatca tcaaatacga attcatcctg aatgacgccc    6360
```

-continued

```
tcaatcaaag tataattcga gccaatgatc agtacctcac ggctgctgca ttacataatc    6420
tggatgaagc aggtacatta aaatggcacc agacatttct gtcatcctcc cctcctttca    6480
tttacttatt tatttatttc aatctttctg cttgcaaaaa acatacctct tcagagttct    6540
gggttgcaca attcttccag aatagcttga agcacagcac ccccataaaa atcccaagcc    6600
agggcagaag gttcaactaa atctggaagt tccacaagag agaagtttcc tatctttgag    6660
agtaaagggt tgtgcacaaa gctagctgat gtactacctc tttggttctt tcagacattc    6720
ttaccctcaa ttttaaaact gaggaaactg tcagacatat aaatgatttt actcagatttt    6780
acccagaagc caatgaagaa caatcactct cctttaaaaa gtctgttgat caaactcaca    6840
agtaacacca aaccaggaag atctttatta tctctgataa catatttgtg aggcaaaacc    6900
tccaataagc tacaaatatg gcttaaagga tgaagtttag tgtccaaaaa cttttatcac    6960
acacatccaa ttttcatggc ggacatgttt tagtttcaac agtatacata ttttcaaagg    7020
tccagagagg caattttgca ataaacaagc aagactttt ctgattggat gcacttcagc    7080
taacatgctt tcaactctac atttacaaat tattttgtgt tctatttttc tacttaatat    7140
tatttctgca attttcccaa tattgacatc gtgtatgtat ttgccatttt taatatcact    7200
agacaattca atcaggttgc tacgttggtc ccttgggttt actctaaata gcttgattgc    7260
aaatatcttt gtatatatta ttgttttttc tcctatcttg taatttcttt gagcacatcc    7320
caaagaggaa tgcctagatc aatgggcaca ataatttga cagctcttat taaacattat    7380
tctgtaagta aaaactgaac tacttttcag tatcactagc aacatatgag tgtatcagct    7440
tcctaaaccc ctccatgtta ggtcattatg aacttatgat ctaacaaatt acagggtctt    7500
atcccactaa tgaaattata agagattcaa cacttattca gccccgaagg attcattcaa    7560
cgtagaaaat tctaagaaca ttaaccaagt atttacctgc ctagtgagtg tggaagacat    7620
tgtgaaggac acaaagatgt atagaattcc attcctgact tccaggtatt tacaccatag    7680
gtggggacct aactacacac acacacacac acacacacac acacacacac accatgcaca    7740
cacaatctac atcaacactt gattttatac aaatacaatg aatttacttt cttttttggtt    7800
cttctcttca ccagtgaaat ttgacatggg tgcttataag tcatcaaagg atgatgctaa    7860
aattaccgtg attctaagaa tctcaaaaac tcaattgtat gtgactgccc aagatgaaga    7920
ccaaccagtg ctgctgaagg tcagttgtcc tttgtctcca acttaccttc atttacatct    7980
catatgtttg taaataagcc caataggcag acacctctaa caaggtgaca ctgtcctctt    8040
tccttcctac cacagccccc acctacccac cccactccca ttgattccag aggcgtgcct    8100
aggcaggatc tatgagaaaa tataacgag agtaagagga aaattaccttt cttctttttt    8160
cctttccctg cctgacctta ttcacctccc atcccagagc atccatttat tccattgatc    8220
tttactgaca tctattatct gacctacaca atactagaca ttaggacaat gtggcctgcc    8280
tccaagaaac tcaaataagc caactgagat cagagaggat taatcacctg ccaatgggca    8340
caaagcaaca agctgggagc caagtcccaa aatgggccct gctgcttcca gttcccctct    8400
ctctgcattg atgtcagcat tatccttcgt cccagtcctg tctccactac cactttcccc    8460
ctcaaacaca cacacacaca acagcctttag atgttttctc cactgataag taggtgactc    8520
aatttgtaag tatataatcc aagaccttct attcccaagt agaatttatg tgcctgcctg    8580
tgcttttcta cctggatcaa gtgatgtcta cagagtaggg cagtagcttc attcatgaac    8640
tcattcaaca agcattattc actgagagcc ttgtattttt caggcatagt gccaacagca    8700
gtgtggacag tggtgcatca aagcctctag tctcatagaa cttagtcttc tggaggatat    8760
```

```
ggaaaacaga caacccaaac aaccaacaaa agagcaagat gctgcaaaaa aaaaaaaaat   8820 gaataggggtg ctaagataga gaaaagtggg agagtgctat ttagacaaag tggtaaaaac   8880
aaagcccctt gtgagatgag agctgccgac agaggggggcg ggtcatggtt gtgggttttt   8940
gggtaggaca ttcagaggag ggggcgggtc gtggttgtgg gttttttgggt aggacattca   9000 gaggagggggg cgggtcgtgg ttgtgggttt ttgggtagga cattcagagg aggggcggg   9060 tcgtggttgt gggttttttgg gtaggacatt cagaggaggg ggcgggtcgt ggttgtgggt   9120
ttttgggaca ttcagaggag tctgaatgca cccaggccta caacttcaag atggtaaagg   9180
acagctccaa ggatcagaag aagcattctt ggaactgggg cattttgaga aggaggaaaa   9240
atatgcagag actagtgctt gcagagcttg catttggatt tcatttgagg tacaatgaaa   9300
acccattaat gggtttcaca cagtgcaatg gcctgacctc acttatattt cctaaaatag   9360
aaaacagatc agaaggaagg caatagagaa gcagaaagtc caatgaggag gtttcacagc   9420
agtcatgggg gtggggtaag gaaaagaagt ggaaagaaac agacagaatt gggttatatt   9480
ttggagatag aaccaacaga aggaagagga gaaacaacat ttactgagaa gggaaaaagt   9540
aggagaggaa taggtttggg aaataaatcc tgctgacatt ggaaacccca aggaagcctc   9600
aaaagtatat ttacttgctt tagatttaaa agaataggaa agaagcatct caacttggaa   9660
tttgaaatct attttttccat aaaagtattg ttaaattcta ctcatactca caagaaaagt   9720
acattctaaa gagtatattg aaagagttta ctgatatact taggaatttt gtgtgtatgt   9780
gtgtgtgtgt atgtgtgtgt gtgtgtttaa ccttcaattg ttgacttaaa tactgagata   9840
aatgtcatct aaatgctaaa ttgatttccc aaaggtatga tttgttcact tggagatcaa   9900
aatgtttagg gggcttagaa tcactgtagt gctcagattt gatgcaaaat gtcttaggcc   9960
tatgttgaag gcaggacaga aacaatgttt ccctcctacc tgcctggata cagtaagata  10020
ctagtgtcac tgacaatctt cataactaat ttagatctct ctccaatcaa ctaaggaaat  10080
caactcttat taatagactg ggccacacat ctactaggca tgtaataaat gcttgctgaa  10140
tgaacaaatg aatgaagagc ctatagcatc atgttacagc catagtccta aagtggtgtt  10200
tctcatgaag gccaaatgct aagggattga gcttcagtcc ttttttctaac atcttgttct  10260 ctaacagaat tctcttcttt tcttcatagg agatgcctga gatacccaaa accatcacag  10320
gtagtgagac caacctcctc ttcttctggg aaactcacgg cactaagaac tatttcacat  10380
cagttgccca tccaaacttg tttattgcca caaagcaaga ctactgggtg tgcttggcag  10440
gggggccacc ctctatcact gactttcaga tactggaaaa ccaggcgtag gtctggagtc  10500
tcacttgtct cacttgtgca gtgttgacag ttcatatgta ccatgtacat gaagaagcta  10560
aatcctttac tgttagtcat ttgctgagca tgtactgagc cttgtaattc taaatgaatg  10620
tttacactct ttgtaagagt ggaaccaaca ctaacatata atgttgttat ttaaagaaca  10680
ccctatattt tgcatagtac caatcatttt aattattatt cttcataaca attttaggag  10740
gaccagagct actgactatg gctaccaaaa agactctacc catattacag atgggcaaat  10800
taaggcataa gaaaactaag aaatatgcac aatagcagtt gaaacaagaa gccacagacc  10860
taggatttca tgatttcatt tcaactgttt gccttctgct tttaagttgc tgatgaactc  10920
ttaatcaaat agcataagtt tctgggacct cagtttttatc attttcaaaa tggagggaat  10980
aatacctaag ccttcctgcc gcaacagttt tttatgctaa tcagggaggt cattttggta  11040
aaatacttct cgaagccgag cctcaagatg aaggcaaagc acgaaatgtt attttttaat  11100
```

-continued

| | | | | |
|---|---|---|---|---|
| tattatttat | atatgtattt | ataaatatat | ttaagataat | tataatatac tatatttatg 11160 |
| ggaacccctt | catcctctga | gtgtgaccag | gcatcctcca | caatagcaga cagtgttttc 11220 |
| tgggataagt | aagtttgatt | tcattaatac | agggcatttt | ggtccaagtt gtgcttatcc 11280 |
| catagccagg | aaactctgca | ttctagtact | tgggagacct | gtaatcatat aataaatgta 11340 |
| cattaattac | cttgagccag | taattggtcc | gatctttgac | tcttttgcca ttaaacttac 11400 |
| ctgggcattc | ttgtttcatt | caattccacc | tgcaatcaag | tcctacaagc taaaattaga 11460 |
| tgaactcaac | tttgacaacc | atgagaccac | tgttatcaaa | actttctttt ctggaatgta 11520 |
| atcaatgttt | cttctaggtt | ctaaaaattg | tgatcagacc | ataatgttac attattatca 11580 |
| acaatagtga | ttgatagagt | gttatcagtc | ataactaaat | aaagcttgca acaaaattct 11640 |
| ctgacacata | gttattcatt | gccttaatca | ttattttact | gcatggtaat tagggacaaa 11700 |
| tggtaaatgt | ttacataaat | aattgtattt | agtgttactt | tataaaatca aaccaagatt 11760 |
| ttatattttt | ttctcctctt | tgttagctgc | cagtatgcat | aaatggcatt aagaatgata 11820 |
| atatttccgg | gttcacttaa | agctcatatt | acacatacac | aaaacatgtg ttcccatctt 11880 |
| tatacaaact | cacacataca | gagctacatt | aaaaacaact | aataggccag gcacggtggc 11940 |
| tcagacctgt | aatcccagca | ctttgggagg | | 11970 |

<210> SEQ ID NO 2
<211> LENGTH: 9721
<212> TYPE: DNA
<213> ORGANISM: Homo sapiens
<220> FEATURE:
<221> NAME/KEY: modified_base
<222> LOCATION: (1)..(9721)
<223> OTHER INFORMATION: "n" represents a, t, c or g

<400> SEQUENCE: 2

| | | | | |
|---|---|---|---|---|
| agaaagaaag | agagagagaa | agaaaagaaa | gaggaaggaa | ggaaggaagg aagaaagaca 60 |
| ggctctgagg | aaggtggcag | ttcctacaac | gggagaacca | gtggttaatt tgcaaagtgg 120 |
| atcctgtgga | ggcanncaga | gggagtcccct | aggccaccca | gacagggctt ttagctatct 180 |
| gcaggccaga | caccaaattt | caggagggct | cagtgttagg | aatggattat ggcttatcaa 240 |
| attcacagga | aactaacatg | ttgaacagct | tttagatttc | ctgtggaaaa tataacttac 300 |
| taaagatgga | gttcttgtga | ctgactcctg | atatcaagat | actgggagcc aaattaaaaa 360 |
| tcagaaggct | gcttggagag | caagtccatg | aaatgctctt | tttcccacag tagaacctat 420 |
| ttccctcgtg | tctcaaatac | ttgcacagag | gctcactccc | ttggataatg cagagcgagc 480 |
| acgatacctg | gcacatacta | atttgaataa | aatgctgtca | aattcccatt cacccattca 540 |
| agcagcaaac | tctatctcac | ctgaatgtac | atgccaggca | ctgtgctaga cttggctcaa 600 |
| aaagatttca | gtttcctgga | ggaaccagga | gggcaaggtt | tcaactcagt gctataagaa 660 |
| gtgttacagg | ctggacacgg | tggctcacgc | ctgtaatccc | aacatttggg aggccgaggc 720 |
| gggcagatca | caaggtcagg | agatcgagac | catcctggct | aacatggtga aaccctgtct 780 |
| ctactaaaaa | tacaaaaaat | tagccgggcg | ttggcggcag | gtgcctgtag tcccagctgc 840 |
| tggggaggct | gaggcaggag | aatggtgtga | acccgggagg | cggaacttgc aggggggcga 900 |
| gatcgtgcca | ctgcactcca | gcctgggcga | cagagtgaga | ctctgtctca aaaaaaaaa 960 |
| aaaagtgtta | tgatgcagac | ctgtcaaaga | ggcaaaggag | ggtgttccta cactccaggc 1020 |
| actgttcata | acctggactc | tcattcattc | tacaaatgga | gggctcccct gggcagatcc 1080 |
| ctggagcagg | cactttgctg | gtgtctcggt | taaagagaaa | ctgataactc ttggtattac 1140 |

```
caagagatag agtctcagat ggatattctt acagaaacaa tattcccact tttcagagtt   1200
caccaaaaaa tcattttagg cagagctcat ctggcattga tctggttcat ccatgagatt   1260
ggctagggta acagcacctg gtcttgcagg gttgtgtgag cttatctcca gggttgcccc   1320
aactccgtca ggagcctgaa ccctgcatac cgtatgttct ctgccccagc caagaaaggt   1380
caattttctc ctcagaggct cctgcaattg acagagagct cccgaggcag agaacagcac   1440
ccaaggtaga gacccacacc ctcaatacag acagggaggg ctattggccc ttcattgtac   1500
ccatttatcc atctgtaagt gggaagattc ctaaacttaa gtacaaagaa gtgaatgaag   1560
aaaagtatgt gcatgtataa atctgtgtgt cttccacttt gtcccacata tactaaattt   1620
aaacattctt ctaacgtggg aaaatccagt attttaatgt ggacatcaac tgcacaacga   1680
ttgtcaggaa acaatgcat atttgcatgg tgatacattt gcaaatgtg tcatagtttg   1740 ctactccttg cccttccatg aaccagagaa ttatctcagt ttattagtcc cctcccctaa   1800
gaagcttcca ccaatactct tttcccctttt cctttaactt gattgtgaaa tcaggtattc   1860
aacagagaaa tttctcagcc tcctacttct gcttttgaaa gctataaaaa cagcgaggga   1920
gaaactggca gataccaaac ctcttcgagg cacaaggcac aacaggctgc tctgggattc   1980
tcttcagcca atcttcattg ctcaagtatg actttaatct tccttacaac taggtgctaa   2040
gggagtctct ctgtctctct gcctctttgt gtgtatgcat attctctctc tctctctctt   2100
tctttctctg tctctcctct ccttcctctc tgcctcctct ctcagctttt tgcaaaaatg   2160
ccaggtgtaa tataatgctt atgactcggg aaatattctg ggaatggata ctgcttatct   2220
aacagctgac accctaaagg ttagtgtcaa agcctctgct ccagctctcc tagccaatac   2280
attgctagtt gggggtttggt ttagcaaatg cttttctcta gacccaaagg acttctcttt   2340
cacacattca ttcatttact cagagatcat ttctttgcat gactgccatg cactggatgc   2400
tgagagaaat cacacatgaa cgtagccgtc atggggaagt cactcatttt ctcctttta   2460 cacaggtgtc tgaagcagcc atggcagaag tacctgagct cgccagtgaa atgatggctt   2520
attacaggtc agtggagacg ctgagaccag taacatgagc aggtctcctc tttcaagagt   2580
agagtgttat ctgtgcttgg agaccagatt ttttcccctaa attgcctctt tcagtggcaa   2640
acagggtgcc aagtaaatct gatttaaaga ctactttccc attacaagtc cctccagcct   2700
tgggacctgg aggctatcca gatgtgttgt tgcaagggct tcctgcagag gcaaatgggg   2760
agaaaagatt ccaagcccac aatacaagga atccctttgc aaagtgtggc ttggagggag   2820
agggagagct cagatttag ctgactctgc tgggctagag gttaggcctc aagatccaac   2880
agggagcacc agggtgccca cctgccaggc ctagaatctg ccttctggac tgttctgcgc   2940
atatcactgt gaaacttgcc aggtgtttca ggcagctttg agaggcaggc tgtttgcagt   3000
ttcttatgaa cagtcaagtc ttgtacacag ggaaggaaaa ataaacctgt ttagaagaca   3060
taattgagac atgtccctgt ttttattaca gtggcaatga ggatgacttg ttctttgaag   3120
ctgatggccc taaacagatg aaggtaagac tatgggttta actcccaacc caaggaaggg   3180
ctctaacaca gggaaagctc aaagaaggga gttctgggcc actttgatgc catggtattt   3240
tgttttagaa agactttaac ctcttccagt gagacacagg ctgcaccact tgctgacctg   3300
gccacttggt catcatatca ccacagtcac tcactaacgt tggtggtggt ggccacactt   3360
ggtggtgaca ggggaggagt agtgataatg ttcccatttc atagtaggaa gacaaccaag   3420
tcttcaacat aaatttgatt atccttttaa gagatggatt cagcctatgc caatcacttg   3480
```

```
agttaaactc tgaaaccaag agatgatctt gagaactaac atatgtctac ccctttttgag    3540
tagaatagtt ttttgctacc tggggtgaag cttataacaa caagacatag atgatataaa    3600
caaaaagatg aattgagact tgaaagaaaa ccattcactt gctgtttgac cttgacaagt    3660
cattttaccc gctttggacc tcatctgaaa aataaagggc tgagctggat gatctctgag    3720
attccagcat cctgcaacct ccagttctga aatattttca gttgtagcta agggcatttg    3780
ggcagcaaat ggtcattttt cagactcatc cttacaaaga gccatgttat attcctgctg    3840
tcccttctgt tttatatgat gctcagtagc cttcctaggt gcccagccat cagcctagct    3900
aggtcagttg tgcaggttgg aggcagccac ttttctctgg ctttatttta ttccagtttg    3960
tgatagcctc ccctagcctc ataatccagt cctcaatctt gttaaaaaca tatttcttta    4020
gaagttttaa gactggcata acttcttggc tgcagctgtg ggaggagccc attggcttgt    4080
ctgcctggcc tttgcccccc attgcctctt ccagcagctt ggctctgctc caggcaggaa    4140
attctctcct gctcaacttt cttttgtgca cttacaggtc tctttaactg tctttcaagc    4200
ctttgaacca ttatcagcct taaggcaacc tcagtgaagc ttaatacgg agcttctctg    4260
aataagagga aagtggtaac atttcacaaa aagtactctc acaggatttg cagaatgcct    4320
atgagacagt gttatgaaaa aggaaaaaaa agaacagtgt agaaaaattg aatacttgct    4380
gagtgagcat aggtgaatgg aaaatgttat ggtcatctgc atgaaaaagc aaatcatagt    4440
gtgacagcat tagggataca aaagatata gagaaggtat acatgtatgg tgtaggtggg    4500
gcatgtacaa aaagatgaca agtagaatcg ggatttattc taaagaatag cctgtaaggt    4560
gtccagaagc cacattctag tcttgagtct gcctctacct gctgtgtgcc cttgagtaca    4620
cccttaacct ccttgagctt cagagaggga taatcttttt atttttatttt attttatttt    4680
gttttgtttt gtttgttttt gttttatgag acagagtctc actctgttgc ccaggctgga    4740
gtgcagtggt acaatcttgg cttactgcat cctccacctc ctgagttcaa gcgattctcc    4800
ttcctcagtc tcctgaatag ctaggattac aggtgcaccc caccacaccc agctaatttt    4860
tgtatttta gtagagaagg ggtttcgcca tgttggccag gctggttttg aagtcctgac    4920
ctaaatgatt catccacctc ggcttcccaa agtgctggga ttacaggcat gagccaccac    4980
gcctggccca gagagggatg atctttagaa gctcgggatt cttttcaagcc ctttcctcct    5040
ctctgagctt tctactctct gatgtcaaag catggttcct ggcaggacca cctcaccagg    5100
ctccctccct cgctctctcc gcagtgctcc ttccaggacc tggacctctg ccctctggat    5160
ggcggcatcc agctacgaat ctccgaccac cactacagca agggcttcag gcaggccgcg    5220
tcagttgttg tggccatgga caagctgagg aagatgctgg ttccctgccc acagaccttc    5280
caggagaatg acctgagcac cttctttccc ttcatctttg aagaaggtag ttagccaaga    5340
gcaggcagta gatctccact tgtgtcctct tggaagtcat caagccccag ccaactcaat    5400
tcccccagag ccaaagccct ttaaaggtag aaggcccagc ggggagacaa aacaaagaag    5460
gctggaaacc aaagcaatca tctctttagt ggaaactatt cttaaagaag atcttgatgg    5520
ctactgacat ttgcaactcc ctcactcttt ctcagggcc tttcacttac attgtcacca    5580
gaggttcgta acctccctgt gggctagtgt tatgaccatc accattttac ctaagtagct    5640
ctgttgctcg gccacagtga gcagtaatag acctgaagct ggaacccatg tctaatagtg    5700
tcaggtccag tgttcttagc cacccactc ccagcttcat ccctactggt gttgtcatca    5760
gactttgacc gtatatgctc aggtgtcctc caagaaatca aattttgcca cctcgcctca    5820
cgaggcctgc ccttctgatt ttatacctaa acaacatgtg ctccacattt cagaacctat    5880
```

```
cttcttcgac acatgggata acgaggctta tgtgcacgat gcacctgtac gatcactgaa   5940
ctgcacgctc cgggactcac agcaaaaaag cttggtgatg tctggtccat atgaactgaa   6000
agctctccac ctccagggac aggatatgga gcaacaaggt aaatggaaac atcctggttt   6060
ccctgcctgg cctcctggca gcttgctaat tctccatgtt ttaaacaaag tagaaagtta   6120
atttaaggca aatgatcaac acaagtgaaa aaaatatta aaaaggaata tacaaacttt   6180
ggtcctagaa atggcacatt tgattgcact ggccagtgca tttgttaaca ggagtgtgac   6240
cctgagaaat tagacggctc aagcactccc aggaccatgt ccacccaagt ctcttgggca   6300
tagtgcagtg tcaattcttc cacaatatgg ggtcatttga tggacatggc ctaactgcct   6360
gtgggttctc tcttcctgtt gttgaggctg aaacaagagt gctggagcga taatgtgtcc   6420 atcccctcc ccagtcttcc ccccttgccc caacatccgt cccacccaat gccaggtggt   6480
tccttgtagg gaaattttac cgcccagcag gaacttatat ctctccgctg taacgggcaa   6540
aagtttcaag tgcggtgaac ccatcattag ctgtggtgat ctgcctggca tcgtgccaca   6600
gtagccaaag cctctgcaca ggagtgtggg caactaaggc tgctgacttt gaaggacagc   6660
ctcactcagg gggaagctat tgctctcag ccaggccaag aaaatcctgt ttctttggaa   6720
tcgggtagta agagtgatcc cagggcctcc aattgacact gctgtgactg aggaagatca   6780
aaatgagtgt ctctctttgg agccactttc ccagctcagc ctctcctctc ccagtttctt   6840
cccatgggct actctctgtt cctgaaacag ttctggtgcc tgatttctgg cagaagtaca   6900
gcttcacctc tttcctttcc ttccacattg atcaagttgt tccgctcctg tggatgggca   6960
cattgccagc cagtgacaca atggcttcct tccttccttc cttcagcatt taaaatgtag   7020
accctctttc attctccgtt cctactgcta tgaggctctg agaaaccctc aggcctttga   7080
ggggaaaccc taaatcaaca aaatgaccct gctattgtct gtgagaagtc aagttatcct   7140
gtgtcttagg ccaaggaacc tcactgtggg ttcccacaga ggctaccaat tacatgtatc   7200
ctactctcgg ggctaggggt tggggtgacc ctgcatgctg tgtccctaac cacaagaccc   7260
ccttctttct tcagtggtgt tctccatgtc ctttgtacaa ggagaagaaa gtaatgacaa   7320
aatacctgtg gccttgggcc tcaaggaaaa gaatctgtac ctgtcctgcg tgttgaaaga   7380
tgataagccc actctacagc tggaggtaag tgaatgctat ggaatgaagc ccttctcagc   7440
ctcctgctac cacttattcc cagacaattc accttctccc cgcccccatc cctaggaaaa   7500
gctgggaaca ggtctatttg acaagttttg cattaatgta aataaattta acataatttt   7560
taactgcgtg caaccttcaa tcctgctgca gaaaattaaa tcattttgcc gatgttatta   7620
tgtcctacca tagttacaac cccaacagat tatatattgt tagggctgct ctcatttgat   7680
agacaccttg ggaaatagat gacttaaagg gtcccattat cacgtccact ccactcccaa   7740
aatcaccacc actatcacct ccagctttct cagcaaaagc ttcatttcca agttgatgtc   7800
attctaggac cataaggaaa aatacaataa aaagcccctg gaaactaggt acttcaagaa   7860
gctctagctt aattttcacc cccccaaaaa aaaaaaattc tcacctacat tatgctcctc   7920
agcatttggc actaagtttt agaaagaag aagggctctt ttaataatca cacagaaagt   7980
tgggggccca gttacaactc aggagtctgg ctcctgatca tgtgacctgc tcgtcagttt   8040
cctttctggc caacccaaag aacatctttc ccataggcat ctttgtccct tgccccacaa   8100
aaattcttct ttctctttcg ctgcagagtg tagatcccaa aaattaccca agaagaaga   8160 tggaaaagcg atttgtcttc aacaagatag aaatcaataa caagctggaa tttgagtctg   8220
```

-continued

| | |
|---|---|
| cccagttccc caactggtac atcagcacct ctcaagcaga aaacatgccc gtcttcctgg | 8280 |
| gagggaccaa aggcggccag gatataactg acttcaccat gcaatttgtg tcttcctaaa | 8340 |
| gagagctgta cccagagagt cctgtgctga atgtggactc aatccctagg gctggcagaa | 8400 |
| agggaacaga aaggttttttg agtacggcta tagcctggac tttcctgttg tctacaccaa | 8460 |
| tgcccaactg cctgccttag ggtagtgcta agaggatctc ctgtccatca gccaggacag | 8520 |
| tcagctctct cctttcaggg ccaatcccca gccctttgt tgagccaggc ctctctcacc | 8580 |
| tctcctactc acttaaagcc cgcctgacag aaaccacggc cacatttggt tctaagaaac | 8640 |
| cctctgtcat tcgctcccac attctgatga gcaaccgctt ccctatttat ttatttattt | 8700 |
| gtttgtttgt tttgattcat tggtctaatt tattcaaagg gggcaagaag tagcagtgtc | 8760 |
| tgtaaaagag cctagttttt aatagctatg gaatcaattc aatttggact ggtgtgctct | 8820 |
| ctttaaatca agtcctttaa ttaagactga aaatatataa gctcagatta tttaaatggg | 8880 |
| aatatttata aatgagcaaa tatcatactg ttcaatggtt ctgaaataaa cttcactgaa | 8940 |
| gaaaaaaaaa aaagggtctc tcctgatcat tgactgtctg gattgacact gacagtaagc | 9000 |
| aaacaggctg tgagagttct tgggactaag cccactcctc attgctgagt gctgcaagta | 9060 |
| cctagaaata tccttggcca ccgaagacta tcctcctcac ccatcccctt tatttcgttg | 9120 |
| ttcaacagaa ggatattcag tgcacatctg gaacaggatc agctgaagca ctgcagggag | 9180 |
| tcaggactgg tagtaacagc taccatgatt tatctatcaa tgcaccaaac atctgttgag | 9240 |
| caagcgctat gtactaggag ctgggagtac agagatgaga acagtcacaa gtccctcctc | 9300 |
| agataggaga ggcagctagt tataagcaga acaaggtaac atgacaagta gagtaagata | 9360 |
| gaagaacgaa gaggagtagc caggaaggag ggaggagaac gacataagaa tcaagcctaa | 9420 |
| agggataaac agaagatttc cacacatggg ctgggccaat tgggtgtcgg ttacgcctgt | 9480 |
| aatcccagca ctttgggtgg caggggcaga aagatcgctt gagcccagga gttcaagacc | 9540 |
| agcctgggca acatagtgag actcccatct ctacaaaaaa taaataaata aataaaacaa | 9600 |
| tcagccaggc atgctggcat gcacctgtag tcctagctac ttgggaagct gacactggag | 9660 |
| gattgcttga gcccagaagt tcaagactgc agtgagctta tccgttgacc tgcaggtcga | 9720 |
| c | 9721 |

<210> SEQ ID NO 3
<211> LENGTH: 12565
<212> TYPE: DNA
<213> ORGANISM: Homo sapiens

<400> SEQUENCE: 3

| | |
|---|---|
| gtcgacctgc aggtcaacgg atctgagagg agagtagctt cttgtagata acagttggat | 60 |
| tatataccat gtcctgatcc ccttcatcat ccaggagagc agaggtggtc accctgatag | 120 |
| cagcaagcct gggggctgca gcttggtggg tagaggtact caggggtaca gatgtctcca | 180 |
| aacctgtcct gctgccttag ggagcttcta ataagttgat ggatttggtt aaaattaact | 240 |
| tggctacttg gcaggactgg gtcagtgagg accaacaaaa agaagacatc agattatacc | 300 |
| ctgggggttt gtatttcttg tgtttctttc tcttctttgt actaaaatat ttacccatga | 360 |
| ctgggaaaga gcaactggag tctttgtagc attatcttag caaaaattta caagtttgg | 420 |
| aaaacaatat tgcccatatt gtgtggtgtg tcctgtgaca ctcaggattc aagtgttggc | 480 |
| cgaagccact aaatgtgaga tgaagccatt acaaggcagt gtgcacatct gtccacccaa | 540 |
| gctggatgcc aacatttcac aaatagtgct tgcgtgacac aaatgcagtt ccaggaggcc | 600 |

-continued

```
caaatgaaaa tgtttgtact gaaatttgtt aaagcttccc gacaaactag atttatcagt      660
aaggattgtt ttctgcaagg gggatgaaac ttgtggggtg agccatttgg gctgaggagg      720
agggaggttg gagctgagaa atgtggagac aatttccctt tagaaggact gaatctccct      780
gcctctctgg ggtgcggcag ccagcaggat ccaatggtgt atatgtctcc ccagctcccc      840
attcagtgat atcatgtcag tagcttgaaa ttatccgtgg tgggagtatt atgtcatgga      900
aattggcaaa tggaaacttt tattggagat tcaattgtta aacttttacc agcacaacac      960
tgccctgcct tcagagtcaa tgaccctatc caagtttaat ccatctgtcc actgtctcca     1020
acacgatctt tataaaacac acctgacaac attacccttt tattcagttt tttaaaagat     1080
aagtttccag ctcatcgggg tggctttaaa ggccatttct cctctggacc tcacccaact     1140
tttcaaatca ctttcctac ccctacctct aaatgctact caaactccag ccatcctgaa      1200
taataagact tttgaaaagt agattatggg ctgggcacag tggctcacac ctgtaatccc     1260
agcactttgg gaggccaaga tgggtggatc acctgaggtc gggagttcga gaccagcctg     1320
actaacatag tgaaaccctg tctctactaa aaatacaaaa ttagttgggg gtggtggcac     1380
aagcctgtaa tcccagctac tcaggaggtt gaggcagggg aattgcttga acctgggagg     1440
cggaggttgc ggtgagccta gattgctcca ctgcactcca gcctgggcaa caagagcgaa     1500
actccatctc aaaaaaataa ataaataaat aaagtagatt acatcagata cctctggcct     1560
aggttgttta tgaccaactc tcctgctgag ataactaga aaagctagac aaaacatatt      1620
tccaaaagat ctctttggag gcatcagaga atggccaagg ctgtaaggaa ctgcctgagc     1680
ccagagaggt ggagcccagc actggtgccc tttactcctg gggacatgtg ctggtttcaa     1740
aaacttcagc tgagcttttg agcattcatg gaacttggtg ggggagatga aatttgtacc     1800
ttaaatcctg cctacaggga gggtccctga taatccccac ccaatttgga aatctgggtc     1860
agccttcaca ggtactgaag ccctcctctg aatgatctca agtcctgcta gggtagaggt     1920
tacctgcttt tgaaaggctc ctggcctacc tgtgcagcag gagcaaaagt gaaccatctc     1980
agggtacaga taacaatcat ccagagcctt gaatgacctc tactgtgctt aatatatagt     2040
attcagcagt cagtaaaaag gatttaggca catgcaagat gacctgtgta tcagggagaa     2100
ataggcaata aattgagatc cagcagggat ttgaatcatg gatttgaatc aggggcagcc     2160
ttcgaaagaa ctatggagaa tatactcaga tttaaaacat aagattggaa tttttggcag     2220
agaactaaca actgtacaaa aaaggaacca atggaaatc ctagaactga aagatgcaat      2280
taaccgatgt tgagaaatag ccaacatcta ttgaacactt cccatgtgga cagctgtgct     2340
aaacacttta caggcatcaa cataagatgt gtccccttac agcagtgcag tgtccctcct     2400
aagacatgga cagcctggtt tccctatctc tctgcttcat caaaacccct ttacgtgggg     2460
cttagacact cctgttgtct ctagtgtcta gtagcacagg gctcagcaca tggaagccac     2520
tagatacaat tgatgaccca ggacctccga tgaaagccat gggtgctgat tgggaaggca     2580
ttgtctttta tgtgctatgg tcttaaagct tcatccagga agcagaactc gggggtgct      2640 gaggacccag aaccgagaat aagattagtc agagatttcc tgtgggcaga atcataagg      2700 acgccaactg tttgggtgag ataagacgaa accaagagtg gacttgtggc cagaagcgtg     2760
aggaagaggg agagagcttc ccttgtcccc tttcttcctc tccctaagcc acagtgattg     2820 acagccccc cgctttggag tcagagcagg cttgagactg gactgggaaa ggagggtggg     2880
tcaggataca gagcaggaag gctgggagtg cagggcagga gcaaggggct ggggcattca     2940
```

-continued

```
ttgtgcctga tctctcccac tttacctggg gtaaagaagc atatgcaaaa gccacggtgt      3000
gagtatttcc caagtgccag ggtcagggca tgattcatca cgtgcagcat ttcattcaat      3060
ccttatagta accgatgatg tggcttctat tattagctct atcagataat gaaactgaga      3120
ccaagacagg ctctgcacat tgtgtgggt aatgacacag ggggattcag acctagactc       3180
cataactcct gccccaggga ccaccccac cctcaccctg tgcatgtcga caaaggacag       3240
actgggccac ttctcaggac acagcgggga atgacacag agcagggagg ttccaggagc       3300
cccgagcgtc ttttctccag gagaatactc tctgaattca gactgggtc agagaaacat       3360 ttacccagga gccgcagtgt gggtggggct ttttacttga aacgctgtct gaaggcagtg      3420
gcaggatgaa ctctccaccc taccttggca agccacttct cttctgcaat ctgtaaggac      3480
attgttgaga gaattatggt cttccaattc cggagggttg aagaaagaca aataggagag      3540
aacctatcat agtcaggtgc tagctgcctt ctctttcaga gagtgtgaga ataaagtgat      3600
acacttgatt attagcaaat actttggaaa ttttaaacgc taatattcaa cacactctgg      3660
aagaggcaaa taagtagaca ggttcatata catcatctcc ttcagctagt cctcacaaaa      3720
acaaacaaat gaataaacaa aattcttctt tggccctcat aggaagacac tgtttcttga      3780
acgtgtttca aaaaggatgg gtgactcact caaggtcaca ctgttttatga ggacagtaca     3840 ggaatacaga catgccattt tgcctgaaaa aatccatcac ccagggaggt gacacaattt      3900
tgcagaaatg ttctatttcc tctgaaggat acattcttta aacctttggg aaattcattc      3960
atagtcttcc tcctttgaag gattactctc tggacacaaa gtgtttgatt ctgatttgtt      4020
ggttggaaga tgtgttggtt gagagaaaga ttctgatttg ttggttgaaa atagactcat      4080
caagatcaac tgctgtagta gtaaatattt tgacattttg tctgtattcc tgtgctgccc      4140
tcacaagctg catcaccttg agtgagtcat tcatactttt ttgtttgttt ttgttttgga      4200
gatggagtct tactctgttg cctaggctgg agtgcggtgg cgtgatcttg gctcactgcg      4260
acctccatct cctgggttca agtgatcctc ctgcctcagc ctcccgagta gctgggatta      4320
caggcacatg ccaccatccc tgctaatttt tgcattttca gtagagacgg agtttcacca      4380
tgttggtcag gttggtcttg aactcctgac ctcaggtgat ccgcccacct cagcctcccc      4440
aagtgctggg attacaggtg tgagccaccg tgcccagccc agccatcatt tttgaaacac      4500
gtttgagaaa tagtgtcttc ctttgagggc caaggagaca ttttttttgt ttatttgttt      4560 gttttttgtga ggactagctg aagggggtga tgtatattaa cctgcctact tatttgcctc     4620
ttcccagagt gtgatgaata ttagggttta agtttctga agcatttgtt aataaagccc       4680
ggggctggag gtcagaagac ctggatttct ctgcatactt ttgccatcag caagctgtgt      4740
gaccttggac agatcccttt tttgtctaaa tctttctgag tcttcttgaa aacaatgcca      4800
ggttgggaca ggatgattgc caagctcccg tccagctcta aaacactgca acgtatgctt      4860
ctgcaccagc actgtccatc ctgtagatca tgcagaaatt ctcttcaact ttttcctacc      4920
cataaaatag gagcatgctt accttttttcc taatgttcca ggccccgggt ctagatattg      4980
taagtaagga agttaatgtg tatcagagcc cattatgggc cagaagttct cctcttcctt      5040
cctacacctg cttcctcccct ccctccctcc ctctttccct tccttccttc catccatttg      5100
tgaagaagac atgatcaccc tcattctgag agtgaagaga cagaggctca actaatgaaa       5160
tgatttgttc aaggtcacac gggtggcaca aggcaagtgg cagaggttga atttagaccc      5220
attcctgtcc aaatgctgag tttatgtcat cgtcccgaga ccataacttt aaagatgtaa      5280
gatagtggga aaagagttga tttcaaagca cctctcagaa ggactcactt tacatcaggg      5340
```

-continued

```
gtcagcagac tcaggccaaa tccggtccat tccccgcttt tgcaaagaaa gttgtagtgg    5400
aacacagcta ggcttattga tttatggatt gccaacgtcc ttttgtgaaa cagacagctg    5460
agctgagtaa tcgtggcgca caaaacctaa aatatttact atctcgtcct ttacagaatg    5520
tttgccaatc tatggtccgg agtccaaggc tgtccatttt tcaaagaaca caaagtgaca    5580
tgagactgtc ccatgtgcag ggagccctat cattttatta tgaaaaaacg gcctttctgc    5640
tcaaatctgt tttttaaaaa gtcaacaaac agactctggg tacctgtcag aacagtagg     5700 gagtttggtt tccattgtgc tcttcttccc aggaactcaa tgaaggggaa atagaaatct    5760
taattttggg gaaattgcac aggggaaaaa ggggagggaa tcagttacaa cactccattg    5820
cgacacttag tggggttgaa agtgacaaca gcaagggttt ctcttttttgg aaatgcgagg   5880 agggtatttc cgcttctcgc agtggggcag ggtggcagac gcctagcttg ggtgagtgac    5940 tatttctttta taaaccacaa ctctgggccc gcaatgcgca tccactgctt gctgcagtca   6000
cagaatggaa atctgcagag gcctccgcag tcacctaatc actctcctcc tcttcctgtt    6060
ccattcagag acgatctgcc gaccctctgg gagaaaatcc agcaagatgc aagccttcag    6120
gtaaggctac cccaaggagg agaaggtgag ggtggatcag ctggagactg gaaacatatc    6180
acagctgcca gggctgccag gccagagggc ctgagaactg ggtttgggct ggagaggatg    6240
tccattattc aagaagagg ctgttacatg catgggcttc aggacttgtg tttcaaaata     6300
tcccagatgt ggatagtgcg accggagggc tgtcttactt tcccagagac tcaggaaccc    6360
agtgagtaat agatgcatgc caaggagtgg gactgcgatt caggcctagt tgaatgtgct    6420
gacagagaag cagagagggg caccagggc acagcccgaa ggcccagact gatatgggca     6480
aggcctgtct gtgctgacat gtcggagggt cccactctcc agggaccttg gtttccccgt    6540
ctgtgacatc tgtgacatga gagtcacgat aactccttgt gtgccttaca ggggttgttgt   6600 gaaaattaaa tgcacagata atagcgtaac agtattccgt gcattgtaaa gagcctgaaa    6660
accattatga tttgaaaatg gaatcggctt tgtgagacca tcactattgt aaagatgtga    6720
tgctgataga aatgacagga ctgcttgtgc atgccctctg cagtgtgaca ttccagcagt    6780
gaaatcatgt tggggtgact tctcccccac tctgacctttt atgtttgtct gggccgaggc   6840
tgcaagtcgg gctctgtggg tgtatgagtg acaagtctct cccttccaga tatggggact    6900
gtctgcttcc ctaggttgcc tctccctgct ctgatcagct agaagctcca ggagatcctc    6960
ctggaggccc cagcaggtga tgtttatccc tccagactga ggctaaatct agaaactagg    7020
ataatcacaa acaggccaat gctgccatat gcaaagcact ttggtttgcc tggccacccc    7080
tcgtcgagca tgtgggctct tcagagcacc tgatgaggtg ggtacagtta gccacacttc    7140
acaggtgaag aggtgaggca caggtcccag gtcaggctgg ccggagctct gtttattacg    7200
tctcacagct ttgagtcctg ctctcaacca gagaggccct taccaagaa gaaaggattg      7260 ggacccagaa tcaggtcact ggctgaggta gagaggaagc cgggttgttc ccaagggtag    7320
ctgctcctgc aggactctga gcaggtcacc agctaatgga ggaaaggctc tagggaaaga    7380
cccttctggt ctcagactca gagcgagtta gctgcaaggt gttccgtctc ttgaaacttc    7440
tacctaggtg ctatgtagc cactagtctc aggtggctat ttaaatttat acttaaatga     7500
atgaaaatag aagaaaattt aaaatccaga cccttggtca cactatccac atttaaagag    7560
gtcaatagcc acatgtggtt agtggccacc ctattgggca gtgcagctac agaacatttt    7620
tgcatcccag aaagttcttt tggatgttgc tgctctacag catgctttgc tgaaacagaa    7680
```

-continued

| | | | | |
|---|---|---|---|---|
| gtgccttccc | tgggaatctc | agatgggaag | caagtaagga | ggggagtcaa atgtgggctc | 7740 |
| actgctcacc | agctgtgagg | gttgggcctg | cctcttaacc | attgtcagcc tcagtcttct | 7800 |
| catccatgca | tgccgtgggt | atactaaaat | actataccc | tggaagagct ggatgcaaat | 7860 |
| ttgacaagtt | ctgggggaca | caggaaggtg | ccaagcacaa | ggctgggcac atggtggctg | 7920 |
| tgcactacag | ctgagtcctt | ttccttttca | gaatctggga | tgttaaccag aagaccttct | 7980 |
| atctgaggaa | caaccaacta | gttgctggat | acttgcaagg | accaaatgtc aatttagaag | 8040 |
| gtgagtggtt | gccaggaaag | ccaatgtatc | tgggcatcac | gtcactttgc ccgtctgtct | 8100 |
| gcagcagcat | ggcctgcctg | cacaaaccct | aggtgcaatg | tcctaatcct tgttgggtct | 8160 |
| ttgtattcaa | gtttgaagct | gggagggcct | ggctactgaa | gggcacatat gagggtagcc | 8220 |
| tgaagagggt | gtggagaggt | agagtctagg | tcagaggtca | gtgcctatag gcaagtggtc | 8280 |
| ccagggccac | agctgggaag | ggcaaatacc | agaaggcaag | gttgaccatt cccttcctca | 8340 |
| agtgcctatt | aaggctccat | gttcctatgt | tgttcaaacc | ctaactcaat cccaaattaa | 8400 |
| tccaccatgt | ataaggttga | gctatgtctc | ttattcctgg | acaccatact cagccatatc | 8460 |
| tggtccacac | attaacagct | ggatgacctt | gaagaagctt | cacccactct gttcctcagc | 8520 |
| tttcccttca | gtgggatgat | atcaactgga | caacaggatg | tgcgattctt ttagttccag | 8580 |
| ccttccagga | tgttttcact | cccctgtttg | ttgttgtagg | atggtattac ctccaccttc | 8640 |
| ccaccttccc | tatgccctgg | ttctgtctcc | tgtgcctcgc | tctgaaagtg atgagacct | 8700 |
| acaattcctg | tcctggtagt | tctcctaatg | aacacactga | agcacgagga agctgagatt | 8760 |
| tttgttgcta | catgagagca | tggaggcctc | ttagggagag | aggaggttca gagactccta | 8820 |
| ggctcctggt | ggagccccac | tcatggcctt | gttcattttc | cctgccctc agcaacactc | 8880 |
| ctattgacct | ggagcacagg | tatcctgggg | aaagtgaggg | aaatatggac atcacatgga | 8940 |
| acaacatcca | ggagactcag | gcctctagga | gtaactggg | agtgtgcatc ctggggaaag | 9000 |
| tgagggaaat | atggacatca | catggaacaa | catccaggag | actcaggcct ctaggagtaa | 9060 |
| ctgggtagtg | tgcatcctgg | ggaaagtgag | ggaaatatgg | acatcacatg gaacaacatc | 9120 |
| caggagactc | aggcctctag | gagtaactgg | gtagtgtgca | tcctggggaa agtgagggaa | 9180 |
| atatggacat | cacatggaac | aacatccagg | agactcaggc | ctctaggagt aactgggtag | 9240 |
| tgtgcttggt | ttaatcttct | atttacctgc | agaccaggaa | gatgagacct ctctgccctt | 9300 |
| ctgacctcgg | gattttagtt | ttgtggggac | caggggagag | agaaaaatac ccggggtctc | 9360 |
| ttcattattg | ctgcttcctc | ttctattaac | ctgaccctcc | cctctgttct tccccagaaa | 9420 |
| agatagatgt | ggtacccatt | gagcctcatg | ctctgttctt | gggaatccat ggagggaaga | 9480 |
| tgtgcctgtc | ctgtgtcaag | tctggtgatg | agaccagact | ccagctggag gtaaaaacat | 9540 |
| gctttggatc | tcaaatcacc | ccaaaaccca | gtggcttgaa | acaaccaaaa ttttttctta | 9600 |
| tgattctgtg | ggttgaccag | gattagctgg | gtagttctgt | tccatgtggt ggaacatgct | 9660 |
| ggggtcactt | tggaagctgc | attcagcaga | gtgccaggct | tgcgctgggc atccaaggtg | 9720 |
| gtccctcatc | ctccaggctc | tctttccatg | tgatctctca | gtgtttaaga gttagttgga | 9780 |
| gcttccttac | agcatggcgg | ctgacttcca | aaagggatta | ttccaaaaag agcctcaaca | 9840 |
| tgcaggcgct | tattatgact | tctgcttgca | tcatcctatt | ggccaaagcc agtcacgtgg | 9900 |
| ctaagtctag | cccctgtga | gaggagactg | cataagagtg | tgaacaccag gagacacggt | 9960 |
| cactgggggc | caccactgta | accatctacc | acaggacctg | aatctctgtg tgctactccc | 10020 |
| ttgctcaagg | gccccctac | ccacgcagac | ctgctgtctt | ctagcaaagc ccatcctcag | 10080 |

-continued

```
gacctttctc ttccaatcct tattgactca aattgattag ttggtgctcc acccagagcc    10140
ctgtgctcct ttatctcatg taatgttaat gggtttccca gccctgggaa aacatggctt    10200
tgtctcaggg gcttgctgga tgcaacctta acctcaatgt gagtggccat actgtggcac    10260
tgtcccatcc ctcaccaggg acactgttct ggagggtgac tgcctgttct gtgaggagtg    10320
gggatggcta ggacattgca tggaacacac caccacccca tcttctcaga gctcaaaccc    10380
tgacagaaca ccagctccac aggccttggc ttctgctgat ggtgccgtgt atttaccaga    10440
cttagtggtc caaggccaga gtggcagatt cccaaagtc aaggtgtgac agtgggacag    10500
cctctttgtg tctttgctgt cctaagaaac ctgggccagg ccaggcgcag tggctcacgc    10560
cttgtaatcc cagcactttg agaggccaag gtgggcagat cacgaggtca ggagtttgag    10620
accagcctgg ccaacattgg tgaaaccctg tctctattaa aaatagaaaa cattagacag    10680
gtgtggtggt gcatgcctgt aatcccagct actcaggagg ctgaggcagg agaatcgctt    10740
gaacccagga ggtggaggtt gcagtgagcc gagattgtgc cactgcactc cagcctaggc    10800
gacagagcaa gactccgtct cggaaaaatt aattaataaa taaataaacc taggtcccag    10860
agtcccacag aatggcagac aggagcacct gggggctttt agggtatggc atttcccctg    10920
tactaactct gggctgtcca gaggcgattt catggcgtgg agtggagagg gaggcagcac    10980
aggacttcct aggcctcagc tctcacctgc ccatcttttg atttccaggc agttaacatc    11040
actgacctga gcgagaacag aaagcaggac aagcgcttcg ccttcatccg ctcagacagt    11100
ggccccacca ccagttttga gtctgccgcc tgccccggtt ggttcctctg cacagcgatg    11160
gaagctgacc agcccgtcag cctcaccaat atgcctgacg aaggcgtcat ggtcaccaaa    11220
ttctacttcc aggaggacga gtagtactgc ccaggcctgc ctgttcccat tcttgcatgg    11280
caaggactgc agggactgcc agtccccctg ccccagggct cccggctatg ggggcactga    11340
ggaccagcca ttgaggggtg gaccctcaga aggcgtcaca acaacctggt cacaggactc    11400
tgcctcctct tcaactgacc agcctccatg ctgcctccag aatggtcttt ctaatgtgtg    11460
aatcagagca cagcagcccc tgcacaaagc ccttccatgt cgcctctgca ttcaggatca    11520
aaccccgacc acctgcccaa cctgctctcc tcttgccact gcctcttcct ccctcattcc    11580
accttcccat gccctggatc catcaggcca cttgatgacc cccaaccaag tggctcccac    11640 accctgttt acaaaaaaga aaagaccagt ccatgaggga ggttttttaag ggtttgtgga    11700 aaatgaaaat taggatttca tgatttttt ttttcagtcc ccgtgaagga gagcccttca    11760
tttggagatt atgttctttc ggggagaggc tgaggactta aaatattcct gcatttgtga    11820
aatgatggtg aaagtaagtg gtagcttttc ccttcttttt cttcttttt tgtgatgtcc    11880 caacttgtaa aaattaaaag ttatggtact atgttagccc cataattttt tttttccttt    11940
taaaacactt ccataatctg gactcctctg tccaggcact gctgcccagc ctccaagctc    12000
catctccact ccagattttt tacagctgcc tgcagtactt tacctcctat cagaagtttc    12060
tcagctccca aggctctgag caaatgtggc tcctgggggt tctttcttcc tctgctgaag    12120
gaataaattg ctccttgaca ttgtagagct tctggcactt ggagacttgt atgaaagatg    12180
gctgtgcctc tgcctgtctc cccaccaggc tgggagctct gcagagcagg aaacatgact    12240
cgtatatgtc tcaggtccct gcagggccaa gcacctagcc tcgctcttgg caggtactca    12300
gcgaatgaat gctgtatatg ttgggtgcaa agttccctac ttcctgtgac ttcagctctg    12360
ttttacaata aaatcttgaa aatgcctata ttgttgacta tgtccttggc cttgacaggc    12420
```

```
tttgggtata gagtgctgag gaaactgaaa gaccaatgtg tyttycttac cccagaggct   12480
ggcgcctggc ctcttctctg agagttcttt tcttccttca gcctcactct ccctggataa   12540
catgagagca aatctctctg cgggg                                         12565

<210> SEQ ID NO 4
<211> LENGTH: 5670
<212> TYPE: DNA
<213> ORGANISM: Homo sapiens

<400> SEQUENCE: 4
ggatccccgc tgacaatcta gaaacaagca acagaccctc tgatgtagcc atctgtgccg     60
cgcctctccg caccgcccgc cacgccttgg tccctggaga ccaccctcca gggcaggggc    120
tgccgctcgg ccgggcccgc ggggtccctc ggcctgacat ggccggtgct ggagcggcac    180
gtgcgcgcct cggcccctcg gccgctcccg ccctcgccg gtgcgcaccg cgctcgggg     240 agccgctggc ccgggtgtcc agccggccct tgccctgcct ggcgctcgga ccgccacctt    300
tgccgccccc tcgccagcct ccgcagcttc cagactggcc ggtctgcgcg cccaccctg    360 cctcccggac cggccaccgc cggaggccgc ggaggagggc ccggccgcgc agatcccgct    420
tatcgggccc catctcccgt tacataaggc caccccccta tctccgcggg ccatcgccgc    480
cgcaaccgcc gcgccagcgc cttctcccac gcgcgggggc gccctgccc accgctcccg    540 gcagggcttt tggtggccat gggggataag gggcgttgac tcacccgggc ggggctccgg    600
gagttgcaca gaccaaggta gttccccgct ccttccccca tcacggagac cctgtgggag    660
atgccgtggg ccctctacta cagattagga aacaggcccg tagaggggtc gcgcggccaa    720
gtagcggcac tccaggcact gggggccctc gagggaaggg gcagacttct gggagtcaga    780
gccagcagct gggctgggaa gcttcgagtg tggacagaga gggtgggaat gacgttccct    840
gtgggaagag agggtgggca agcctgggat gcctctgagc gggaatccag catgccttgt    900
gaggagggtc acaagcacac ccttgtgagg aggttgagcc ccatcgagga caggacggag    960
ggagcctgag caggcagaga gggggcctgg ggaggcgctg gttcggggag gaagtgggta   1020
ggggagaaat cttgacatca acacccaaca ggcaaatgcc gtggcctctg ctgtggggt    1080 ttctggagga cttctaggaa aacgagggaa gagcaggaaa aggcgacatg gctgtagggc   1140
caagcccagg agccgccctc cacagcactc attctgcaga agggaaattt gaggccccca   1200
gacggcaggg gttgatcctg cagagactgg tgagcaaagg ggatcacccc aagccccagt   1260
ggcactagga acacttacaa tctctgacct ggactaaggc tgccagcctg cccagttaa    1320 gagtttccca gaaggatggc ccatacactt taaattaaag gggccagaca cgtgcacact   1380
acttccagcc actctggaag ctgaggtggg gggatcgctt gagtctggga gttggaggcc   1440
agcctaggca ggcaacatag tgagacccca tctccaaaaa aacaaaacaa acaaaaacaa   1500
aaaaacacca aaaagctcc cagaaagacc tctgaatctt tctggatctc tcagtggaga   1560
cctggaaatc tgaactttga caatccctct cacagtgggg ccaaggagga attaggcaag   1620
ccaaaagaag tgaactttac tcttctattg cctgtttgaa ttttgtatcc aagcaagtgt   1680
tacttaagta atttaagaga ctggttcatc gaaaaaataa aactcccaa attcccatag    1740 ctggtagact gtggtcacag ccacagtgca ctaagactat ctgctcagca cttctggtga   1800
cccaaaaggg tctgaggaca ggagctcaga gttgggtcag ctgtccaggt actcagggtt   1860
gtcacaggca aaactgctgg aactcagggc agcattgcaa atgccacgcc gctctcaggg   1920 cccctttgcct gccgctggaa ttaaacccac ccagatcttg gaaactctgc cctggaccct   1980
```

```
tctcaataag tccatgagaa atcaaactct ttcctttatg cgacactgga ttttccacaa    2040
agtaaaatca agatgagtaa agatgtggtt tctagatagt gcctgaaaaa gcagagacca    2100
tggtgtcagg cgtcaccact tgggcctata aaagctgcca caagacgcca aggccacaag    2160
ccacccagcc tatgcatccg ctcctcaatc ctctcctgtt ggcactgggc tcatggcgc     2220 ttttgttgac cacggtcatt gctctcactt gccttggcgg ctttgcctcc ccaggccctg    2280
tgcctccctc tacagccctc agggagctca ttgaggagct ggtcaacatc acccagaacc    2340
agaaggtgag tgtcggctag ccagggtcct agctatgagg gctccagggt gggtgattcc    2400
caagatgagg tcatgagcag gctgggcctg gtcctaagat gcctgtaggt caggaaaaat    2460
ctccatggac caaggcccgg cccagccatg agggagagag gagctgggct gggggggctca   2520 gcactgtgga tggacctatg gaggtgtctg gcagactccc cagggactac ctgctctcct    2580
ggcctggcct tgtctgccac tgccagtccc tactcagcca ttcctgaaca gaggacagca    2640
gagaagggcc agcaccctcc cagaaccatg tggcatttgc caactggatt ttgaccataa    2700
caatgcagcc attctcccca gcaccatcat aggcccgccc ttacaggagg attcgttagt    2760
agagtccgct ccttgcccca ctagtaacag ctcacatgtc tgagcactgc ttacaccagg    2820
cctggtgcac gtgctttatg tgtcatttca tcactgccag ccacctcaag aggcaggtac    2880
gatgaaccca ttctgctaag gttcagtgag gttaagtgac agaggctgga ttcaagccag    2940
gcctggccaa caccagagtg tccatgctcc taactgcagt gttccctcac catcagaagg    3000
cagggcattt aatacaccag atccccaccg cctcccatct gatttgtctt ggtcaacagt    3060
ggcccaggcc actcctactt cactcgtccc caccctggcc cttcccgcag gcccctgtcc    3120
tcctgccctg actatggcaa gccttgcatg cagcttgtcc cttactagtg gtgtcaattt    3180
ttttctctca gctccaagac cctaaacagt gggacctcac ccctatgcct gctgttcaaa    3240
gcagaaaacg aagctcagga atgctgaggg gctgccaggc ctgcctctgt gccacaccag    3300
ggatgcttgt ggggcctgtg ctggggcaga cctggcctgg gctgccaggg caggcccaca    3360 accccctgcca gcactctgct cactgtcact ttgctcccac aggctccgct ctgcaatggc    3420
agcatggtat ggagcatcaa cctgacagct ggcatggtaa ggacctttgg gtgcagggag    3480 gatgggggcag aggctccagg ccttgggctt atcttctctg agcctccctt ccatggctgg   3540
ggttccaagc aagcttcaag tgctctcctc cctcccgcca taatctggcc ccttcccgcc    3600
caccacccag actcacctgc gccaggcatc tcagcccccat cttcctgcag actcacaaaa   3660
ggcagctgcc caagcagggc ctgacccctc ggtgtcccct ccccacagta ctgtgcagcc    3720
ctggaatccc tgatcaacgt gtcaggctgc agtgccatcg agaagaccca gaggatgctg    3780
agcggattct gcccgcacaa ggtctcagct ggggtaaggc atcccccacc ctctcacacc    3840
caccctgcac ccctcctgc caaccctggg ctcgctgaag ggaagctggc tgaatatcca     3900
tggtgtgtgt ccacccaggg gtggggccat tgtggcagca gggacgtggc cttcgggatt    3960
tacaggatct gggctcaagg gctcctaact cctacctggg cctcaatttc acatctgta     4020 cagtagaggt actaacagta cccacctcat ggggacttcc gtgaggactg aatgagacag    4080
tccctggaaa gccctggtt tgtgcgagtc gtcccgcct ctggcgttct actcacgtgc      4140
tgacctcttt gtcctgcagc agttttccag cttgcatgtc cgagacacca aaatcgaggt    4200
ggcccagttt gtaaaggacc tgctcttaca tttaaagaaa cttttcgcg agggacggtt     4260 caactgaaac ttcgaaagca tcattatttg cagagacagg acctgactat tgaagttgca    4320
```

-continued

```
gattcatttt tctttctgat gtcaaaaatg tcttgggtag gcgggaagga gggttaggga    4380
ggggtaaaat tccttagctt agacctcagc ctgtgctgcc cgtcttcagc ctagccgacc    4440
tcagccttcc ccttgcccag ggctcagcct ggtgggcctc ctctgtccag ggccctgagc    4500
tcggtggacc cagggatgac atgtccctac acccctcccc tgccctagag cacactgtag    4560
cattacagtg ggtgcccccc ttgccagaca tgtggtggga cagggaccca cttcacacac    4620
aggcaactga ggcagacagc agctcaggca cacttcttct tggtcttatt tattattgtg    4680
tgttatttaa atgagtgtgt ttgtcaccgt tggggattgg ggaagactgt ggctgctggc    4740
acttggagcc aagggttcag agactcaggg ccccagcact aaagcagtgg accccaggag    4800
tccctggtaa taagtactgt gtacagaatt ctgctacctc actggggtcc tggggcctcg    4860
gagcctcatc cgaggcaggg tcaggagagg ggcagaacag ccgctcctgt ctgccagcca    4920
gcagccagct ctcagccaac gagtaattta ttgtttttcc tcgtatttaa atattaaata    4980
tgttagcaaa gagttaatat atagaagggt accttgaaca ctgggggagg ggacattgaa    5040
caagttgttt cattgactat caaactgaag ccagaaataa agttggtgac agataggcct    5100
gattgtattt gtctttcatt ttggcctttg gggacactgg tctgtggtct gaagactctg    5160
aggagctctt cggaggctg gtgggttgga ggagggact gggatggatt acagcgaggg    5220
tagggtgcag tgacctgggc tgaatgcaag ctagctcccg agggtgggga catggcctga    5280
aggaagcccc accttctgtc tgctgcacca gcaaggacgg agaggcttgg gccagactgt    5340
cagggttcaa ggagggcatc aggagcagac ggagacccag gaagtctcac aatcacatct    5400
cctgaggact ggccagctgt gtctggcacc acccacacat ccatgtctcc ctcacaaccc    5460
aggaggccga tgagaactgt gaggctcaga aagcgtgggc ggtttgccta aggtcacgta    5520
gctacttcct cactggggtc ctggggcctc agagcctcat ctgaggtaaa ggagcaaagt    5580
tgggattggg gtccaaaatt cactttaact ccaaagccca cacttaac caccctgcct    5640 atttctgtcc aaatgtcacc tgtcctgaat                                    5670
```

<210> SEQ ID NO 5
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 5
tgtacctaag cccacccttt agagc                                         25

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 6
tggcctccag aaacctccaa                                               20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 7

```
gctgatattc tggtgggaaa                                              20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 8
ggcaagagca aaactctgtc                                              20

<210> SEQ ID NO 9
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 9
ctcaggtgtc ctcgaagaaa tcaaa                                        25

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 10
gcttttttgc tgtgagtccc g                                            21

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 11
tggcattgat ctggttcatc                                              20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 12
gtttaggaat cttcccactt                                              20

<210> SEQ ID NO 13
<211> LENGTH: 17
<212> TYPE: DNA
<213> ORGANISM: Artificial Sequence
<220> FEATURE:
<223> OTHER INFORMATION: Description of Artificial Sequence: Primer

<400> SEQUENCE: 13
ctcagcaaca ctcctat                                                 17

<210> SEQ ID NO 14
<211> LENGTH: 16
<212> TYPE: DNA
```

```
<213> ORGANISM: Artificial Sequence
<220> FEATURE:
<223> OTHER INFORMATION: Description of Artificial Sequence: Primer

<400> SEQUENCE: 14
tcctggtctg cagtaa                                                    16

<210> SEQ ID NO 15
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 15
ctatctgagg aacaaactag tagc                                           24

<210> SEQ ID NO 16
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 16
taggacattg cacctagggt ttgt                                           24

<210> SEQ ID NO 17
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 17
aagcttgttc taccacctga actaggc                                        27

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 18
ttacatatga gccttccatg                                                20

<210> SEQ ID NO 19
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 19
ccagacatgt ggtgggacag gg                                             22

<210> SEQ ID NO 20
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 20
cgaggcccca ggaccccagt gagctagcag                                     30
```

```
<210> SEQ ID NO 21
<211> LENGTH: 28
<212> TYPE: DNA
<213> ORGANISM: Artificial Sequence
<220> FEATURE:
<223> OTHER INFORMATION: Description of Artificial Sequence: Primer
<221> NAME/KEY: modified_base
<222> LOCATION: (25)
<223> OTHER INFORMATION: "n" represents a, t, c or g

<400> SEQUENCE: 21
caatgcagcc attctcccca gcacngat                                        28

<210> SEQ ID NO 22
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 22
gttcatcgta cctgcctctg g                                               21

<210> SEQ ID NO 23
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 23
catcgagaag acccagagga tg                                              22

<210> SEQ ID NO 24
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 24
cctcgatttt ggtgtctcgg ac                                              22

<210> SEQ ID NO 25
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 25
ctctggcgtt ctactcacg                                                  19

<210> SEQ ID NO 26
<211> LENGTH: 33
<212> TYPE: DNA
<213> ORGANISM: Artificial Sequence
<220> FEATURE:
<223> OTHER INFORMATION: Description of Artificial Sequence: Primer
<221> NAME/KEY: modified_base
<222> LOCATION: (32)
<223> OTHER INFORMATION: "n" represents a, t, c or g

<400> SEQUENCE: 26
caaataatga tgctttcgaa gtttcagtgg ana                                  33
```

-continued

```
<210> SEQ ID NO 27
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 27
ccagacatgt ggtgggacag gg                                              22

<210> SEQ ID NO 28
<211> LENGTH: 31
<212> TYPE: DNA
<213> ORGANISM: Artificial Sequence
<220> FEATURE:
<223> OTHER INFORMATION: Description of Artificial Sequence: Primer
<221> NAME/KEY: modified_base
<222> LOCATION: (24)
<223> OTHER INFORMATION: "n" represents a, t, c or g

<400> SEQUENCE: 28
cgaggcccca ggacccagt gagnctagca g                                     31
```